US010260068B2

(12) United States Patent
Hino et al.

(10) Patent No.: US 10,260,068 B2
(45) Date of Patent: Apr. 16, 2019

(54) PROPHYLACTIC AGENT AND THERAPEUTIC AGENT FOR FIBRODYSPLASIA OSSIFICANS PROGRESSIVA

(71) Applicants: Sumitomo Dainippon Pharma Co., Ltd., Osaka (JP); Kyoto University, Kyoto (JP)

(72) Inventors: Kyosuke Hino, Osaka (JP); Junya Toguchida, Kyoto (JP); Makoto Ikeya, Kyoto (JP)

(73) Assignees: Sumitomo Dainippon Pharma Co., Ltd., Osaka (JP); Kyoto University, Kyoto (JP)

( * ) Notice: Subject to any disclaimer, the term of this patent is extended or adjusted under 35 U.S.C. 154(b) by 0 days.

(21) Appl. No.: 15/300,088

(22) PCT Filed: Mar. 30, 2015

(86) PCT No.: PCT/JP2015/060015
§ 371 (c)(1),
(2) Date: Sep. 28, 2016

(87) PCT Pub. No.: WO2015/152183
PCT Pub. Date: Oct. 8, 2015

(65) Prior Publication Data
US 2017/0211070 A1    Jul. 27, 2017

(30) Foreign Application Priority Data
Mar. 31, 2014 (JP) ................... 2014-071461

(51) Int. Cl.
*A61K 39/395* (2006.01)
*A61K 38/00* (2006.01)
*A61K 38/16* (2006.01)
*C12N 15/113* (2010.01)
*A61K 31/7088* (2006.01)
*A61K 31/7105* (2006.01)
*A61K 31/713* (2006.01)
*A61K 38/17* (2006.01)
*C07K 14/47* (2006.01)
*C07K 16/22* (2006.01)
*G01N 33/50* (2006.01)
*A61P 19/00* (2006.01)
*A61P 19/04* (2006.01)
*G01N 33/74* (2006.01)

(52) U.S. Cl.
CPC ...... *C12N 15/1136* (2013.01); *A61K 31/7088* (2013.01); *A61K 31/713* (2013.01); *A61K 31/7105* (2013.01); *A61K 38/1741* (2013.01); *A61P 19/00* (2018.01); *A61P 19/04* (2018.01); *C07K 14/473* (2013.01); *C07K 16/22* (2013.01); *G01N 33/5041* (2013.01); *A61K 38/00* (2013.01); *C07K 2317/76* (2013.01); *C07K 2319/30* (2013.01); *C07K 2319/70* (2013.01); *C12N 2310/12* (2013.01); *C12N 2310/14* (2013.01); *C12N 2310/141* (2013.01); *C12N 2310/531* (2013.01); *G01N 33/74* (2013.01); *G01N 2500/02* (2013.01); *G01N 2500/10* (2013.01); *G01N 2800/105* (2013.01)

(58) Field of Classification Search
None
See application file for complete search history.

(56) References Cited

U.S. PATENT DOCUMENTS

| 6,692,925 B1 * | 2/2004 | Miyazono | ............ C07K 14/71 |
| | | | 435/325 |
| 8,895,711 B2 * | 11/2014 | Kaplan | ............... C07K 14/001 |
| | | | 435/6.1 |
| 2010/0184033 A1 * | 7/2010 | West | ................... C12N 5/0606 |
| | | | 435/6.16 |

FOREIGN PATENT DOCUMENTS

| JP | 2008-507288 A | 3/2008 | |
| WO | 2006/012627 A2 | 2/2006 | |
| WO | WO-2007053775 A1 * | 5/2007 | ............ C07K 14/71 |
| WO | 2007/123896 A2 | 11/2007 | |
| WO | 2011/158924 A1 | 12/2011 | |

OTHER PUBLICATIONS

Tokuriki et al. 2009. Current Opin in Struct Biol. 19:596-604.*
Wang et al 2001. J. Biol Chem. 276:49213-49220.*
Tsuchida et al. 2008. Endocrine J. 55:11-21 (Year: 2008).*
Walton et al. (2012. Mol. Cell. Endoc. 359:2-12). (Year: 2012).*
Kitterman et al., "Iatrogenic Harm Caused by Diagnostic Errors in Fibrodysplasia Ossificans Progressiva," Pediatrics, 116: e654-e661 (2005).
Kaplan et al., "The Histopathology of Fibrodysplasia Ossificans Progressiva," The Journal of Bone and Joint Surgery, 75: 220-230 (1993).
Shore et al., "A recurrent mutation in the BMP type I receptor ACVR1 causes inherited and sporatic fibrodysplasia ossificans progressiva," Nature Genetics, 38: 525-527 (2006).
Fukuda et al., "Constitutively Activated ALK2 and Increased SMAD1/5 Cooperatively Induce Bone Morphogenetic Protein Signaling in Fibrodysplasia Ossificans Progressiva," The Journal of Biological Chemistry, 284: 7149-7156 (2009).

(Continued)

*Primary Examiner* — Shulamith H Shafer
(74) *Attorney, Agent, or Firm* — Morgan, Lewis & Bockius LLP

(57) ABSTRACT

The invention provides a prophylactic agent or therapeutic agent for fibrodysplasia ossificans progressiva, containing as an active ingredient a binding inhibitor that inhibits interaction between activin and activin A receptor type I (ACVR1), or an expression suppressor that suppresses expression of activin.

26 Claims, 10 Drawing Sheets
Specification includes a Sequence Listing.

(56) References Cited

OTHER PUBLICATIONS

Van Dinther et al., "ALK2 R206H Mutation Linked to Fibrodysplasia Ossificans Progressiva Confers Constitutive Activity to the BMP Type I Receptor and Sensitizes Mesenchymal Cells to BMP-Induced Osteoblast Differentiation and Bone Formation," Journal of Bone and Mineral Research, 25: 1208-1215 (2010).

Ten Dijke et al., "Activin receptor-like kinases: a novel subclass of cell-surface receptors with predicted serine/threonine kinase activity," Oncogene, 8: 2879-2887 (1993).

Macias-Silva et al., "Specific Activation of Smad1 Signaling Pathways by the BMP7 Type I Receptor, ALK2," The Journal of Biological Chemistry, 273: 25628-25636 (1998).

Mohedas et al., "Development of an ALK2-Biased BMP Type I Receptor Kinase Inhibitor," ACS Chemical Biology, 8: 1291-1302 (2013).

Engers et al., "Synthesis and structure-activity relationships of a novel and selective bone morphogenetic protein receptor (BMP) inhibitor derived from the pyrazolo[1.5-α]pyrimidine scaffold of Dorsomorphin: The discovery of ML347 as an ALK2 versus ALK3 selective MLPCN probe," Bioorganic & Medicinal Chemistry Letters, 23: 3248-3252 (2013).

Kaplan et al., "Restoration of normal BMP signaling levels and osteogenic differentiation in FOP mesenchymal progenitor cells by mutant allele-specific targeting," Gene Therapy, 19: 786-790 (2012).

Shimono et al., "Potent inhibition of heterotopic ossification by nuclear retinoic acid receptor-γ agonists," Nature Medicine, 17: 454-460 (2011).

Lowery et al., "Allele-Specific RNA Interference in FOP-Silencing the FOP gene," Gene Therapy, 19: 701-702 (2012).

Miao et al., "Genetic abnormalities in Fibrodysplasia Ossificans Progressiva," Genes & Genetic Systems, 87: 213-219 (2012).

Ohte et al., "A novel mutation of ALK2, L196P, found in the most benign case of fibrodysplasia ossificans progressiva activates BMP-specific intracellular signaling equivalent to a typical mutation, R206H," Biochemical and Biophysical Research Communications, 407: 213-218 (2011).

Hasegawa et al., "A infantile case of fibrodysplasia ossificans progressiva with multiple anomaly," The Journal of the Japan Pediatric Society, 115: 345 (2011).

Katagiri et al., "Psychopharmacology and Chemistry Necessary for Medical Practice Disease Developing Mechanism of Fibrodysplasis Ossificans Progressiva," Clinical Neuroscience, 28: 480-481 (2010).

Yazicioglu et al., "ACVR1 gene mutations in four Turkish patients diagnosed as fibrodysplasia ossificans progressiva," Gene, 515: 444-446 (2013).

Hamasaki et al., "Pathogenic Mutation of ALK2 Inhibits Induced Pluripotent Stem Cell Reprogramming and Maintenance: Mechanisms of Reprogramming and Strategy for Drug Identification," Stem Cells, 30: 2437-2449 (2012).

Shi et al., "Antisense-Oligonucleotide Mediated Exon Skipping in Activin-Receptor-Like Kinase 2: Inhibiting the Receptor That is Overactive in Fibrodysplasia Ossificans Progressiva," PLoS One, 8: e69096 (2013).

Matsumoto et al., "Induced pluripotent stem cells from patients with human fibrodysplasia ossificans progressiva show increased mineralization and cartilage formation," Orphanet Journal of Rare Diseases, 8: 1-14 (2013).

International Search Report issued in corresponding International Patent Application No. PCT/JP2015/060015 dated Jun. 23, 2015.

International Preliminary Report on Patentability and Written Opinion issued in corresponding International Patent Application No. PCT/JP2015/060015 dated Oct. 13, 2016.

* cited by examiner (A)

(B)

(A)

(B)

PROPHYLACTIC AGENT AND THERAPEUTIC AGENT FOR FIBRODYSPLASIA OSSIFICANS PROGRESSIVA

SEQUENCE LISTING SUBMISSION VIA EFS-WEB

A computer readable text file, entitled "SequenceListing.txt" created on or about Sep. 20, 2016, with a file size of about 208 kb contains the sequence listing for this application and is hereby incorporated by reference in its entirety.

TECHNICAL FIELD

The present invention relates to a prophylactic agent and therapeutic agent for fibrodysplasia ossificans progressiva. More specifically, the invention relates to a prophylactic agent, a method of prevention, a therapeutic agent and a method of treatment that inhibits flare-up as the cardinal symptom of fibrodysplasia ossificans progressiva and/or abnormal formation and growth of cartilage or bone, by inhibiting activity of activin.

BACKGROUND ART

Fibrodysplasia ossificans progressiva (FOP) is a hereditary disease whose cardinal symptoms are swelling with inflammation or pain (also known as "flare-up"), and heterotopic ossification (also known as "ectopic ossification"). In patients with typical fibrodysplasia ossificans progressiva (FOP patients), flare-ups appear from childhood or school age, and heterotopic ossification occurs as flare-ups disappear. During this period, fibrous tissue of the skeletal muscle, fascia, tendons and ligaments, etc., undergoes progressive and heterotopic ossification throughout the body, resulting in articular contracture, deformation or mobility impairment.

Ectopic ossification in FOP is characterized by sudden ectopic ossification elicited by destruction and regeneration of soft tissue such as muscle (Non-Patent Literature 1). The ectopic ossification seen in FOP patients has been reported to take place via the process of endochondral ossification (or endochondral ossification) (Non-Patent Literature 2). Endochondral ossification is a phenomenon in which cartilage forms first and is then replaced by bone.

CITATION LIST

Non-Patent Literature

[Non-Patent Literature 1] Pediatrics, 2005, 116, e654-661.
[Non-Patent Literature 2] J. Bone Joint Surg. Am., 1993, 75(2), 220-230.
[Non-Patent Literature 3] Nat. Genet. 2006, 38, 525-527.
[Non-Patent Literature 4] J. Biol. Chem. 2009, 284(11), 7149-7156.
[Non-Patent Literature 5] J. Bone Miner. Res. 2010, 25(6), 1208-1215.
[Non-Patent Literature 6] Oncogene 1993, 8(10), 2879-2887.
[Non-Patent Literature 7] J. Biol. Chem. 1998, 273(40), 25628-25636.
[Non-Patent Literature 8] ACS Chem. Biol., 2013, 8(6), 1291-1302.
[Non-Patent Literature 9] Bioorg. Med. Chem. Lett., 2013, 23(11), 3248-3252.
[Non-Patent Literature 10] Gene Ther., 2012, 19(7), 786-790.
[Non-Patent Literature 11] Nat. Med., 2011, 17(4), 454-460.

SUMMARY OF INVENTION

Problems to be Solved by the Invention

FOP is a genetic disease passed by autosomal dominant inheritance. FOP has been reported to be caused by a mutation in activin A receptor type I (ACVR1) (Non-Patent Literature 3). ACVR1 is a type I bone morphogenetic protein receptor (BMP receptor). ACVR1, as a BMP receptor, is a serine/threonine kinase that transmits signals into the cell. It has been reported that the mutant form of ACVR1 seen in FOP patients conducts signal transmission in a BMP-independent manner (Non-Patent Literatures 4 and 5), and that its reactivity with BMP is enhanced compared to normal ACVR1 (wild type ACVR1) (Non-Patent Literature 5).

The TGF-β superfamily is composed of more than 20 different members, and is largely divided into the BMP family and the TGF-β family. For example, BMP-7 is one type of cytokine belonging to the BMP family. BMP transmits its signal into the cell by forming a complex with two receptors, type I and type II, which are transmembrane serine/threonine kinases. Activin, on the other hand, is a ligand classified in the TGF-β family, and it is a dimer composed of inhibin β chains. Similar to BMP, activin also transmits its signal into the cell by forming a complex with type I and type II receptors. However, it is known that the receptor molecules that transmit the signals for activin and BMP are different.

The gene for ACVR1, a form of type I BMP receptor, was discovered as a result of searching for genes having sequence homology with human type II activin receptors and nematode Daf-1. ACVR1 is therefore also referred to as activin receptor-like kinase 2 (Non-Patent Literature 6). However, subsequent analysis showed that the physiological ligands of ACVR1 are ligands of the BMP family, such as BMP-7 (Non-Patent Literature 7). In addition, activin has been shown to lack activity of transmitting signals via ACVR1 (Non-Patent Literature 7).

At the current time, FOP is treated using steroids, non-steroidal anti-inflammatory analgesics, bisphosphonates and the like. However, no therapeutic agent exists with clearly confirmed efficacy for inhibiting progression of ectopic ossification.

Compounds that inhibit ACVR1 kinase activity are being studied as treatment methods for FOP (Non-Patent Literatures 8 and 9). Some of such compounds have been confirmed to have action inhibiting ectopic ossification in experiments using animal models with an aspect of FOP pathology.

Other findings that have been reported are that selective suppression of expression of mutant ACVR1 seen in FOP patients using RNA interference technology suppressed osteogenic differentiation of dental pulp stem cells of exfoliated deciduous teeth from FOP patients (Non-Patent Literature 10).

In experiments using animal models with an aspect of FOP pathology, retinoic acid receptor γ agonists have been shown to inhibit ectopic ossification (Non-Patent Literature 11).

As mentioned above, the treatment methods reported to date are all based on suppressing the expression or enzyme activity of ACVR1, or inhibition of downstream signal transduction of ACVR1.

On the other hand, it has been reported that mutant ACVR1 which causes FOP strengthen BMP signal transmission compared to normal ACVR1, and transmits its signal in a BMP-independent manner (Non-Patent Literatures 4 and 5). However, the relationship between these phenomena and FOP pathology has not been elucidated.

Thus, the mechanism of FOP onset is still unclear and no drug has yet been found for suppression and treatment of FOP onset.

The present invention has been accomplished in light of these circumstances, and its object is to provide a prophylactic agent and/or therapeutic agent for fibrodysplasia ossificans progressiva (FOP).

Means for Solving the Problems

Activin is a ligand that also binds with ACVR1 but transmits its signal not through ACVR1 but rather via activin A receptor type IB (ACVR1B). However, as a result of much research, the present inventors have found that in FOP patient derived cells, activin transmits its signal into the cell via mutant ACVR1, and that this abnormal signal transduction is a cause of the heterotopic chondrogenic induction and osteogenic induction seen in FOP patients. As used herein, the phrase "activin binds to ACVR1" includes activin binding to receptor complexes that include ACVR1. Moreover, based on the particular knowledge described above, it was found that substances that suppress binding activity of activin for ACVR1 or substances that suppress activin expression have an effect of suppressing differentiation of mesenchymal stem cell-like cells derived from iPS cell lines established from FOP patients into chondrocytes, or in other words, an effect of suppressing onset or progression of ectopic ossification, and the invention has been completed upon this finding.

Specifically, the invention relates to the following.

[1] A prophylactic agent or therapeutic agent for fibrodysplasia ossificans progressiva, containing as an active ingredient a binding inhibitor that inhibits interaction between activin and activin A receptor type I (ACVR1), or an expression suppressor that suppresses expression of activin.

[2] The prophylactic agent or therapeutic agent according to [1] above, wherein the binding inhibitor is selected from the group consisting of:

activin receptor, its modified forms, and polypeptide fragments including partial sequences thereof, follistatin, follistatin-like protein, their modified forms, and polypeptide fragments including partial sequences thereof, antibodies for activin and antibody fragments thereof including the antigen binding site, and inhibin and its modified forms.

[3] The prophylactic agent or therapeutic agent according to [1] above, wherein the expression suppressor is a nucleic acid that suppresses activin gene expression.

[4] The prophylactic agent or therapeutic agent according to [3] above, wherein the nucleic acid that suppresses activin gene expression is selected from the group consisting of antisense oligonucleotides, siRNA, shRNA, miRNA and ribozymes for the activin gene.

[5] The prophylactic agent or therapeutic agent according to any one of [1] to [4] above, which is for a patient having an amino acid mutation in ACVR1.

[6] The prophylactic agent or therapeutic agent according to [5] above, wherein the amino acid mutation includes an amino acid mutation in the GS domain or kinase domain of the ACVR1.

[7] The prophylactic agent or therapeutic agent according to [6] above, wherein the amino acid mutation in the GS domain or kinase domain includes at least one amino acid mutation selected from the group consisting of amino acid mutations in which the 196th amino acid residue is proline, amino acid mutations in which the 197th amino acid residue is leucine and the 198th amino acid is deleted, amino acid mutations in which the 202nd amino acid residue is isoleucine, amino acid mutations in which the 206th amino acid residue is histidine, amino acid mutations in which the 207th amino acid residue is glutamic acid, amino acid mutations in which the 258th amino acid residue is glycine or serine, amino acid mutations in which the 325th amino acid residue is alanine, amino acid mutations in which the 328th amino acid residue is glutamic acid, arginine or tryptophan, amino acid mutations in which the 356th amino acid residue is aspartic acid, and amino acid mutations in which the 375th amino acid residue is proline, in the amino acid sequence listed as SEQ ID NO: 10.

[8] The prophylactic agent or therapeutic agent according to [6] above, including an amino acid mutation in the ACVR1 GS domain, the amino acid mutation in the GS domain including an amino acid mutation in which the 206th amino acid residue of the amino acid sequence listed as SEQ ID NO: 10 is histidine.

[9] A screening method for a prophylactic agent or therapeutic agent for fibrodysplasia ossificans progressiva, or its candidate substance, the screening method including:

a step of measuring interaction between activin and activin A receptor type I (ACVR1) in the presence of a test substance, and determining a first binding strength, and a step of comparing the first binding strength with a second binding strength determined from the interaction measured in the absence of the test substance, and when the first binding strength is weaker than the second binding strength, selecting the test substance as the candidate substance, or including:

a step of measuring the strength of signal transduction via mutant ACVR1 by activin binding in the presence of a test substance, and determining a first signal strength, and a step of comparing the first signal strength with a second signal strength determined from the strength of the signal transduction measured in the absence of the test substance, and when the first signal strength is weaker than the second signal strength, selecting the test substance as the candidate substance.

[10] A prophylactic agent or therapeutic agent for fibrodysplasia ossificans progressiva, containing as an active ingredient a test substance selected by the screening method according to [9] above.

[11] The prophylactic agent or therapeutic agent according to any one of [1] to [8] and [10] above, which is a drug that suppresses symptoms or progression of heterotopic ossification, or a drug that avoids or suppresses onset of heterotopic ossification.

The invention further relates to the following.

[12] A method of prevention or treatment of fibrodysplasia ossificans progressiva, including administration to a mammal of an effective amount of a binding inhibitor that inhibits interaction between activin and activin A receptor type I (ACVR1), or an expression suppressor that suppresses expression of activin.

[13] The method according to [12] above, wherein the binding inhibitor is selected from the group consisting of:
activin receptor, its modified forms, and polypeptide fragments including partial sequences thereof,
follistatin, follistatin-like protein, their modified forms, and polypeptide fragments including partial sequences thereof,
antibodies for activin and antibody fragments thereof including the antigen binding site, and
inhibin and its modified forms.

[14] The method according to [12] above, wherein the expression suppressor is a nucleic acid that suppresses activin gene expression.

[15] The method according to [14] above, wherein the nucleic acid that suppresses activin gene expression is selected from the group consisting of antisense oligonucleotides, siRNA, shRNA, miRNA and ribozymes for the activin gene.

[16] The method according to any one of [12] to [15] above, wherein the mammal is a human.

[17] The method according to [16] above, wherein the human has an amino acid mutation in ACVR1.

[18] The method according to [17] above, wherein the amino acid mutation includes an amino acid mutation in the GS domain or kinase domain of the ACVR1.

[19] The method according to [18] above, wherein the amino acid mutation in the GS domain or kinase domain includes at least one amino acid mutation selected from the group consisting of amino acid mutations in which the 196th amino acid residue is proline, amino acid mutations in which the 197th amino acid residue is leucine and the 198th amino acid is deleted, amino acid mutations in which the 202nd amino acid residue is isoleucine, amino acid mutations in which the 206th amino acid residue is histidine, amino acid mutations in which the 207th amino acid residue is glutamic acid, amino acid mutations in which the 258th amino acid residue is glycine or serine, amino acid mutations in which the 325th amino acid residue is alanine, amino acid mutations in which the 328th amino acid residue is glutamic acid, arginine or tryptophan, amino acid mutations in which the 356th amino acid residue is aspartic acid, and amino acid mutations in which the 375th amino acid residue is proline, in the amino acid sequence listed as SEQ ID NO: 10.

[20] The method according to [18] above, including an amino acid mutation in the ACVR1 GS domain, the amino acid mutation in the GS domain including an amino acid mutation in which the 206th amino acid residue of the amino acid sequence listed as SEQ ID NO: 10 is histidine.

[21] A binding inhibitor that inhibits interaction between activin and activin A receptor type I (ACVR1), for use in prevention or treatment of fibrodysplasia ossificans progressiva. [22] The binding inhibitor according to [21] above, which is selected from the group consisting of:
activin receptor, its modified forms, and polypeptide fragments including partial sequences thereof,
follistatin, follistatin-like protein, their modified forms, and polypeptide fragments including partial sequences thereof,
antibodies for activin and antibody fragments thereof including the antigen binding site, and
inhibin and its modified forms.

[23] An expression suppressor that suppresses expression of activin, for use in prevention or treatment of fibrodysplasia ossificans progressiva.

[24] The expression suppressor according to [23] above, which is a nucleic acid that suppresses activin gene expression.

[25] The expression suppressor according to [24] above, wherein the nucleic acid that suppresses activin gene expression is selected from the group consisting of antisense oligonucleotides, siRNA, shRNA, miRNA and ribozymes for the activin gene.

[26] Use of a binding inhibitor that inhibits interaction between activin and activin A receptor type I (ACVR1), or an expression suppressor that suppresses expression of activin, in production of a prophylactic agent or therapeutic agent for fibrodysplasia ossificans progressiva.

[27] The use according to [26] above, wherein the binding inhibitor is selected from the group consisting of:
activin receptor, its modified forms, and polypeptide fragments including partial sequences thereof;
follistatin, follistatin-like protein, their modified forms, and polypeptide fragments including partial sequences thereof, antibodies for activin and antibody fragments thereof including the antigen binding site, and
inhibin and its modified forms.

[28] The use according to [26] above, wherein the expression suppressor is a nucleic acid that suppresses activin gene expression.

[29] The use according to [28] above, wherein the nucleic acid that suppresses activin gene expression is selected from the group consisting of antisense oligonucleotides, siRNA, shRNA, miRNA and ribozymes for the activin gene.

[30] An animal model for fibrodysplasia ossificans progressiva, prepared by a method including the following step (1) and step (2):
(1) a step of culturing a cell population including mesenchymal stem cell-like cells prepared from iPS cells having an amino acid mutation in ACVR1, in the co-presence of activin A, and obtaining three-dimensional cartilage pellets, and
(2) a step of subcutaneously administering the three-dimensional cartilage pellets obtained in step (1) to an immune-deficient non-human mammal.

[31] A method of evaluating a prophylactic agent or therapeutic agent for fibrodysplasia ossificans progressiva, or its candidate substance, which includes the following steps (1) to (3):
(1) a step of administering a test substance to an animal model according to [30] above,
(2) a step of evaluating the amount of osteocartilage mass formed heterotopically in the animal model, and
(3) a step of identifying the test substance as a prophylactic agent or therapeutic agent for fibrodysplasia ossificans progressiva, or its candidate substance, when the amount of the osteocartilage mass evaluated in step (2) is smaller than a reference value.

Effects of the Invention

According to the invention it is possible to provide a prophylactic agent and/or therapeutic agent for fibrodysplasia ossificans progressiva.

EMBODIMENTS FOR CARRYING OUT THE INVENTION

Figure 1:
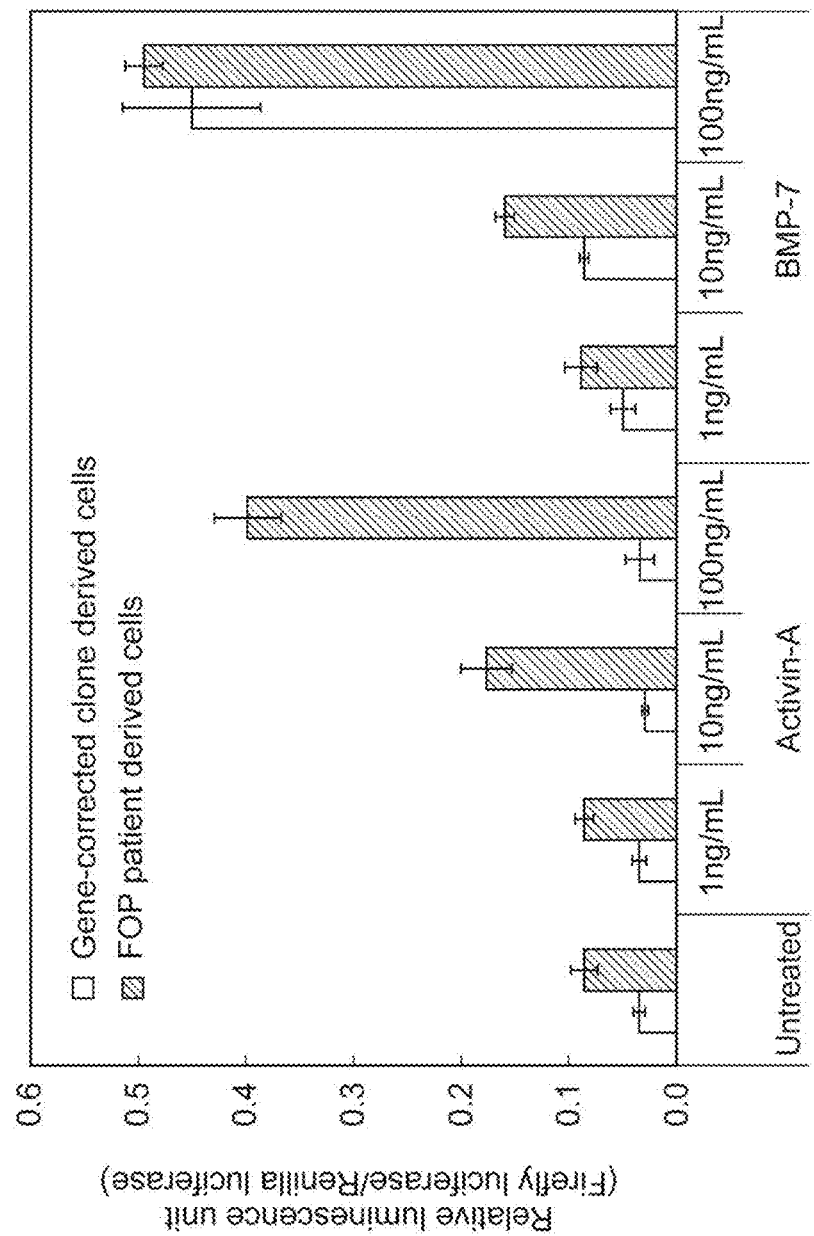
FIG. 1 is a graph showing relative luminescence unit deriving from expression of a luciferase reporter gene, in FOP patient derived cells and gene-corrected clone derived cells.

A preferred embodiment of the invention will now be described in detail. However, the present invention is not limited to the embodiment described below.

A prophylactic agent or therapeutic agent for fibrodysplasia ossificans progressiva according to this embodiment (hereunder also referred to as "FOP prophylactic/therapeutic agent") contains, as an active ingredient, a binding inhibitor that inhibits interaction between activin and activin A receptor type I (ACVR1), or an expression suppressor that suppresses expression of activin.

Fibrodysplasia ossificans progressiva (FOP) is a genetic disease that, typically from childhood, causes systemic progressive and heterotopic ossification (ectopic ossification) of connective tissue, and reduction in mobility or deformation of the extremities and trunk. Ectopic ossification means ossification found in tissue in which osteogenesis normally does not occur. In FOP, the progressive systemic ectopic ossification of connective tissue that occurs notably impairs motor function. The present inventors have found that activin transmits its signal into cells by binding with mutant ACVR1, and this signal transduction is a cause of the heterotopic chondrogenic induction and osteogenic induction seen in FOP patients. Incidentally, while activin binds with ACVR1, it is known that even when it binds with wild type ACVR1, the signal is not transmitted downstream from ACVR1. An FOP prophylactic/therapeutic agent is a drug that suppresses flare-up as the cardinal symptom of FOP, and/or abnormal formation and growth of cartilage or bone, by inhibiting interaction between activin and ACVR1 or suppressing expression of activin. An FOP prophylactic/ therapeutic agent can be understood as being, for example, an inhibitor against binding of activin with ACVR1 or a suppressor of activin expression. The details regarding the mutant ACVR1 will be described below.

Prevention of fibrodysplasia ossificans progressiva means avoiding or suppressing onset of flare-up or ectopic ossification. Such prevention is achieved by the following measures, for example.

(1) Daily administration of an FOP prophylactic/therapeutic agent before onset of flare-up or ectopic ossification.

(2) Administration of an FOP prophylactic/therapeutic agent during factors that bring about flare-up, such as trauma or infection, in order to avoid or suppress onset of flare-up.

(3) Administration of an FOP prophylactic/therapeutic agent during inflammation, pain or flare-up to avoid or suppress onset of ectopic ossification.

Treatment of fibrodysplasia ossificans progressiva means curing the symptoms, improving the symptoms, alleviating the symptoms or suppressing the progression of symptoms of fibrodysplasia ossificans progressiva. For example, the following are included within such treatment.

(1) Suppressing the symptoms of flare-up and shortening the period in which flare-up occurs.

(2) Suppressing the symptoms of ectopic ossification after onset of flare-up.

(3) Suppressing the symptoms or progression of ectopic ossification which is normally progressive.

Activin means a homodimer or heterodimer of inhibin β chains. Examples of inhibin β chains include the βA chain (NCBI Accession No.: NM_002192, SEQ ID NO: 1, 2), βB chain (NCBI Accession No.: NM_002193, SEQ ID NO: 3, 4), βC chain (NCBI Accession No.: NM_005538, SEQ ID NO: 5, 6) and βE chain (NCBI Accession No.: NM_031479, SEQ ID NO: 7, 8). Examples of such activins include activin A (homodimer of βA chains), activin B (homodimer of βB chains) and activin AB (heterodimer of βA chain and βB chain). The inhibin β chain, after translation from mRNA, first has the signal peptide of approximately 18 to 30 amino acid residues at the N-terminal end cut off to result in the pro-form. The pro-form of the inhibin β chain in turn has a polypeptide of approximately 200 to 300 amino acid residues at the N-terminal end cut off to result in the mature inhibin β chain.

Activin A receptor type I (ACVR1) is a type I BMP receptor. ACVR1 is a receptor encoded by a nucleic acid sequence listed as NCBI Accession No.: NM_001105 (SEQ ID NO: 9) or its isoform NM_001111067 (SEQ ID NO: 21), for example. The amino acid sequence of ACVR1 may be the amino acid sequence listed as SEQ ID NO: 10 or 22, for example.

Activin A receptor type IB (ACVR1B) is an activin receptor. Activin transmits its signal into the cell via ACVR1B in the body. Examples of ACVR1B include receptors encoded by the nucleic acid sequences listed as NCBI Accession No.: NM 004302 (variant 1, isoform a; SEQ ID NO: 23), NM_020327 (variant 2, isoform b; SEQ ID NO: 25) and NM_020328 (variant 3, isoform c; SEQ ID NO: 27). The amino acid sequence of ACVR1B may be one of the amino acid sequences listed as SEQ ID NO: 24, SEQ ID NO: 26 and SEQ ID NO: 28, for example.

Activin A receptor type II is a protein that binds with activin to form a complex. In the body, the complex of activin A receptor type II transmits the activin signal via ACVR1B. Activin A receptor type II includes ACVR2A (NCBI Accession No.: NM_001616, SEQ ID NO: 11, 12) and ACVR2B (NCBI Accession No.: NM_001106, SEQ ID NO: 13, 14).

The binding inhibitor that inhibits interaction between activin and activin A receptor type I (ACVR1) (hereunder also referred to simply as "binding inhibitor") is not particularly limited so long as it can inhibit binding of activin as a ligand with ACVR1, or can inhibit binding of activin as a ligand with activin A receptor type II (ACVR2A or ACVR2B) to form a complex, and binding of the complex with ACVR1. Examples of binding inhibitors include partial proteins of the ligand binding site of type I or type II receptor for TGF-β superfamily ligands (activin receptor, etc.), follistatin, follistatin-like protein, antibodies for activin, inhibin, and polypeptide fragments including partial sequences of these, as well as substances that can be screened by the screening method described below (low molecular weight compounds, polypeptides and the like). A "binding inhibitor" is an exogenous protein, etc. as distinct from proteins and the like that are endogenous for the subject of administration of the FOP prophylactic/therapeutic agent. Examples of "exogenous protein, etc." include proteins and the like produced according to genetic engineering methods, and isolated or purified proteins and the like.

The binding inhibitor is preferably selected from the group consisting of:

activin receptor, its modified forms, and polypeptide fragments including partial sequences thereof, follistatin, follistatin-like protein, their modified forms, and polypeptide fragments including partial sequences thereof, antibodies for activin and antibody fragments thereof including the antigen binding site, and inhibin and its modified forms.

Examples of activin receptors include activin A receptor type I (ACVR1), activin A receptor type IB (ACVR1B), and activin A receptor type II (ACVR2A or ACVR2B). The activin receptor as a binding inhibitor binds with activin and inhibits binding between activin and endogenous ACVR1. Thus, signal transduction by binding of activin with mutant ACVR1 is suppressed, and heterotopic chondrogenic induction and osteogenic induction are suppressed. Examples for ACVR1 include proteins including the amino acid sequences listed as SEQ ID NO: 10 or 22. Examples for ACVR1B include proteins including the amino acid sequences listed as SEQ ID NO: 24, 26 or 28. Examples for ACVR2A include proteins including the amino acid sequence listed as SEQ ID NO: 12. Examples for ACVR2B include proteins including the amino acid sequence listed as SEQ ID NO: 14. The activin receptor as a binding inhibitor is preferably ACVR2A or ACVR2B, and more preferably ACVR2A.

A modified form of activin receptor means a protein having an amino acid sequence selected from the group consisting of amino acid sequences having a deletion, substitution, insertion or addition of one or several amino acids in the amino acid sequence of activin receptor, and amino acid sequences having 85% or greater, preferably 90% or greater, more preferably 95% or greater and even more preferably 98% or greater sequence identity with the amino acid sequence of activin receptor, and having the ability to bind with activin.

Preferably, the modified form of ACVR1 is a protein having an amino acid sequence selected from the group consisting of:

(1) amino acid sequences having a deletion, substitution, insertion or addition of one or several amino acids in the amino acid sequence listed as SEQ ID NO: 10, or in an amino acid sequence corresponding to positions 21 to 123 of the amino acid sequence listed as SEQ ID NO: 10, and (2) amino acid sequences having 85% or greater, preferably 90% or greater, more preferably 95% or greater and even more preferably 98% or greater sequence identity with the amino acid sequence listed as SEQ ID NO: 10, or with an amino acid sequence corresponding to positions 21 to 123 of the amino acid sequence listed as SEQ ID NO: 10, and having the ability to bind with activin.

Preferably, the modified form of ACVR1B is a protein having an amino acid sequence selected from the group consisting of:

(1) amino acid sequences having a deletion, substitution, insertion or addition of one or several amino acids in the amino acid sequence listed as SEQ ID NO: 24, in an amino acid sequence corresponding to positions 24 to 126 of the amino acid sequence listed as SEQ ID NO: 24, in the amino acid sequence listed as SEQ ID NO: 26, in an amino acid sequence corresponding to positions 1 to 74 of the amino acid sequence listed as SEQ ID NO: 26, in the amino acid sequence listed as SEQ ID NO: 28 or in an amino acid sequence corresponding to positions 24 to 126 of the amino acid sequence listed as SEQ ID NO: 28, and (2) amino acid sequences having 85% or greater, preferably 90% or greater, more preferably 95% or greater and even more preferably 98% or greater sequence identity with the amino acid sequence listed as SEQ ID NO: 24, with an amino acid sequence corresponding to positions 24 to 126 of the amino acid sequence listed as SEQ ID NO: 24, with the amino acid sequence listed as SEQ ID NO: 26, with an amino acid sequence corresponding to positions 1 to 74 of the amino acid sequence listed as SEQ ID NO: 26, with the amino acid sequence listed as SEQ ID NO: 28, or with an amino acid sequence corresponding to positions 24 to 126 of the amino acid sequence listed as SEQ ID NO: 28, and having the ability to bind with activin.

Preferably, the modified form of ACVR2A or ACVR2B is a protein having an amino acid sequence selected from the group consisting of:

(1) amino acid sequences having a deletion, substitution, insertion or addition of one or several amino acids in the amino acid sequence listed as SEQ ID NO: 12, in an amino acid sequence corresponding to positions 20 to 135 of the amino acid sequence listed as SEQ ID NO: 12, in the amino acid sequence listed as SEQ ID NO: 14 or in an amino acid sequence corresponding to positions 19 to 134 of the amino acid sequence listed as SEQ ID NO: 14, and (2) amino acid sequences having 85% or greater, preferably 90% or greater, more preferably 95% or greater and even more preferably 98% or greater sequence identity with the amino acid sequence listed as SEQ ID NO: 12, with an amino acid sequence corresponding to positions 20 to 135 of the amino acid sequence listed as SEQ ID NO: 12, with the amino acid sequence listed as SEQ ID NO: 14 or with an amino acid sequence corresponding to positions 19 to 134 of the amino acid sequence listed as SEQ ID NO: 14, and having the ability to bind with activin.

As used herein, the number of amino acids substituted, deleted, inserted or added (mutated amino acids) may be in any range in which the modified form has the ability to bind with activin. The number of amino acid mutations is at least 1, and is preferably 1 or several. The indication of "1 or several" is preferably 1 to 5, more preferably 1 to 3 and even more preferably 1 or 2. The mutated amino acid sequence may be a naturally occurring amino acid sequence, i.e. an amino acid sequence with a mutation by spontaneous generation. The mutated amino acid sequence may also be an amino acid sequence having a mutation artificially introduced at a desired site or amino acid residue. When a mutation is to be artificially introduced at a desired site or amino acid residue, the mutation may be artificially introduced as in a naturally occurring mutant. Introduction of an artificial mutation (substitution, deletion, insertion or addition) may be accomplished by partially modifying a nucleotide sequence encoding the amino acid sequence by a common method using a site-specific mutagenesis method by PCR, or another known site-specific mutagenesis method (Proc. Natl. Acad. Sci. USA., 1984 Vol. 81, 5662-5666; Sambrook et al., Molecular Cloning A Laboratory Manual (1989) Second edition, Cold Spring Harbor Laboratory Press).

Sequence identity is the value calculated by appropriate alignment of a query sequence (amino acid sequence to be evaluated) against a reference sequence (for example, the amino acid sequence listed as SEQ ID NO: 10, 12, 14, 24, 26 or 28). Sequence identity may be the value calculated by the CLUSTAL algorithm, for example.

The sequence identity is preferably as high as possible, and specifically it may be 85% or greater, 90% or greater, 95% or greater or 98% or greater.

The modified form of the activin receptor as a binding inhibitor is preferably a modified form of ACVR2A or ACVR2B.

A polypeptide fragment including a partial sequence of the activin receptor or its modified form as a binding inhibitor may be any one that can compete with binding between ACVR1, and activin or a complex of activin and activin A receptor type II (ACVR2A or ACVR2B), and for example, it may be a membrane receptor or soluble receptor, and is preferably a soluble receptor. Examples of membrane receptors include ACVR2A or ACVR2B having the extracellular ligand-binding domain and the transmembrane region, and lacking all of the intracellular region or a portion of the intracellular region including the region necessary for binding with the type I receptor. Examples of soluble receptors include proteins comprising the entire extracellular domain of a receptor selected from the group consisting of ACVR2A, ACVR2B, ACVR1 and ACVR1B, or a portion of the extracellular domain including the ligand-binding domain, and proteins in which such proteins are linked either directly or via a linker sequence with the Fc region of a human-derived antibody, for example.

As polypeptide fragments including partial sequences of the activin receptor or its modified form, there are preferred polypeptide fragments of 100 to 140 amino acid residues, having an amino acid sequence corresponding to the extracellular domain of the activin receptor or its modified form, and having the ability to bind with activin. Such polypeptide fragments include polypeptide fragments of preferably 100 to 135 amino acid residues, more preferably 100 to 130 amino acid residues and even more preferably 100 to 120 amino acid residues.

Examples of amino acid sequences corresponding to the extracellular domain of activin receptor or its modified form, include an amino acid sequence corresponding to positions 20 to 135 of the amino acid sequence listed as SEQ ID NO: 12, an amino acid sequence corresponding to positions 19 to 134 of the amino acid sequence listed as SEQ ID NO: 14, an amino acid sequence corresponding to positions 21 to 123 of the amino acid sequence listed as SEQ ID NO: 10, an amino acid sequence corresponding to positions 24 to 126 of the amino acid sequence listed as SEQ ID NO: 24, an amino acid sequence corresponding to positions 1 to 74 of the amino acid sequence listed as SEQ ID NO: 26, and an amino acid sequence corresponding to positions 24 to 126 of the amino acid sequence listed as SEQ ID NO: 28, as well as these amino acid sequences having a deletion, substitution, insertion or addition of one or several amino acids, and amino acid sequences having 85% or greater, preferably 90% or greater, more preferably 95% or greater and even more preferably 98% or greater sequence identity with these amino acid sequences. Specific examples include Sotatercept (also known as ACE-011 or ActRIIA-IgG1-Fc, a partial polypeptide of ACVR2A corresponding to an amino acid sequence from position 20 to 135 of the amino acid sequence listed as SEQ ID NO: 12; see SEQ ID NO: 1 of International Patent Publication No. WO2006/012627 and Bone 46 (2010) 1082-1088).

According to this embodiment, the polypeptide fragment includes both the polypeptide fragment alone and fusion proteins between the polypeptide fragment and carrier proteins. Examples of such carrier proteins include the antibody Fc fragments, and modified forms of Fc fragments having amino acid sequences with a deletion, substitution, insertion or addition of one or several amino acids. Examples of such fusion proteins include fusion proteins between a polypeptide fragment having the amino acid sequence of positions 20 to 135 of the amino acid sequence listed as SEQ ID NO: 12, and the Fc region of a human-derived antibody or a modified form of the Fc region having an amino acid sequence with a deletion, substitution, insertion or addition of one or several amino acids, fusion proteins between a polypeptide fragment having the amino acid sequence of positions 19 to 134 of the amino acid sequence listed as SEQ ID NO: 14, and the Fc region of a human-derived antibody or a modified form of the Fc region having an amino acid sequence with a deletion, substitution, insertion or addition of one or several amino acids, fusion proteins between a polypeptide fragment having the amino acid sequence of positions 21 to 123 of the amino acid sequence listed as SEQ ID NO: 10, and the Fc region of a human-derived antibody or a modified form of the Fc region having an amino acid sequence with a deletion, substitution, insertion or addition of one or several amino acids, fusion proteins between a polypeptide fragment having the amino acid sequence of positions 24 to 126 of the amino acid sequence listed as SEQ ID NO: 24, and the Fc region of a human-derived antibody or a modified form of the Fc region having an amino acid sequence with a deletion, substitution, insertion or addition of one or several amino acids, fusion proteins between a polypeptide fragment having the amino acid sequence of positions 1 to 74 of the amino acid sequence listed as SEQ ID NO: 26 and the Fc region of a human-derived antibody or a modified form of the Fc region having an amino acid sequence with a deletion, substitution, insertion or addition of one or several amino acids, and fusion proteins between a polypeptide fragment having the amino acid sequence of positions 24 to 126 of the amino acid sequence listed as SEQ ID NO: 28, and the Fc region of a human-derived antibody or a modified form of the Fc region having an amino acid sequence with a deletion, substitution, insertion or addition of one or several amino acids. The fusion protein may be in a form with the polypeptide fragment linked to the carrier protein such as the Fc fragment via a linker peptide. Possible linker peptides include peptides having artificial or natural amino acid sequences with 5, 15, 20, 30 or 50 amino acid residues or more, with relatively low tendency to form a secondary structure. Specific examples include peptides including simple sequences of threonine or serine with glycine, or repetitive sequences of threonine or serine with glycine (for example, TG4 or SG4).

Follistatin is a protein that directly binds with activin and functions as an endogenous antagonist. That is, follistatin as a binding inhibitor binds with activin and inhibits binding between activin and ACVR1. Thus, signal transduction by binding of activin with mutant ACVR1 is suppressed, and heterotopic chondrogenic induction and osteogenic induction are suppressed. Follistatins include follistatin 317 (NCBI Accession No.: NM_006350, SEQ ID NO: 15, 16) and follistatin 344 (NCBI Accession No.: NM_013409, SEQ ID NO: 29, 30). Also included within the scope of follistatin according to the present specification are follistatin 288 which is follistatin 317 comprising the amino acid sequence represented by SEQ ID NO: 16, but with the signal peptide corresponding to the amino acid sequence of positions 1 to 29 removed, follistatin 315 having the signal peptide corresponding to the amino acid sequence of positions 1 to 29 removed from follistatin 344 comprising the amino acid sequence listed as SEQ ID NO: 30, and follistatin 303 having 12 C-terminal amino acid residues of follistatin 315 (the amino acid sequence of positions 333 to 344 of the amino acid sequence listed as SEQ ID NO: 30) removed.

A modified form of follistatin means a protein having an amino acid sequence selected from the group consisting of amino acid sequences having a deletion, substitution, insertion or addition of one or several amino acids in the amino acid sequence of follistatin, and amino acid sequences having 85% or greater, preferably 90% or greater, more preferably 95% or greater and even more preferably 98% or greater sequence identity with the amino acid sequence of follistatin, and having the ability to bind with activin.

Preferably, the modified form of follistatin is a protein having an amino acid sequence selected from the group consisting of:

(1) amino acid sequences having a deletion, substitution, insertion or addition of one or several amino acids in the amino acid sequence listed as SEQ ID NO: 16, in an amino acid sequence having a deletion of the amino acid sequence of positions 1 to 29 in the amino acid sequence listed as SEQ ID NO: 16, in the amino acid sequence listed as SEQ ID NO: 30, in an amino acid sequence having a deletion of the amino acid sequence of positions 1 to 29 in the amino acid sequence listed as SEQ ID NO: 30, or in an amino acid sequence having a deletion of the amino acid sequence of positions 1 to 29 and the amino acid sequence of positions 333 to 344 in the amino acid sequence listed as SEQ ID NO: 30, and (2) amino acid sequences having 85% or greater, preferably 90% or greater, more preferably 95% or greater and even more preferably 98% or greater sequence identity with the amino acid sequence listed as SEQ ID NO: 16, with an amino acid sequence having a deletion of the amino acid sequence of positions 1 to 29 in the amino acid sequence listed as SEQ ID NO: 16, with the amino acid sequence listed as SEQ ID NO: 30, with an amino acid sequence having a deletion of the amino acid sequence of positions 1 to 29 in the amino acid sequence listed as SEQ ID NO: 30, or with an amino acid sequence having a deletion of the amino acid sequence of positions 1 to 29 and the amino acid sequence of positions 333 to 344 in the amino acid sequence listed as SEQ ID NO: 30, and having the ability to bind with activin.

Follistatin-like protein is a protein having an amino acid sequence similar to follistatin, and which binds with activin and can function as an endogenous antagonist. That is, follistatin-like protein as a binding inhibitor binds with activin and inhibits binding between activin and ACVR1. Thus, signal transduction by binding of activin with mutant ACVR1 is suppressed, and heterotopic chondrogenic induction and osteogenic induction are suppressed. Examples of follistatin-like proteins include follistatin-like 1 (also known as FSTL1; NCBI Accession No.: NM_007085 SEQ ID NO: 17, 18) and follistatin-like 3 (also known as FSTL3 or FLRG; NCBI Accession No.: NM_005860 SEQ ID NO: 19, 20). Follistatin-like 3 is more preferred.

A modified form of follistatin-like protein means a protein having an amino acid sequence selected from the group consisting of amino acid sequences having a deletion, substitution, insertion or addition of one or several amino acids in the amino acid sequence of follistatin-like protein, and amino acid sequences having 85% or greater, preferably 90% or greater, more preferably 95% or greater and even more preferably 98% or greater sequence identity with the amino acid sequence of follistatin-like protein, and having the ability to bind with activin.

Preferably, the modified form of follistatin-like protein is a protein having an amino acid sequence selected from the group consisting of:

(1) amino acid sequences having a deletion, substitution, insertion or addition of one or several amino acids in the amino acid sequence listed as SEQ ID NO: 18 or SEQ ID NO: 20, in an amino acid sequence having a deletion of the amino acid sequence of positions 1 to 20 in the amino acid sequence listed as SEQ ID NO: 18, or in an amino acid sequence having a deletion of the amino acid sequence of positions 1 to 26 in the amino acid sequence listed as SEQ ID NO: 20, and (2) amino acid sequences having 85% or greater, preferably 90% or greater, more preferably 95% or greater and even more preferably 98% or greater sequence identity with the amino acid sequence listed as SEQ ID NO: 18 or SEQ ID NO: 20, with an amino acid sequence having a deletion of the amino acid sequence of positions 1 to 20 in the amino acid sequence listed as SEQ ID NO: 18, or with an amino acid sequence having a deletion of the amino acid sequence of positions 1 to 26 in the amino acid sequence listed as SEQ ID NO: 20, and having the ability to bind with activin.

A polypeptide fragment including a partial sequence of follistatin or follistatin-like protein is preferably a polypeptide fragment of 50 to 220 amino acid residues, having an amino acid sequence corresponding to the region of amino acids of follistatin or follistatin-like protein that binds with activin and having the ability to bind with activin. Specific examples of amino acid sequences corresponding to the region of amino acids that binds with activin include an amino acid sequence corresponding to positions 30 to 241 of the amino acid sequence listed as SEQ ID NO: 16. More preferably, the polypeptide fragment is a polypeptide fragment of 50 to 150 amino acid residues, having an amino acid sequence corresponding to positions 30 to 88 or positions 93 to 241 of the amino acid sequence listed as SEQ ID NO: 16, and having the ability to bind with activin.

Inhibin is a heterodimer of the inhibin α chain and inhibin β chain, and it is a protein similar to activin. As a binding inhibitor, inhibin binds to activin A receptor type II and inhibits formation of activin and activin A receptor type II complex. Thus, binding between the complex and ACVR1 is inhibited, signals transmitted into the cell by binding of activin with mutant ACVR1 are suppressed, and heterotopic chondrogenic induction and osteogenic induction are suppressed. Examples of inhibin include inhibin A (heterodimer of a chain and βA chain), and inhibin B (heterodimer of a chain and βB chain). An example of an inhibin α chain is NCBI Accession No.: NM_002191 SEQ ID NO: 31, 32. The inhibin α chain, after translation from mRNA, first has the signal peptide of approximately 18 amino acid residues at the N-terminal end cut off to result in the pro-form. The pro-form of the inhibin α chain is the inhibin α chain matured by cutting off a polypeptide of approximately 200 to 230 amino acid residues from the N-terminal end (for example, corresponding to the amino acid sequence of positions 233 to 366 of the amino acid sequence listed as SEQ ID NO: 32).

A modified form of inhibin means a protein having an amino acid sequence selected from the group consisting of amino acid sequences having a deletion, substitution, insertion or addition of one or several amino acids in the amino acid sequence forming each chain of inhibin, and amino acid sequences having 85% or greater, preferably 90% or greater, more preferably 95% or greater and even more preferably 98% or greater sequence identity with the amino acid sequence of inhibin, and having the ability to inhibit binding of ACVR2A or ACVR2B with activin.

Preferably, the modified form of inhibin is a protein having an amino acid sequence selected from the group consisting of:

(1) amino acid sequences having a deletion, substitution, insertion or addition of one or several amino acids in the amino acid sequence listed as SEQ ID NO: 2, SEQ ID NO: 4 or SEQ ID NO: 32, in an amino acid sequence having a deletion of the amino acid sequence of positions 1 to 28 or positions 1 to 310 in the amino acid sequence listed as SEQ ID NO: 2, in an amino acid sequence having a deletion of the amino acid sequence of positions 1 to 28 or positions 1 to 292 in the amino acid sequence listed as SEQ ID NO: 4, or in an amino acid sequence having a deletion of the amino acid sequence of positions 1 to 18 or positions 1 to 232 in the amino acid sequence listed as SEQ ID NO: 32, and (2) amino acid sequences having 85% or greater, preferably 90% or greater, more preferably 95% or greater and even more preferably 98% or greater sequence identity with the amino acid sequence listed as SEQ ID NO: 2, SEQ ID NO: 4 or SEQ ID NO: 32, with an amino acid sequence having a deletion of the amino acid sequence of positions 1 to 28 or positions 1 to 310 in the amino acid sequence listed as SEQ ID NO: 2, an amino acid sequence having a deletion of the amino acid sequence of positions 1 to 28 or positions 1 to 292 in the amino acid sequence listed as SEQ ID NO: 4, or an amino acid sequence having a deletion of the amino acid sequence of positions 1 to 18 or positions 1 to 232 in the amino acid sequence listed as SEQ ID NO: 32, and having the ability to inhibit binding of ACVR2A or ACVR2B with activin.

The aforementioned activin receptor, follistatin, follistatin-like protein, their modified forms, and their polypeptide fragments, inhibin and modified forms of inhibin (hereunder referred to as "the present protein") can be produced by the following method which is well known to those skilled in the art.

First, a gene coding for the present protein (the present gene) is obtained by a common genetic engineering method [for example, the method described in Sambrook J., Frisch E. F., Maniatis T., Molecular Cloning 2nd edition, Cold Spring Harbor Laboratory Press]. Next, the obtained present gene may be used to produce and obtain the present protein by a common genetic engineering method.

For example, first a plasmid is constructed allowing expression of the present gene in host cells, and the plasmid is introduced into the host cells for transformation. The transformed host cells (transformants) are then cultured and the present protein may be obtained from the cultured product. Preferred examples of such plasmids include those having a promoter that can function in the host cells, and if necessary, the gene coding for the present protein may be introduced into an expression vector having a detectable marker introduced therein. Various available expression vectors are commercially available. Examples of commercially available ones include expression vectors including the restriction enzyme recognition site to be used for introduction into the gene coding for the present protein, and promoters such as SV40 virus promoter, cytomegalovirus promoter (CMV promoter), Elongation factor-1 alpha promoter (EF1α promoter), a synthetic promoter composed of the cytomegalovirus enhancer, chicken β actin gene promoter and the rabbit β-globin gene 3'-untranslated region (CAG promoter), Raus Sarcoma Virus promoter (RSV promoter), β-actin gene promoter and aP2 gene promoter, to be used for expression in mammalian cells.

The host cells may be microbial cells, insect cells, mammalian cells or the like, and either prokaryotic or eukaryotic. From the viewpoint of easier mass preparation of the present protein having physiological activity, it is preferred to use mammalian cells (for example, CHO cells or NS0 cells). The plasmid obtained as described above may be introduced into the host cells by a common genetic engineering method. Culturing of the transformants can be carried out by a common method used for microbial culturing, or culturing of insect cells or mammalian cells. In the case of mammalian cells, for example, culturing is carried out in medium appropriately including trace nutrients such as a suitable carbon source, nitrogen source and vitamins.

The present protein may be obtained by combining methods commonly used for general protein isolation and purification. For example, first the culture supernatant obtained by the culturing mentioned above is recovered and the contaminants are removed by centrifugal separation or the like. Next, the culture supernatant may be purified by a step using any of various types of chromatography including ion-exchange chromatography, hydrophobic chromatography and gel filtration chromatography, either alone or in combinations.

An antibody for activin is preferably an antibody whose antigen is at least one inhibin β chain selected from the group consisting of the inhibin βA chain, inhibin βB chain, inhibin βC chain and inhibin βE chain, and more preferably it is an antibody whose antigen is the inhibin βA chain or inhibin PB chain. An antibody for activin, as a binding inhibitor, binds with activin and inhibits binding between activin and ACVR1. Thus, the signal transmitted into the cell by binding of activin with mutant ACVR1 is suppressed, and heterotopic chondrogenic induction and osteogenic induction are suppressed.

The antibody may include a known isotype and subtype. An antibody may be either a monoclonal antibody or a polyclonal antibody. Such antibodies can be produced according to known production methods for antibodies or antiserum. There are no particular restrictions on the antibody isotype, but IgG, IgM and IgA are preferred. The antibody is not particularly limited so long as it has at least the complementarity determining region (CDR) for specifically recognizing and binding with the target antigen. The antibody may also be an antibody that has been modified by genetic engineering, such as a chimeric antibody, humanized antibody or fully humanized antibody.

An antibody fragment of an antibody may be an antibody fragment including the antigen binding site of the antibody (the variable region). Examples of such antibody fragments include Fab, Fab', F(ab')$_2$, Fv, VH, and single-chain antibodies obtained by linking the H chain (VH) and L chain (VL) of Fv with a suitable linker including scFv, scFv-Fc, diabodies which are polypeptide dimers including VH and VL and assembled by VH-VL interaction between the molecules, and minibodies which are dimers of a portion of the constant region (CH3) bonded to the H chain of scFv, as well as other low molecular weight antibodies and the like.

A low molecular weight antibody includes an antibody fragment lacking a portion of the full length antibody (whole antibody, such as whole IgG). A low molecular weight antibody is not particularly limited so long as it has the ability to bind to antigen. An antibody fragment is not particularly limited so long as it is a portion of the full length antibody, but it preferably includes the heavy chain variable region (VH) and/or light chain variable region (VL).

A single-chain antibody is also referred to as "single-chain Fv", or a "scFv" antibody fragment. A single-chain antibody includes the VH and VL domains of the antibody, those domains existing as polypeptide single chains. The "Fv" fragment is a minimal antibody fragment, including the full antigen recognition site and the binding site. The "Fv" fragment is generally a dimer in which one VH and VL are strongly linked by non-covalent bonding. (VH-VL dimer). The three complementarity determining regions (CDR) of each variable region interact to form an antigen binding site on the surface of the VH-VL dimer. The six CDRs form the antigen binding site in the antibody. However, even with one variable region (or half of Fv including only the three CDRs specific to antigen), it will have the ability to recognize and bind with antigen, although with lower affinity than the full binding site. The scFv polypeptide further includes a polypeptide linker between the VH and VL domain so that the scFv can form the desired structure for antigen binding [Pluckthun, The Pharmacology of Monoclonal Antibodies, vol. 113, Rosenburg and Moore eds. Springer-Verlag, New York, pp. 269-315 (1994)].

The method of producing the antibody is not particularly limited, and any method of producing antibodies that is known in the relevant field may be employed. Examples of such antibody producing methods include hybridoma methods, methods of production using microorganisms with the antibody gene transferred by genetic engineering, methods of screening for suitable antibodies from among a vast clone library comprising numerous molecules by a phage display method, and mass-producing the antibodies in mammalian cells (for example, CHO cells), and methods of directly obtaining antibodies from the serum of immunized animals.

For example, polyclonal antibodies can be produced in the following manner. An antigen protein or its partial peptide is used to immunize a small animal such as a rabbit and the serum is obtained. The obtained serum is prepared by purification using, for example, ammonium sulfate precipitation, a Protein A column, a Protein G column, DEAE ion-exchange chromatography, or an affinity column with coupled antigen protein or synthetic peptide.

The antigen may be prepared by a method using, for example, a baculovirus known to those skilled in the art. When the antigen has low immunogenicity, it may be coupled with a macromolecule having immunogenicity, such as albumin, for the immunization.

The method of producing monoclonal antibodies is carried out by the following steps, for example. First, an animal is immunized with a sensitized antigen by a known method. A common method involves intraperitoneal or subcutaneous injection of the mammal with the sensitizing antigen. Specifically, the sensitizing antigen is diluted and suspended in a suitable amount in PBS (Phosphate-Buffered Saline), physiological saline or the like. An ordinary adjuvant such as Freund's complete adjuvant is optionally mixed with the obtained diluted solution or suspension and emulsified. Next, the emulsified sensitizing antigen is administered to the mammal several times every 4 to 21 days. An appropriate carrier may also be used for immunization with the sensitizing antigen.

The mammal is immunized in this manner, and upon confirming increase in the desired antibody level in the serum, immune cells from the mammal are harvested and used for cell fusion. The preferred immune cells in this case are splenocytes in particular. The other parent cells to be fused with the immune cells may be mammalian myeloma cells. The myeloma cells are preferably any of various known cell lines such as P3U1(P3-X63Ag8U1), P3(P3x63Ag8.653) (J. Immunol. (1979) 123, 1548-1550), P3x63Ag8U.1 (Current Topics in Microbiology and Immunology (1978) 81, 1-7), NS-1 (Kohler, G and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323) or R210 (Galfre, G et al., Nature (1979) 277, 131-133).

The cell fusion between the immune cells and myeloma cells may be carried out basically by a known method, such as the method of Kohler and Milstein et al. (Kohler, G and Milstein, C., Methods Enzymol. (1981) 73, 3-46).

More specifically, the cell fusion is carried out in a common nutrient culture solution in the presence of a cell fusion accelerator, for example. Examples of fusion accelerators that are used include polyethylene glycol (PEG) and Sendai virus (HVJ), and adjuvants such as dimethyl sulfoxide may also be used in addition in order to increase the fusion rate as desired.

The proportion of immune cells and myeloma cells used may be set as desired. For example, the number of immune cells with respect to the number of myeloma cells is preferably 1- to 10-fold. Examples for the culture solution to be used for cell fusion include RPMI 1640 culture solution and MEM culture solution, which are suitable for growth of myeloma cell lines, as well as common culture solutions that can be used for other types of cell culturing. Serum supplement such as fetal calf serum (FCS) may also be used together with the culture solution.

Cell fusion is carried out by the following method. First, prescribed amounts of the immune cells and myeloma cells are thoroughly mixed in the culture solution, and a PEG solution (for example, with an average molecular weight of about 1000 to 6000) pre-heated to about 37° C. is added, usually at a concentration of 30 to 60% (w/v). The obtained cell suspension is mixed to form the desired hybridomas. Next, a suitable culture solution is sequentially added to the cell suspension, and the procedure of centrifugation and removal of the supernatant is repeated to remove the cell fusion agent that is undesired for growth of the hybridomas.

In addition to immunizing animals other than humans with antigen to obtain the hybridomas, human lymphocytes, for example, human lymphocytes that have been immortalized by infection with EB virus, may be sensitized with antigen protein, antigen protein-expression cells or a lysate thereof in vitro, to prepare a human antibody producing cell line. In order to induce a stable and continuous antibody secretion function, sensitized lymphocytes may be fused with mouse myeloma cells similar to those mentioned above or human-derived myeloma cells with permanent division potential, for example, U266, to obtain hybridomas producing human antibody with the desired activity (antigen binding activity).

The hybridomas obtained in this manner can be selected by culturing in a common selective culture solution such as HAT culture solution (culture solution containing hypoxanthine, aminopterin and thymidine). Culturing with HAT culture solution is continued for a sufficient time to allow the cells other than the desired hybridomas (non-fused cells) to die (usually several days to several weeks). Next, a common limiting dilution method is conducted and screening and simple cloning of the desired antibody-producing hybridomas are carried out.

The monoclonal antibody-producing hybridomas prepared in this manner may be subcultured in ordinary culture solution. The hybridomas may be stored for a prolonged period in liquid nitrogen. In order to obtain monoclonal antibodies from the hybridomas, there is employed a method of culturing of the hybridomas according to a common method, and obtaining the culture supernatant, or a method of administering the hybridomas to a compatible mammal and obtaining the ascites fluid of the mammal. Such methods of obtaining a culture supernatant are suitable for obtaining high-purity antibodies. The method of obtaining the ascites fluid of the mammal is suitable for mass production of antibodies.

A human antibody is an antibody that is the expression product of a human-derived antibody gene. A human antibody can be obtained, for example, by administering an antigen to a transgenic animal having the ability to produce human antibodies, by introducing a human antibody gene locus. Mice may be mentioned as transgenic animals. A method of preparing mice that can produce human antibodies is described, for example, in International Patent Publication No. WO02/43478.

Monoclonal antibodies for this embodiment include monoclonal antibodies consisting of a heavy chain and/or light chain having the amino acid sequence of the heavy chain (H chain) and/or light chain (L chain) of an antibody, with a deletion, substitution, insertion or addition of one or several amino acids. For this embodiment, recombinant antibodies that have been artificially modified to reduce heteroantigenicity in humans, such as chimeric antibodies or humanized antibodies, may also be used. Such modified antibodies can be produced using known methods.

A chimeric antibody is an immunoglobulin molecule characterized by bonding between two or more portions from different animal species. Generally speaking, the variable region of a chimeric antibody is derived from a mammalian antibody other than that of a human (for example, a mouse monoclonal antibody), and the immunoglobulin constant region is derived from a human immunoglobulin molecule. Preferably, a variable region with low immunogenicity is selected, and it is combined with a human constant region also having low immunogenicity. Furthermore, the combination is also preferably one having low immunogenicity. Chimeric antibodies include monovalent, bivalent and polyvalent immunoglobulins. A monovalent chimeric antibody is a dimer (HL) formed by a chimeric H chain bonded to a chimeric L chain via a disulfide bond. A bivalent chimeric antibody is a tetramer (H2L2) formed by two HL dimers bonded via at least one disulfide bond.

Chimeric antibodies and methods for their production are already described in the technical field [Morrison et al., Proc. Natl. Acad. Sci. USA 81:6851-6855 (1984); Boulianne et al., Nature 312:643-646 (1984); Liu et al., Proc. Natl. Acad. Sci. USA 84:3439-3443 (1987); Sun et al., Proc. Natl. Acad. Sci. USA, 84:214-218 (1987); Better et al., Science 240:1041-1043 (1988); and Harlow and Lane, ANTIBODIES: A LABORATORY MANUAL Cold Spring Harbor Laboratory (1988)].

Humanized antibodies are also referred to as "reshaped" human antibodies. A humanized antibody is one having the complementarity determining region (CDR) of an antibody of a mammal other than a human, such as a mouse, transplanted into the complementarity determining region of a human antibody. Common gene recombination techniques are also known for humanized antibodies (see European Patent Application Publication No. EP125023, International Patent Publication No. WO92/19759). The method for producing the humanized antibody may be a publicly known method. For example, a DNA sequence designed for linkage of the CDR of a mouse antibody and the framework region (FR) of a human antibody is synthesized by PCR from several oligonucleotides prepared so as to have overlapping sections at the end portions. The obtained DNA is linked with DNA coding for the human antibody constant region, and is then incorporated into an expression vector. The obtained expression vector is introduced into a host and produced, to obtain a humanized antibody (see European Patent Application Publication No. EP239400 and International Patent Publication No. 92-19759). The framework region of the human antibody linked via the CDR is selected so that the complementarity determining region forms a satisfactory antigen binding site. If necessary, amino acids of the variable region framework region of the antibody may be substituted so that the complementarity determining region of the reshaped human antibody forms a suitable antigen binding site (Sato, K. et al., Cancer Res. (1993) 53, 851-856).

The C region of a human antibody is used in a chimeric antibody or humanized antibody. The constant region (C region) of a human antibody may be Cγ, and for example, Cγ1, Cγ2, Cγ3 or Cγ4 may be used. In order to improve the structure of the antibody or the stability of its production, the C region of the human antibody may be modified. A chimeric antibody comprises the variable region of an antibody from a mammal other than a human, and the C region from a human antibody. A humanized antibody comprises the complementarity determining region of an antibody from a mammal other than a human, and the framework region and C region from a human antibody. Chimeric antibodies and humanized antibodies are useful as antibodies to be used for this embodiment because they have low antigenicity in the human body.

A low molecular weight antibody or single-chain antibody can be produced, for example, by treating the antibody with an enzyme such as papain or pepsin to produce antibody fragments, or by constructing a gene coding for the antibody fragments, introducing it into an expression vector and then expressing it in suitable host cells (for example, see Co, M. S. et al., J. Immunol. (1994) 152, 2968-2976, Better, M. & Horwitz, A. H. Methods in Enzymology (1989) 178, 476-496, Pluckthun, A. & Skerra, A. Methods in Enzymology (1989) 178, 497-515, Lamoyi, E., Methods in Enzymology (1989) 121, 652-663, Rousseaux, J. et al., Methods in Enzymology (1989) 121, 663-669, and Bird, R. E. et al., TIBTECH (1991) 9, 132-137).

The scFv fragment can be obtained by linking the H chain V region (variable region) and L chain V region of an antibody. These regions are present in the single polypeptide chains. Generally, scFV will also include a polypeptide linker between VH and VL. A polypeptide linker will allow scFv to form the structure necessary for antigen binding [for a review of scFv see Pluckthun, "The Pharmacology of Monoclonal Antibodies" Vol. 113 (Rosenburg and Moore ed (Springer-Verlag, New York) pp. 269-315, 1994)].

In scFv, the H chain V region and L chain V region are linked via a linker and preferably a peptide linker (Huston, J. S. et al., Proc. Natl. Acad. Sci. U.S.A. (1988) 85, 5879-5883). The H chain V region and L chain V region in scFv may be derived from any of those mentioned above as antibodies. The peptide linker for linking the V region is not particularly limited so long as it does not inhibit expression of the antibody variable regions linked at both ends thereof, and for example, any desired single-chain peptide consisting of 12 to 19 amino acid residues may be used.

DNA coding for scFv can be obtained by the following method, for example. First, using DNA coding for the H chain or H chain V region and DNA coding for the L chain or L chain V region of the antibody as template, a DNA portion coding for a desired amino acid sequence among these sequences is amplified by PCR using a primer pair that defines both ends. Next, the amplified DNA, and DNA coding for the peptide linker portion, and a primer pair specifying both ends for linkage with the H chain and L chain, are combined and amplified by PCR, to obtain DNA coding for scFv. Once the scFv-coding DNA has been prepared, an expression vector containing it and a host transformed by the expression vector can be obtained by common methods. The obtained host may then be used to obtain scFv by a common method.

A diabody is a bivalent antibody fragment constructed by gene fusion (Holliger P et al., Proc. Natl. Acad. Sci. USA 90:6444-6448 (1993), European Patent Application Publication No. 404097, International Patent Publication No. WO93/11161 and elsewhere). A diabody is a dimer composed of two polypeptide chains. Usually, the polypeptide chains forming the diabody each have VL and VH in the same chain, bonded with linkers short enough so that they cannot mutually bind, such as linkers of about 5 amino acid residues. Since the VL and VH encoded on the same polypeptide chain have short linkers between them, they cannot form single-chain variable region fragments and instead form a dimer. Consequently, the diabody has two antigen binding sites.

The fragment sc(Fv)2 is a single-chain low molecular weight antibody having two VH and two VL bonded with a linker or the like (Hudson et al., J Immunol. Methods 1999; 231:177-189). The sc(Fv)2 fragment can be prepared, for example, by connecting two scFv fragments with a linker.

For this embodiment, the linker used to bond the antibody variable regions may be any desired peptide linker that can be introduced by genetic engineering, or a synthetic compound linker (see Protein Engineering, 9(3), 299-305, 1996, for example). When a peptide linker is used, its length is not particularly limited, and it may be appropriately selected by a person skilled in the art according to the purpose. The length of the peptide linker will usually be 1 to 100 amino acid residues, preferably 3 to 50 amino acid residues, even more preferably 5 to 30 amino acid residues and most preferably 12 to 18 amino acid residues (for example, 15 amino acid residues). A synthetic compound linker (chemical crosslinking agent) is a crosslinking agent that is commonly used for crosslinking of peptides, such as N-hydroxysuccinimide (NHS), disuccinimidyl suberate (DSS), bis (sulfosuccinimidyl) suberate (BS³), dithiobis(succinimidyl propionate) (DSP), dithiobis(sulfosuccinimidyl propionate) (DTSSP), ethyleneglycol bis(succinimidyl succinate) (EGS), ethyleneglycol bis(sulfosuccinimidyl succinate) (sulfo-EGS), disuccinimidyl tartrate (DST), disulfosuccinimidyl tartrate (sulfo-DST), bis[2-(succinimideoxycarbonyloxy)ethyl]sulfone (BSOCOES) or bis[2-(sulfosuccinimideoxycarbonyloxy)ethyl] sulfone (sulfo-BSOCOES). Such crosslinking agents are commercially available.

The genes for fragments of these antibodies can be obtained and expressed in the manner described above, and the fragments of these antibodies can be produced in a host.

An antibody fused with a protein is an antibody having a heteroprotein fused at the N-terminus or C-terminus of an antibody, and methods for preparing such are publicly known (for example, Clinical Cancer Research, 2004, 10, 1274-1281). It may also be a chimeric molecule with a heteroprotein bonded to an antibody. Examples of heteroproteins include Fc receptor and cytokines, with no particular limitation to these.

An antibody produced and expressed in the manner described above can be intracellular or extracellular, or isolated from the host, and purified to a homogeneous form. Separation and purification of the antibody to be used for this embodiment can be carried out by affinity chromatography. The column used for affinity chromatography may be, for example, a Protein A column or Protein G column. Examples of carriers to be used in a Protein A column include HyperD, POROS and Sepharose F.F. Other separation and purification methods commonly used for proteins may be employed, with no limitations.

For example, chromatography other than affinity chromatography, or filtration, ultrafiltration, salting out, dialysis or the like may be appropriately selected and combined, to allow isolation and purification of the antibody to be used for this embodiment. Examples of chromatography include ion-exchange chromatography, hydrophobic chromatography and gel filtration chromatography. Such chromatography methods can be applied for HPLC (High Performance Liquid Chromatography). Reverse-phase HPLC may also be used.

The expression suppressor which suppresses expression of activin (hereunder also referred to simply as "expression suppressor") may be any substance that can suppress expression of activin, and it is not particularly limited. The expression suppressor is preferably a nucleic acid that suppresses activin gene expression. When activin gene expression is suppressed, production of activin molecule is also suppressed. Thus, signal transduction by binding of activin with mutant ACVR1 is suppressed, and heterotopic chondrogenic induction and osteogenic induction are suppressed.

The nucleic acid that suppresses activin gene expression is preferably selected from the group consisting of antisense oligonucleotides, siRNA, shRNA, miRNA and ribozymes for the activin gene. Methods for obtaining antisense oligonucleotide, siRNA, shRNA, miRNA and ribozymes are known in the relevant field. A person skilled in the art can easily obtain them based on the aforementioned inhibin β chain gene nucleic acid sequences (the nucleic acid sequences listed as SEQ ID NO: 1, 3, 5 or 7), for example.

Nucleic acid that suppresses gene expression of activin is preferably nucleic acid including a complementary strand to a nucleic acid sequence selected from the group consisting of the nucleic acid sequences corresponding to positions 538 to 556 or positions 1356 to 1374 of the nucleic acid sequence listed as SEQ ID NO: 1, nucleic acid sequences having a deletion, substitution, insertion or addition of one or several nucleic acids of these nucleic acid sequences and nucleic acid sequences having 85% or greater, preferably 90% or greater, more preferably 95% or greater and even more preferably 98% or greater sequence identity with these nucleic acid sequences, and suppressing activin gene expression. The nucleic acid that suppresses gene expression may be either DNA or RNA, and the concept includes both single-stranded nucleic acid sequences and double-stranded nucleic acid sequences. As used herein, the nucleic acid sequence listed as SEQ ID NO: 1, and others, are DNA sequences for convenience, and when it indicates an RNA sequence, uracil (U) is understood to be present instead of thymine (T).

The nucleic acid that suppresses activin gene expression may be nucleic acid that includes a nucleic acid sequence that hybridizes with nucleic acid including the nucleic acid sequence listed as SEQ ID NO: 1, 3, 5 or 7, under stringent conditions, and that suppresses activin gene expression.

The term "stringent conditions" means conditions of incubation for 12 hours at room temperature in a solution containing 6×SSC (1×SSC composition: 0.15 M NaCl, 0.015 M sodium citrate, pH 7.0), 0.5% SDS, 5×Denhardt's, 100 μg/mL denatured salmon sperm DNA and 50% (v/v) formamide, and further rinsing with 0.5×SSC at a temperature of 50° C. or higher. As even more stringent conditions, for example, this includes severe conditions such as incubation at 45° C. or 60° C. for 12 hours, rinsing with 0.2×SSC or 0.1×SSC, and rinsing under temperature conditions of 60° C. or 65° C. or higher.

The number of nucleotides of the nucleic acid that suppresses activin gene expression is not particularly limited. When the nucleic acid is an antisense oligonucleotide for the activin gene, it may be the full sequence or partial sequence of a complementary strand to mRNA encoding activin. The number of nucleotides of the nucleic acid that suppresses activin gene expression may be as short as about 10 nucleotides, or as long as the full sequence of the mRNA or initial transcription product. The antisense oligonucleotide is preferably 15 to 50 nucleotides and more preferably 20 to 30 nucleotides.

The antisense oligonucleotide may be DNA or RNA, or it may be a DNA/RNA chimera. When the antisense oligonucleotide is DNA, the RNA:DNA hybrid formed by the target RNA and antisense DNA is recognized by endogenous RNase H and this causes selective decomposition of the target RNA. Thus, in the case of antisense DNA directing decomposition by RNase H, the target sequence may be not only the sequence in the mature mRNA that has undergone splicing, but also the sequence of the intron region of the initial translation product of the activin gene. The intron sequence can be determined by comparing the genomic sequence and the cDNA nucleotide sequence of the activin gene, using a homology search program such as BLAST or FASTA. In addition, the antisense oligonucleotide of this embodiment may be one that hybridizes with activin mRNA or the initial transcription product to inhibit translation to protein. Moreover, the antisense oligonucleotide may be one that bonds with the activin gene, which is double-stranded DNA, to form a triple strand (triplex) that can inhibit transcription to RNA (antigene).

The nucleotide molecule composing the antisense oligonucleotide may be natural DNA or RNA. The nucleotide molecule may include various chemical modifications in order to improve the stability (chemical stability and/or enzyme stability) or specific activity (affinity with RNA). For example, in order to prevent decomposition by hydrolases such as nucleases, the phosphate residue (phosphate) of each nucleotide composing the antisense oligonucleotide may be replaced with chemically modified phosphate residues such as phosphorothioate (PS), methyl phosphonate or phosphorodithionate. The 2'-hydroxyl of the sugar (ribose) of each nucleotide may be substituted with —OR (where R is $CH_3$(2'-O-Me), $CH_2CH_2OCH_3$(2'-O-MOE), $CH_2CH_2NHC(NH)NH_2$, $CH_2CONHCH_3$, $CH_2CH_2CN$ or the like). The base portion (pyrimidine, purine) may also be chemically modified. Examples of chemical modification include introduction of a methyl group or cationic functional group at the 5'-position of the pyrimidine base, or replacement of the carbonyl group 2'-position with thiocarbonyl.

The conformation of the RNA sugar portion dominantly has two forms, the C2'-endo (S-form) and C3'-endo (N-form), which both exist in equilibrium in single-stranded RNA, but become fixed to the N-form when a double strand is formed. Thus, BNA (Bridged Nucleic Acid) is preferably used in order to impart strong binding capacity for target RNA. BNA is a RNA derivative in which the conformation of the sugar portion is fixed to the N-form by crosslinking between the 2'-oxygen and 4'-carbon. Specific examples of BNA include 2',4'-BNA wherein the 2'-oxygen and 4'-carbon are crosslinked by methylene (also known as LNA (Locked Nucleic Acid)) (Imanishi, T. et al., Chem. Commun., 1653-9, 2002; Jepsen, J. S. et al., Oligonucleotides, 14, 130-46, 2004), and ENA wherein the 2'-oxygen and 4'-carbon are crosslinked with ethylene (Morita, K. et al., Nucleosides Nucleotides Nucleic Acids, 22, 1619-21, 2003).

The antisense oligonucleotide of this embodiment can be prepared by determining the target sequence of the activin gene mRNA or initial transcription product, and using a commercially available DNA/RNA automatic synthesizer (Applied Biosystems, Beckman, etc.) to synthesize a sequence complementary thereto. An antisense oligonucleotide including any of the various modifications mentioned above may also be chemically synthesized by any known method.

When the nucleic acid that suppresses activin gene expression is siRNA, it is preferably 15 to 50 nucleotides, more preferably 15 to 30 nucleotides, even more preferably 18 to 26 nucleotides and yet more preferably 19 to 23 nucleotides.

The siRNA may also have additional nucleotides on the 5'-end or 3'-end. The length of such additional nucleotides is usually about 2 to 4 nucleotides, with 19 or more nucleotides as the full length of the siRNA. The additional nucleotides may be DNA or RNA, but using DNA may allow improvement in the stability of the nucleic acid. Examples for sequences of such additional nucleotides include sequences such as ug-3', uu-3', tg-3', tt-3', ggg-3', guuu-3', gttt-3', ttttt-3' and uuuuu-3', with no limitation to these.

In addition to the double-stranded complementary sequence, a protrusion (overhang) of 1 to 4 nucleotides, preferably 1 to 3 nucleotides and even more preferably 2 nucleotides may be present at the 3'-end or 5'-end of each chain. Specifically, dTdT may be added (where "dT" represents deoxyribonucleic acid). The 3'-end or 5'-end may have flush ends (blunt ends) without addition. The 3'-end and 5'-end of the antisense strand may have protruding sequences (overhangs) so that the sense strand and antisense strand have different numbers of nucleotides.

A preferred example is siRNA consisting of 19 to 21 nucleotides and having blunt ends or overhangs of 1 to 3 nucleotides at each of the 3'-ends of the double strand. Specifically, there may be mentioned siRNA with a total nucleotide length of 21, having a target sequence portion of 19 nucleotides and dTdT added to the 3'-end.

When the nucleic acid that suppresses activin gene expression is shRNA, the sequence complementary to the activin gene in addition to the hairpin loop portion of 5 to 15 nucleotides is preferably 15 to 30 nucleotides, more preferably 15 to 26 nucleotides, even more preferably 15 to 23 nucleotides and yet more preferably 18 to 23 nucleotides.

The siRNA and shRNA can be designed, for example, according to the convention proposed by Elbashir et al. (Genes Dev., 15, 188-200 (2001)) and Teramoto et al. (FEBS Lett. 579(13):p 2878-82 (2005)), based on the cDNA sequence information of the target gene.

There is no particular limitation on the position of the target sequence, but it is preferred to select a target sequence up to about 50 nucleotides from the 5'-UTR and start codon, and from a region other than the 3'-UTR. Among the candidate group of target sequences selected based on this convention and other factors, lack of homology with sequences of 16 to 17 contiguous nucleotides of mRNA other than the target is examined using homology search software such as BLAST (http://www.ncbi.nlm.nih.gov/BLAST/), to confirm specificity of the selected target sequence. For target sequences whose specificity has been confirmed, siRNA is designed as double-stranded RNA comprising a sense strand having a 3'-end overhang of TT or UU at the 19 to 21 nucleotides after AA (or NA), and an antisense strand having the sequence complementary to the 19 to 21 nucleotides and a 3'-end overhang of TT or UU. Short hairpin RNA (shRNA), as the siRNA precursor, can be designed by appropriately selecting a desired linker sequence (for example, about 5 to 25 nucleotides) capable of forming a loop structure, and linking the sense strand and antisense strand via the linker sequence.

The sequence of the siRNA and/or shRNA can be searched for using search software available free of charge on various websites. Examples of such websites include RNAi Target Sequence Selector and shRNA Sequence Designer (http://bioinfo.clontech.com/maidesigner/frontpage.jsp), provided by Clontech, with no limitation to these.

The ribonucleotide molecule composing the siRNA may also be modified in the same manner as antisense oligonucleotide, for improved stability and specific activity. In the case of siRNA, however, the RNAi activity may be lost if all of the ribonucleotide molecules in the naturally occurring RNA are replaced with a modified form. It is therefore necessary for the introduction of modified nucleotides to be minimal to allow function of the RNA-induced silencing complex (RISC).

As a specific example of modification, a portion of the nucleotide molecule composing the siRNA may be replaced with naturally occurring DNA, or RNA having undergone various chemical modifications to improve the stability (chemical stability and/or enzyme stability) or specific activity (affinity with RNA) (see Usman and Cedergren, 1992, TIBS 17,34; Usman et al., 1994, Nucleic Acids Symp. Ser. 31, 163). For example, in order to prevent decomposition by hydrolases such as nucleases, the phosphate residue (phosphate) of each nucleotide composing the siRNA may be replaced with chemically modified phosphate residues such as phosphorothioate (PS), methyl phosphonate or phosphorodithionate. The 2'-hydroxyl of the sugar (ribose) of each nucleotide may be substituted with —OR (where R is $CH_3$(2'-O-Me), $CH_2CH_2OCH_3$(2'-O-MOE), $CH_2CH_2NHC$ $(NH)NH_2$, $CH_2CONHCH_3$, $CH_2CH_2CN$ or the like), or fluorine (—F). It may also have chemical modification (2'-deoxy modification, 2'-H) wherein a portion of the RNA of the siRNA is replaced with DNA.

Examples of other modifications include bridged nucleic acid (BNA) having a structure in which a 2'-position modification group is crosslinked with the 4'-position carbon atom, and more specifically, Locked Nucleic Acid (LNA) in which the 2'-position oxygen atom and the 4'-position carbon atom are crosslinked via methylene, and ethylene bridged nucleic acid (ENA).

The base portion (pyrimidine, purine) may also be chemically modified, and for example, a methyl group or cationic functional group may be introduced at the 5-position of the pyrimidine base, or the 2-carbonyl group may be replaced with thiocarbonyl. Modification methods for antisense oligonucleotides may also be used. The sense strand and antisense strand composing the siRNA may also be chemically modified, via a linker, with a ligand that specifically recognizes a receptor on the cell surface, a peptide, sugar chain, antibody, lipid, positive charge, and oligoarginine, Tat peptide, Rev peptide, Ant peptide, or the like, which by its molecular structure is adsorbed and passes through the cell membrane surface.

The siRNA can be prepared by synthesizing the sense strand and antisense strand of the target sequence on the mRNA using a DNA/RNA automatic synthesizer, denaturing in an appropriate annealing buffer at about 90° C. to about 95° C. for approximately 1 minute, and then annealing at about 30° C. to about 70° C. for about 1 to about 8 hours. It can also be prepared by synthesizing short hairpin RNA (shRNA) as a precursor of the siRNA, and cutting the obtained shRNA using Dicer.

The shRNA can be prepared by designing oligo RNA including a nucleotide sequence having the sense strand and antisense strand of the target sequence on the mRNA linked by insertion of a spacer sequence of a length that can form a suitable loop structure (for example, about 5 to 25 nucleotides), and synthesizing it using a DNA/RNA automatic synthesizer. There may also be used an expression vector constructed so that the shRNA or siRNA is expressed. Vectors that express siRNA and shRNA include tandem types and stem-loop (hairpin) types. A tandem type vector has an expression cassette for the sense strand and an expression cassette for the antisense strand of the siRNA linked in tandem. In a tandem type vector, double-stranded siRNA (dsRNA) is formed by expressing each chain intracellularly and annealing them. A stem-loop type vector, on the other hand, has an shRNA expression cassette inserted into the vector.

In a stem-loop type vector, the shRNA is expressed intracellularly and subjected to processing with Dicer to form dsRNA. The promoter used may be a polII promoter (for example, CMV immediate early promoter), but it is common to use a polIII promoter in order to accomplish more precise transcription of short RNA. As polIII promoters there may be mentioned mouse and human U6-snRNA promoter, human H1-RNase P RNA promoter and human valine-tRNA promoter. As the transcription termination signal there may be used a sequence with 4 or more T in linkage.

Examples of siRNA or shRNA expression vectors include virus vectors such as retroviruses, lentiviruses, adenoviruses, adeno associated viruses, herpesviruses and Sendai virus, and animal cell expression plasmids and the like.

The siRNA can be chemically synthesized according to a common method using a DNA/RNA automatic synthesizer such as a 394 Applied Biosystems, Inc. synthesizer, for example, based on the nucleotide sequence information. Specifically, it can be synthesized using a nucleic acid protecting group known to those skilled in the art (for example, a dimethoxytrityl group at the 5'-end) and a coupling group (for example, phosphoramidite at the 3'-end). That is, a protecting group at the 5'-end is deprotected with an acid such as TCA (trichloroacetic acid), and coupling reaction is conducted. It is then capped with an acetyl group, and the subsequent nucleic acid condensation reaction is conducted. When the siRNA includes modified RNA or DNA, modified RNA (for example, 2'-O-methyl-nucleotide or 2'-deoxy-2'-fluoronucleotide) may be used as the starting material, and the coupling reaction conditions may be appropriately adjusted. For introduction of a phosphorothioate bond with the phosphate bond portion modified, there may be used Beaucage reagent (3H-1,2-benzodithiol-3-one 1,1-dioxide).

Oligonucleotides may be separately synthesized, and attached together by ligation after synthesis (Moore et al., 1992, Science 256, 9923; Draper et al. International Patent Publication No. WO93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204), or attached together by hybridization following synthesis and/or deprotection. The siRNA molecule may be synthesized by a tandem synthesis method. Specifically, both siRNA chains are synthesized as a single continuous oligonucleotide separated by a cleavable linker. The oligonucleotide is then cut to produce the separate siRNA fragments, and the obtained siRNA fragments are hybridized and purified. The linker may be either a polynucleotide linker or a non-nucleotide linker.

The synthesized siRNA molecules may be purified using a method known to those skilled in the art. For example, it may be a purification method by gel electrophoresis or a purification method using high-performance liquid chromatography (HPLC).

For this embodiment, the nucleic acid that suppresses activin gene expression may be a commercial product, an example of which is siRNA for the inhibin βA chain gene (Catalog Nos. S7434, S7435, product of Applied Biosystems). These siRNA nucleotide sequences are S7434 (corresponding to the nucleotide sequence of positions 1356 to 1374 of the nucleic acid sequence listed as SEQ ID NO: 1): sense strand: 5'-CAACAGUCAUCAACCACUAtt-3' (SEQ ID NO: 33), antisense strand: 5'-UAGUGGUUGAUGACU-GUUGag-3' (SEQ ID NO: 34), and S7435 (corresponding to the nucleotide sequence of positions 538 to 556 of the nucleic acid sequence listed as SEQ ID NO: 1): sense strand: 5'-GAACGGGUAUGUGGAGAUAtt-3' (SEQ ID NO: 35), antisense strand: 5'-UAUCUCCACAUACCCGUUCtc-3' (SEQ ID NO: 36). The sequence portions printed in lowercase represent the overhang portions, as portions where the ribose backbone has been replaced with a deoxyribose backbone.

When the nucleic acid that suppresses activin gene expression is a ribozyme, it preferably has 25 to 60 nucleotides, more preferably 30 to 55 nucleotides and more preferably 35 to 50 nucleotides.

Ribozyme nucleic acids include self-splicing RNA seen in infectious RNA such as viroids or virusoids, of which hammerhead types and hairpin types are known. Hammerhead types exhibit enzyme activity with about 40 nucleotides, and the target mRNA alone can be specifically cleaved if several nucleotides at each of both ends adjacent to the portion adopting the hammerhead structure (a total of about 10 nucleotides) are sequences complementary to the desired cleavage sites of the mRNA. When the activin gene mRNA adopts a double-stranded structure by itself, there may be used a hybrid ribozyme comprising a linked virus nucleic acid-derived RNA motif that can specifically bind with RNA helicase, to produce the single-stranded target sequence [Proc. Natl. Acad. Sci. USA, 98(10): 5572-5577 (2001)]. Furthermore, when the ribozyme is to be used in the form of an expression vector including DNA coding for the ribozyme, a tRNA-modified sequence may be further linked as a hybrid ribozyme, in order to accelerate migration of the transcription product into the cytoplasm [Nucleic Acids Res., 29(13): 2780-2788 (2001)].

When the nucleic acid that suppresses activin gene expression is miRNA, it is preferably 20 to 100 nucleotides.

The miRNA inhibits translation from mRNA to protein or contributes to regulation of gene expression by decomposition of mRNA. The miRNA is short-chain (20-25 nucleotide) non-coding RNA present in the cell. Such miRNA functions by the following process. First, single-stranded pri-RNA including miRNA and its complementary strand and capable of adopting a hairpin loop structure is transcribed from DNA. The pri-RNA is then partially cut by an enzyme known as Drosha, present in the nucleus, becoming pre-RNA which is transported out of the nucleus. Next, the pre-RNA is further cut by Dicer and functions as miRNA. Thus, the miRNA may be in the form of pri-RNA or pre-RNA.

The miRNA that suppresses activin gene expression can be obtained from a database such as miRDB (http://mirdb.org/miRDB/index.html), for example, based on cDNA sequence information for the target gene. The miRNA that suppresses activin gene expression may be, for example, has-miR-4482-3p, hsa-miR-4507, hsa-miR-147a, hsa-miR-3940-5p, hsa-miR-4252, hsa-miR-205-5p, hsa-miR-452-3p, hsa-miR-3692-3p, hsa-miR-4699-3p, hsa-miR-513c-3p, hsa-miR-4287, hsa-miR-4685-3p, hsa-miR-513a-3p, hsa-miR-4302, hsa-miR-5094, hsa-miR-4677-5p, hsa-miR-548 au-3p, hsa-miR-26b-5p, hsa-miR-26a-5p, hsa-miR-4465, hsa-miR-548 ar-3p, hsa-miR-1297, hsa-miR-148a-3p, hsa-miR-630, hsa-miR-148b-3p, hsa-miR-152, hsa-miR-548e, hsa-miR-548f, hsa-miR-655, hsa-miR-374c-5p, hsa-miR-920, hsa-miR-548a-3p, hsa-miR-4742-3p, hsa-miR-568, hsa-miR-891b, hsa-miR-3666, hsa-miR-301a-3p, hsa-miR-3924, hsa-miR-5591-5p, hsa-miR-130a-3p, hsa-miR-4668-5p, hsa-miR-130b-3p, hsa-miR-3605-3p, hsa-miR-939, hsa-miR-132-5p, hsa-miR-301b, hsa-miR-302a-5p, hsa-miR-5481, hsa-miR-129-5p, hsa-miR-1298, hsa-miR-4300, hsa-miR-3163, hsa-miR-2682-3p, hsa-miR-362-3p, hsa-miR-541-5p, hsa-miR-4295, hsa-miR-223-3p, hsa-miR-329, hsa-miR-454-3p, hsa-miR-369-3p, hsa-miR-548 g-3p, hsa-miR-4757-5p, hsa-miR-3943, hsa-miR-5685, hsa-miR-218-5p, hsa-miR-345-3p, hsa-miR-593-3p, hsa-miR-642a-3p, hsa-miR-1228-3p or hsa-miR-1237.

The FOP prophylactic/therapeutic agent may be administered orally or parenterally (for example, intravenously, by subcutaneous or intramuscular injection, locally, transrectally, percutaneously, intraspinally or transnasally). The dosage form for oral administration may be, for example, tablets, capsules, pills, granules, powder, liquid, suspension or the like. The dosage form for parenteral administration may be, for example, an aqueous solution for injection, oil solution for injection, ointment, cream, lotion, aerosol, suppository, patch or the like. Such formulations may be prepared using techniques known in the prior art, and may contain nontoxic and inactive carriers or additives commonly used in the field of pharmaceuticals.

For this embodiment, an "effective amount" is an amount of medicinal agent or pharmaceutical that elicits the biological or medical response required by the researcher or physician, in a tissue, system, animal or human.

For this embodiment, the phrase "prophylactic agent or therapeutic agent" is intended to encompass pharmaceutical products that include specific components in specific amounts, as well as various drug products that are directly or indirectly produced from combinations of specific components in specific amounts.

The FOP prophylactic/therapeutic agent may be administered in combination with other compatible drugs, in ranges that do not interfere with the object of the invention. The FOP prophylactic/therapeutic agent and other compatible drug may be administered separately, or they may be administered together as a single pharmaceutical composition. The FOP prophylactic/therapeutic agent may also be administered before, simultaneously with or after the other compatible drug. Examples of other drugs that are compatible with the FOP prophylactic/therapeutic agent include anti-inflammatory analgesics such as steroidal anti-inflammatory analgesics and nonsteroidal anti-inflammatory analgesics, bisphosphonate agents, retinoic acid receptor γ agonists, and the like.

Examples of target mammals include mice, rats, guinea pigs, hamsters, rabbits, cats, dogs, sheep, pigs, cows, horses, goats, monkeys and humans. The FOP prophylactic/therapeutic agent of this embodiment is preferably used for humans.

For administration to humans, the FOP prophylactic/therapeutic agent is administered at preferably 0.0001 to 1000 mg/kg of active ingredient, and more preferably 0.001 to 100 mg/kg of active ingredient, per day, although this will differ depending on the purpose of administration, the method of administration and the conditions in which it is administered (gender, age, body weight, pathology, etc.).

The FOP prophylactic/therapeutic agent is suitable for use for patients having an amino acid mutation in ACVR1 (mutant ACVR1). The term "mutant ACVR1" means a receptor protein including an amino acid sequence with 1 to 2 deletions or substitutions in the amino acid sequence listed as SEQ ID NO: 10, and transmitting its signal downstream by binding with activin.

The amino acid mutation may be one listed in Table 1 below, for example. The amino acid residue numbers listed in the table are the amino acid residue numbers of the amino acid sequence listed as SEQ ID NO: 10.

TABLE 1

| Name | Amino acid residue no. | Pre-mutation amino acid | Post-mutation amino acid |
|---|---|---|---|
| L196P | 196 | Leu | Pro |
| PF197/198L | 197, 198 | Pro, Phe | Leu |
| R202I | 202 | Arg | Ile |
| R206H | 206 | Arg | His |
| Q207E | 207 | Gln | Glu |
| R258G | 258 | Arg | Gly |
| R258S | 258 | Arg | Ser |
| G325A | 325 | Gly | Ala |
| G328E | 328 | Gly | Glu |
| G328R | 328 | Gly | Arg |
| G328W | 328 | Gly | Trp |
| G356D | 356 | Gly | Asp |
| R375P | 375 | Arg | Pro |

The listed amino acid mutations will be understood as being located in the GS domain or kinase domain, based on the correlation diagram of the primary sequence and functional domain of ACVR1 provided in Kaplan et al. Human Mutation, Vol. 30, No. 3, 379-390, 2009, for example. The "GS domain" is the glycine- and serine-rich region in the amino acid sequence. The "kinase domain" is the region necessary for expression of kinase activity in the amino acid sequence.

Thus, the amino acid mutation preferably includes an amino acid mutation in the GS domain or kinase domain of ACVR1. The amino acid mutation in the GS domain or kinase domain preferably includes at least one amino acid mutation selected from the group consisting of amino acid mutations in which the 196th amino acid residue of the amino acid sequence listed as SEQ ID NO: 10 is proline, amino acid mutations in which the 197th amino acid residue is leucine and the 198th amino acid is deleted, amino acid mutations in which the 202nd amino acid residue is isoleucine, amino acid mutations in which the 206th amino acid residue is histidine, amino acid mutations in which the 207th amino acid residue is glutamic acid, amino acid mutations in which the 258th amino acid residue is glycine or serine, amino acid mutations in which the 325th amino acid residue is alanine, amino acid mutations in which the 328th amino acid residue is glutamic acid, arginine or tryptophan, amino acid mutations in which the 356th amino acid residue is aspartic acid, and amino acid mutations in which the 375th amino acid residue is proline, and more preferably an amino acid mutation in the GS domain includes an amino acid mutation wherein the 206th amino acid residue in the amino acid sequence listed as SEQ ID NO: 10 is histidine. In other words, the FOP prophylactic/therapeutic agent may be suitably used for patients having ACVR1 including an amino acid mutation in the GS domain or kinase domain, and specifically, patients having ACVR1 including an amino acid mutation listed in Table 1. Of these, it may be most suitably used for patients having ACVR1 wherein the 206th amino acid residue in the amino acid sequence listed as SEQ ID NO: 10 is histidine.

The prophylactic agent or therapeutic agent for fibrodysplasia ossificans progressiva according to this embodiment, or a screening method for candidate substances for the same, includes:

(1-1) a step of measuring interaction between activin and ACVR1 in the presence of a test substance, and determining a first binding strength, and (1-2) a step of comparing it with a second binding strength determined from the interaction measured in the absence of the test substance, and when the first binding strength is weaker than the second binding strength, selecting the test substance as the candidate substance, or including:

(2-1) a step of measuring the strength of signal transduction via mutant ACVR1 by activin binding in the presence of a test substance, and determining a first signal strength, and (2-2) a step of comparing it with a second signal strength determined from the strength of the signal transduction measured in the absence of the test substance, and when the first signal strength is weaker than the second signal strength, selecting the test substance as the candidate substance.

There are no particular limitations on the ACVR1 used in step (1-1), and mutant ACVR1 may be used.

The test substance is not particularly limited, and a low molecular weight compound, polypeptide, protein, nucleic acid or the like may be used.

The method of measuring interaction between activin and ACVR1 in step (1-1) is not particularly limited so long as it is a method known in the technical field, and for example, there may be mentioned ELISA methods, surface plasmon resonance methods, methods employing Fluorescence Resonance Energy Transfer (FRET), protein fragment complementation methods, and the like.

The indicator of binding strength may be any one that can indicate strength of interaction between activin and ACVR1, and examples include the dissociation constant, luminescence unit, fluorescence intensity and enzyme activity.

In step (1-2), the second binding strength may be measured and determined simultaneously with measurement of the first binding strength, or it may be measured and determined before or afterwards.

Evaluating that "the first binding strength is weaker than the second binding strength" may be either a qualitative comparison or a quantitative comparison. For a quantitative comparison, when the first binding strength is 5 times, 10 times or 100 times weaker than the second binding strength, the test substance may be satisfactorily selected as a candidate substance.

The method for measuring the signal transduction strength via mutant ACVR1 by binding of activin in step (2-1) is not particularly limited so long as it is a method known in the technical field, and for example, it may be a method of measuring the degree of phosphorylation of a signal transduction molecule (for example, SMAD1/5/8) present downstream from mutant ACVR1 by Western blotting or an ELISA method, a method of measuring transcription activity via mutant ACVR1 using a reporter gene, or a method of measuring the ratio of differentiation to chondrocytes or bone cells using FOP patient-derived iPS cells, mesenchymal stem cells or the like. Specifically, step (2-1) may be a step of determining the first signal strength by measuring the strength of signal transduction via ACVR1 in cells expressing mutant ACVR1 that have been contacted with the test substance and activin. Likewise, step (2-2) described below may be considered a step of measuring the signal transduction strength via ACVR1 in cells expressing mutant ACVR1 that have been contacted with activin in the absence of the test substance, and comparing with the determined second signal strength. Cells expressing mutant ACVR1 are not particularly limited so long as they express mutant ACVR1, either exogenously or endogenously. Examples of cells expressing mutant ACVR1 include cells from an FOP patient, and more preferably mesenchymal cells, chondrocytes or bone cells differentiated from FOP patient-derived iPS cells.

The signal strength may be based on any indicator that indicates strength of signal transduction via mutant ACVR1 by binding of activin. Examples for the signal strength include the ratio of phosphorylated SMAD1/5/8 molecule with respect to the total amount of SMAD1/5/8 molecule, the expression level of a reporter gene, the amount of sulfated glycosaminoglycan production from differentiated chondrocytes, and the expression level of a gene whose expression varies with differentiation to chondrocytes or bone cells, or its promoter activity. When a reporter gene is used, for example, the method may involve introducing into cells the reporter gene which is a gene functionally linked with a promoter activated by signal transduction via ACVR1. An example of a promoter activated by signal transduction via ACVR1 is a BMP responsive sequence containing a sequence bound with R-Smad (J. Biol. Chem., 2002, 277(7), 4883-4891). The reporter gene may be a gene that can be quantified by fluorescence, luminescence or coloring, or by supporting fluorescence, luminescence or coloring. Examples of reporter genes include GFP, YFP, RFP, BFP, CFP, aequorin, galactosidase, phosphatase, peroxidase, beta lactamase and luciferase.

In step (2-2), the second signal strength may be measured and determined simultaneously with measurement of the first signal strength, or it may be determined by measurement before or afterwards.

Evaluating that "the first signal strength is weaker than the second signal strength" may be either a qualitative comparison or a quantitative comparison. For a quantitative comparison, when the first signal strength is 5 times, 10 times or 100 times weaker than the second signal strength, the test substance may be satisfactorily selected as a candidate substance.

The test substance selected by the screening method of this embodiment may be a molecule that suppresses increase in phosphorylation of the signal transduction molecule such as SMAD1/5/8, when activin is added to cells expressing mutant ACVR1, a molecule that suppresses activation of a promoter that functions downstream from ACVR1, a molecule that suppresses the expression of a molecule whose expression increases upon differentiation to chondrocytes or bone cells, or the like.

The test substance selected by the screening method may be suitably used as an active ingredient in a prophylactic agent or therapeutic agent for fibrodysplasia ossificans progressiva. That is, the scope of the present invention also encompasses a prophylactic agent or therapeutic agent for fibrodysplasia ossificans progressiva containing, as active ingredients, a substance that inhibits or suppresses interaction, and specifically binding, between activin and ACVR1, and a substance that suppresses signal transduction by binding of activin via mutant ACVR1, which have been selected by screening.

The animal model of fibrodysplasia ossificans progressiva for this embodiment is prepared by a method that includes step (3-1) and (3-2) explained below.

(3-1) A step of culturing a cell population including mesenchymal stem cell-like cells prepared from iPS cells having an amino acid mutation in ACVR1, in the co-presence of activin A, and obtaining three-dimensional cartilage pellets, and (3-2) A step of subcutaneously transplanting the three-dimensional cartilage pellets obtained in step (3-1) to an immune-deficient non-human mammal.

In step (3-1), the iPS cells with an amino acid mutation in ACVR1 may be prepared from somatic cells of an FOP patient, for example. The somatic cells from an FOP patient are not particularly limited so long as they are somatic cells that have been derived from an FOP patient, and skin-derived cells, blood-derived cells and the like may be mentioned. An example of a method of producing the iPS cells is the method of Yamanaka et al. (Cell, 2007, 131 (5), 8611-8672). A method of preparing a cell population including mesenchymal stem cell-like cells from iPS cells may be culturing in a culture solution containing added TGF-β inhibitor and GSK3β inhibitor, according to Example 1 of the present specification. SB-431542 is an example of a TGF-β inhibitor. CHIR99021 is an example of a GSK3β inhibitor. The cells are cultured to form chondrocyte pellets. The obtained chondrocyte pellets may then be cultured in the presence of human activin A for 15 to 25 days to obtain three-dimensional cartilage pellets. The method described in Example 3 may be mentioned as a specific method. The addition concentration of human activin A may be 50 ng/mL to 150 ng/mL.

There are no particular limitations on the immune-deficient non-human mammal used for step (3-2), but it is preferably a rodent, and specifically a mouse (for example, NOD-SCID mouse), rat or the like. There are no particular limitations on the transplantation site for the three-dimensional cartilage pellets, and subcutaneous transplantation may be carried out on the dorsal side of the animal.

The animal model of fibrodysplasia ossificans progressiva may be used for evaluation of a prophylactic agent or therapeutic agent for fibrodysplasia ossificans progressiva, or a candidate substance for the same. That is, by administering the test substance to the animal model and evaluating the amount of heterotopically formed osteocartilage mass in the animal, it is possible to evaluate whether or not the test substance can serve as a prophylactic agent or therapeutic agent for fibrodysplasia ossificans progressiva, or a candidate substance for the same. For example, when the amount of evaluated osteocartilage mass is smaller than a reference value, the test substance is identified as a prophylactic agent or therapeutic agent for fibrodysplasia ossificans progressiva, or a candidate substance for the same. The reference value may be, for example, the amount of osteocartilage mass evaluated by the same method as described above, except for not administering the test substance to the animal model. The method of measuring the amount of osteocartilage mass is not particularly limited, but specifically the transplant site of the animal may be observed by X-ray image analysis. Alternatively, the heterotopically formed osteocartilage mass in the animal may be recovered and quantified by a method known to those skilled in the art.

EXAMPLES

The invention will now be explained in further detail by examples, with the understanding that the invention is not limited in any way to these examples.

Example 1: Evaluation of Transcription Activity Via FOP Patient-Derived ACVR1

(Method)
Following the method of Yamanaka et al. (Cell, 2007, 131 (5), 8611-8672), FOP patient-derived iPS cells (hereunder also referred to as "patient-derived iPS cell line") were established. The patient cells were confirmed to be cells having a typical FOP-associated mutation in the ACVR1 gene. The mutation is a substitution of the 206th arginine residue of the amino acid sequence of ACVR1 (the amino acid sequence listed as SEQ ID NO: 10) with a histidine residue. Next, for use as a control, an iPS cell line with the ACVR1 gene mutation repaired to the normal type (wild type) by gene repair by a BAC knockin vector (hereunder also referred to as "gene-corrected iPS cell clone" or "gene-rescued iPS cell clone") was established.

The patient-derived iPS cell line and gene-corrected iPS cell line were cultured on the matrix of a Matrigel coated plate (trade name: Growth Factor Reduced (GFR)BD Matrigel® by Becton & Dickinson), using mTeSR1 (Stem Cell Technologies) for 2 days under feeder-free conditions. Next, using serum-free medium [F12 Nutrient Mixture (product of Gibco)/Iscove's Modified Dulbecco's Medium (IMDM) (product of Sigma-Aldrich Japan, KK.)/0.5% bovine serum albumin (BSA) (product of Sigma-Aldrich Japan, KK.)/1% Chemically Defined Lipid (CD-Lipid) (product of Gibco, trade name: Chemically Defined Lipid Concentrate)/15 µg/mL apotransferrin (product of Sigma-Aldrich Japan, KK., trade name: apo-Transferrin human)/7 µg/mL insulin (product of Wako Pure Chemical Industries, Ltd., trade name: Insulin, Human, recombinant)/0.45 mM 1-Thioglycerol (product of Sigma-Aldrich Japan, KK.)] with addition of 10 µM SB-431542 (product of Selleck Chemicals) and 1 µM CHIR99021 (product of Wako Pure Chemical Industries, Ltd.), the patient-derived iPS cell line and gene-corrected iPS cell line were further cultured for 1 week under feeder-free conditions for differentiation to neural crest cells. The cells were then labeled with anti-CD271-APC antibody (product of Becton & Dickinson, trade name: Alexa Fluor®, 647 Mouse anti-Human CD271), and BD FACSAriaII (product of Becton & Dickinson) was used for sorting of the CD271 positive cells. Next, the sorted cells were subcultured several times with alpha Modified Eagle Minimum Essential Medium (αMEM) (product of Nacalai Tesque, Inc.)/10% fetal calf serum (FBS) (product of Nichirei Biosciences)/5 ng/mL FGF-2 (product of Wako Pure Chemical Industries, Ltd.) for differentiation to mesenchymal stem cell-like cells, and were supplied for the following experiment. The mesenchymal stem cell-like cells differentiated from the patient-derived iPS cell line will also be referred to as "FOP patient derived cells", and the mesenchymal stem cell-like cells differentiated from the gene-corrected iPS cell clone will also be referred to as "gene-corrected clone derived cells".

After mixing Firefly luciferase reporter plasmid having the BMP responsive sequence in the promoter region (J. Biol. Chem., 2002, 277(7), 4883-4891) and a plasmid having a nucleic acid sequence coding for *Renilla* luciferase downstream from CMV promoter, as an internal standard (product of Promega Corp., trade name: phRL-CMV Vector), FuGene® HD (Promega Corp.) was used for transfection into the mesenchymal stem cell-like cells. At 6 hours after transfection, human activin A (product of R&D Systems, Inc., trade name: Recombinant Human/Mouse/Rat Activin A, final concentrations: 1 ng/mL, 10 ng/mL, 100 ng/mL) or human BMP-7 (product of R&D Systems, Inc., trade name: Recombinant Human BMP-7, final concentrations: 1 ng/mL, 10 ng/mL, 100 ng/mL) was added, and the transfected cells were cultured for 16 hours. Next, the luciferase activity was measured according to the protocol provided with a Dual-Glo Luciferase Assay System (product of Promega Corp.). The luminescence was detected using an EnVision Multilabel Counter (product of Perkin-Elmer). The transcription activity via the BMP responsive sequence was evaluated using the measured value for firefly luciferase activity divided by the measured value for *Renilla* luciferase activity. The results are shown in FIG. 1. In FIG. 1, the bar graph indicates the mean values for each treated group, and the error bars represent standard deviation (S.D.).

(Results)
As shown in FIG. 1, transcription activity via ACVR1 was significantly increased in the FOP patient derived cells by treatment with 10 ng/mL and 100 ng/mL of human activin A (10 ng/mL P<0.01, 100 ng/mL P<0.001, Dunnett's multiple comparisons t test). This phenomenon was not seen with the gene-corrected clone derived cells, however. In contrast, with treatment by BMP-7, the transcription activity increased in a concentration-dependent manner in both the FOP patient derived cells and the gene-corrected clone derived cells (FOP patient derived cells: 10 ng/mL and 100 ng/mL P<0.001, gene-corrected clone: 100 ng/mL P<0.001, Dunnett's multiple comparisons t test with respect to untreated group for both cells). These results confirmed that activin A activates the BMP responsive sequence in a specific manner in FOP patient derived cells.

Example 2: Evaluation of SMAD1/5/8 Phosphorylation (Method)
Mesenchymal stem cell-like cells from a patient iPS cell line and a gene-corrected iPS cell clone were each prepared by the same method as Example 1. Culturing was conducted for 60 minutes with addition of 10 ng/mL and 100 ng/mL of human activin A or 100 ng/mL of human BMP-7 to the mesenchymal stem cell-like cells. The cells were then solubilized with 300 μL of a dissolving solution (70 mM Tris-HCl buffer solution, pH 6.8, 11.2% glycerol, 3% sodium dodecyl sulfate), and a cell extract was prepared. The amount of phosphorylated SMAD1/5/8 and the amount of total SMAD1/5/8 in the obtained cell extract were quantified by Western blotting. As the primary antibody for phosphorylated SMAD1/5/8 there was used rabbit anti-phosphorylated SMAD1/5/8 antibody [product of Cell Signaling Tech., trade name: Phospho-Smad1 (Ser463/465)/Smad5 (Ser463/465)/Smad8 (Ser426/428) Antibody (Rabbit)], and as the primary antibody for total SMAD1/5/8 there was used rabbit anti-total SMAD1/5/8 antibody [product of Santa Cruz Biotechnology, trade name: Smad1/5/8 Antibody (N-18)-R (Rabbit)]. The secondary antibody used was horseradish peroxidase conjugated anti-rabbit antibody (product of Cell Signaling Tech., trade name: Anti-rabbit IgG, HRP-linked Antibody). The substrate used for chemiluminescence was ECL Prime (product of GE Healthcare), and ChemiDocXRSPlus (product of Bio-Rad Laboratories, Inc.) was used for the detection. The results are shown in FIG. 2.

(Results)

Figure 2:
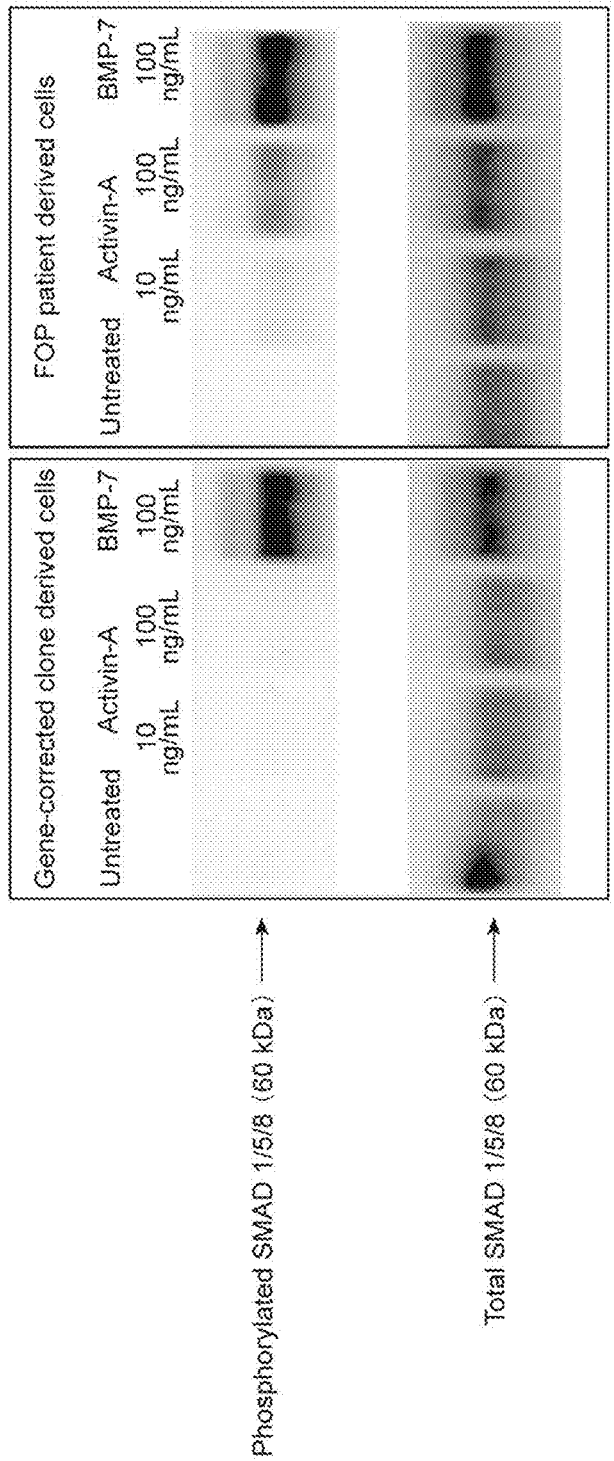
FIG. 2 is a Western blot photograph showing the amounts of phosphorylated SMAD1/5/8 and total SMAD1/5/8 in FOP patient derived cells and gene-corrected clone derived cells.

As shown in FIG. 2, for the FOP patient derived cells, phosphorylation of SMAD1/5/8 was induced by treatment with human activin A. With the gene-corrected clone derived cells, however, although phosphorylation of SMAD1/5/8 occurred by treatment with human BMP-7, no phosphorylation of SMAD1/5/8 was induced by treatment with human activin A. No significant change in the amount of total SMAD1/5/8 was observed with treatment with human activin A or human BMP-7. These results confirmed that ACVR1 functions normally in gene-corrected clone derived cells, but phosphorylation of SMAD1/5/8 induced by human activin A is a phenomenon that occurs specifically in FOP patient derived cells.

Example 3: Effect on Differentiation to Chondrocytes (Method)

Figure 3:
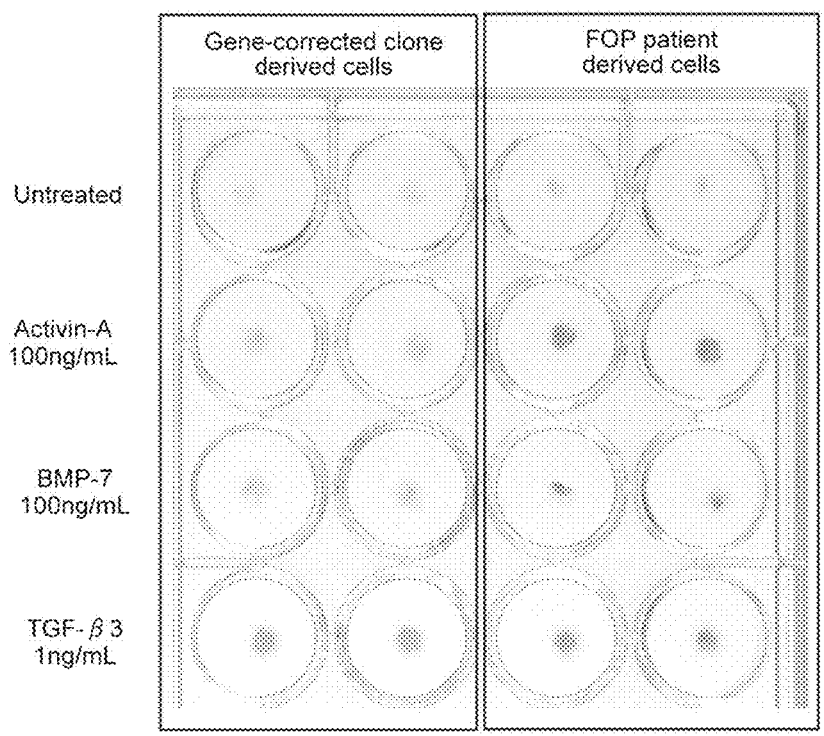
FIG. 3 is a photograph of chondrocytes differentiated from FOP patient derived cells and gene-corrected clone derived cells, which have been stained with Alcian blue.
Figure 4:
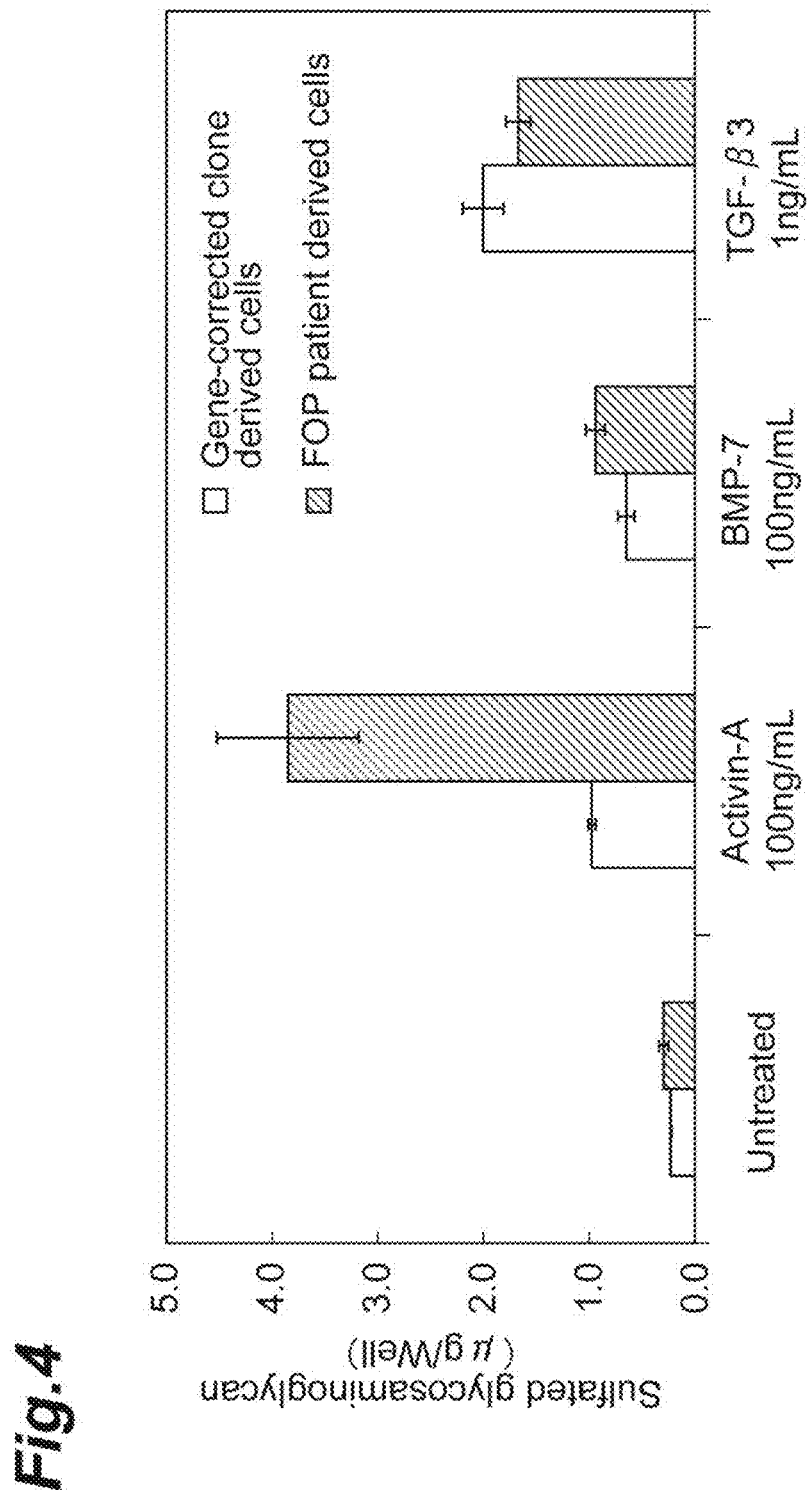
FIG. 4 is a graph showing amounts of sulfated glycosaminoglycan in chondrocytes differentiated from FOP patient derived cells and gene-corrected clone derived cells.

Mesenchymal stem cell-like cells from a patient iPS cell line and a gene-corrected iPS cell clone were each prepared by the same method as Example 1. The mesenchymal stem cell-like cells were cultured for 6 days under the medium conditions used in the method of Umeda et al. (Sci. Rep., 2012, 2, 455), for differentiation to chondrocytes. During differentiation, 100 ng/mL of human activin A, 100 ng/mL of human BMP-7 or 1 ng/mL of human TGF-β3 (product of R&D Systems, Inc., trade name: Recombinant Human TGF-beta 3) was added and the effect of each factor on differentiation to chondrocytes was examined. The extent of differentiation to chondrocytes was measured with Alcian blue dye and a sulfated glycosaminoglycan assay kit (product of Biocolor, Ltd., trade name: Blyscan Glycosaminoglycan Assay Kit). The results are shown in FIG. 3 and FIG. 4. In FIG. 4, the bar graph indicates the mean values for each treated group, and the error bars represent S.D.

(Results)

The results of Alcian blue staining demonstrated that 100 ng/mL of human activin A notably enhances differentiation from FOP patient derived cells to chondrocytes (FIG. 3). The sulfated glycosaminoglycan assay also demonstrated that human activin A very notably enhances cartilage induction in FOP patient derived cells (FIG. 4, $P<0.001$ for both the FOP patient derived cells and gene-corrected cells, Dunnett's multiple comparisons t test with respect to untreated group for both cells; 4-fold sulfated glycosaminoglycan production observed in FOP patient derived cells compared to gene-corrected cells). BMP-7 and TGF-β significantly enhanced cartilage induction in both cells (FOP patient derived cells: BMP-7 $P<0.05$, TGF-β3 $P<0.001$, gene-corrected cells: $P<0.001$ for both BMP-7 and TGF-β3, Dunnett's multiple comparisons t test with respect to untreated group for each cells). However, the effect was weaker compared to the effect exhibited by activin A on FOP patient derived cells, and for TGF-β3, no significant difference was observed between the FOP patient derived cells and the gene-corrected clone derived cells.

Example 4: Effect by Inhibition of ACVR1 or BMPR1A Expression (Method)

Figure 5:
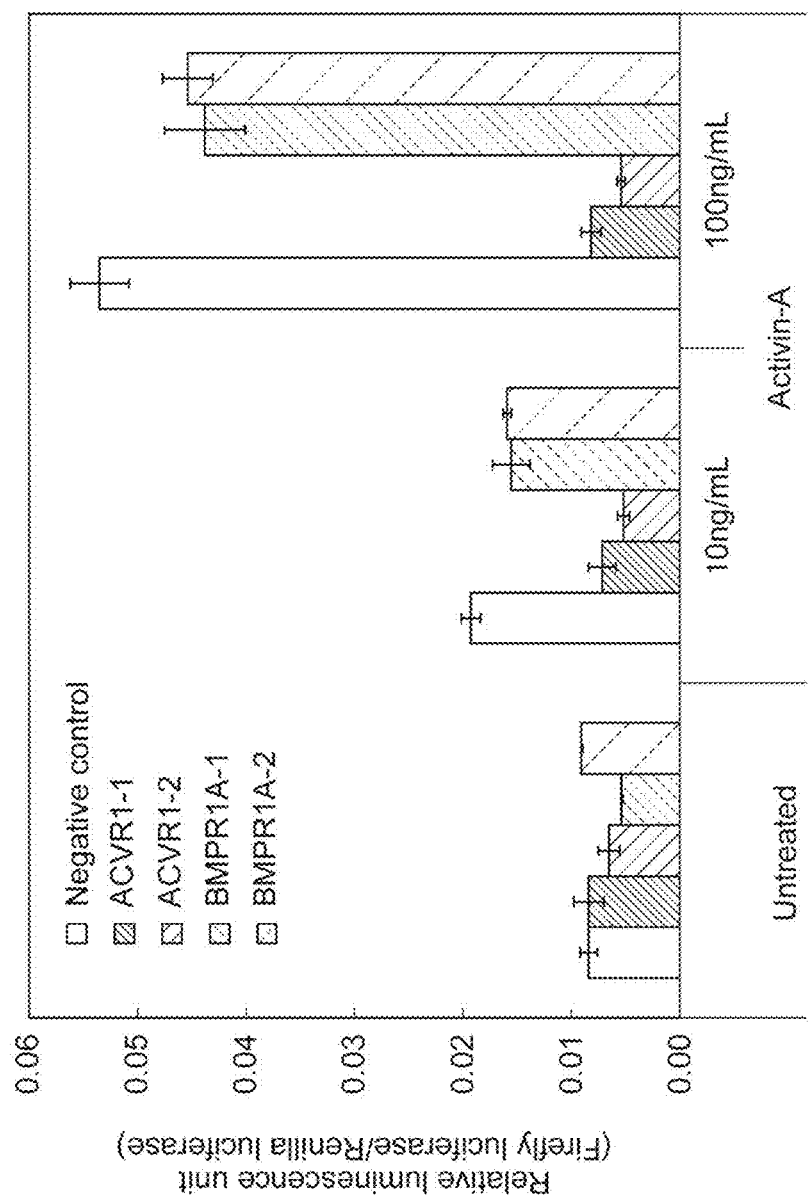
FIG. 5 is a graph showing relative luminescence unit deriving from expression of a luciferase reporter gene, in FOP patient derived cells.

Patient iPS cell line-derived mesenchymal stem cell-like cells were prepared by the same method as Example 1. The cells were transfected with a Firefly luciferase reporter plasmid having the BMP responsive sequence in the promoter region, a plasmid having a nucleic acid sequence coding for *Renilla* luciferase downstream of the CMV promoter, as an internal standard, and siRNA for ACVR1 or BMPR1A, using a Lipofectamine 2000 (product of Invitrogen Corp.), for knockdown of ACVR1 or BMPR1A expression. BMPR1A is a type I receptor that transmits the BMP signal. The siRNA used for knockdown was siRNA purchased from Applied Biosystems, having two different sequences for each gene (Catalog Nos. ACVR1:S975, S976, BMPR1A:S281, S282). The cells were also cultured for 16 hours with addition of activin A in the same manner as Example 1. The cells were then solubilized and the luciferase activity was measured. The results are shown in FIG. 5. In FIG. 5, the bar graph indicates the mean values for each treated group, and the error bars represent S.D. Here, the sequences of the siRNA used for the test were S975: sense strand: 5'-GGAUCAUUCGUGUACAUCAtt-3' (SEQ ID NO: 37), antisense strand: 5'-UGAUGUACAC-GAAUGAUCCaa-3' (SEQ ID NO: 38), S976: sense strand: 5'-GUUGCUCUCCGAAAAUUUAtt-3' (SEQ ID NO: 39), antisense strand: 5'-UAAAUUUUCGGAGAGCAACtc-3' (SEQ ID NO: 40), S281: sense strand: 5'-GGCCGAUAUG-GAGAAGUAUtt-3' (SEQ ID NO: 41), antisense strand: 5'-AUACUUCUCCAUAUCGGCCtt-3' (SEQ ID NO: 42), S282: sense strand: 5'-GAAUCUGGAUAGUAUGCUUtt-3' (SEQ ID NO: 43), antisense strand: 5'-AAGCAUAC-UAUCCAGAUUCtg-3' (SEQ ID NO: 44). The sequence portions printed in lowercase represent the overhang portions, as portions where the ribose backbone has been replaced with a deoxyribose backbone.

(Results)

As shown in FIG. 5, when using both types of ACVR1 siRNA (ACVR1-1 and ACVR1-2, corresponding to S975 and S976, respectively), transcription activation of the BMP responsive sequence by human activin A in the FOP patient derived cells disappeared. On the other hand, with knockdown of BMPR1A by siRNA (BMPR1A-1 and BMPR1A-2, corresponding to S281 and S282, respectively), the action of human activin A in the FOP patient derived cells was not affected. It was thus confirmed that the activin signal in FOP patient derived cells is transmitted via mutant ACVR1, which is unique to FOP patients.

Example 5: Evaluation of Binding Inhibitor (Method)

Figure 6:
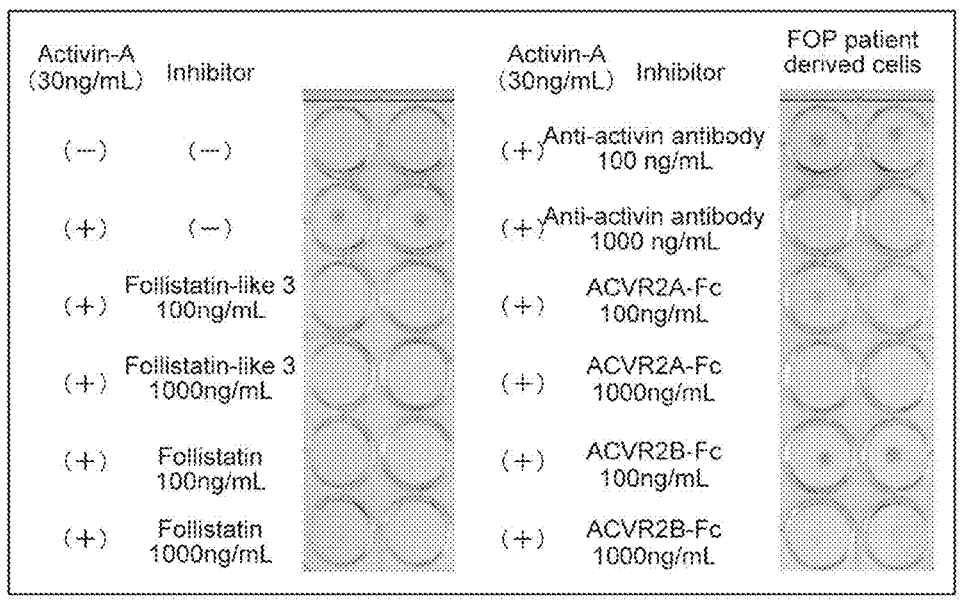
FIG. 6 is a photograph showing chondrocytes differentiated from FOP patient derived cells which have been stained with Alcian blue (A), and a graph showing amounts of sulfated glycosaminoglycan in chondrocytes differentiated from FOP patient derived cells (B).
Figure 6:
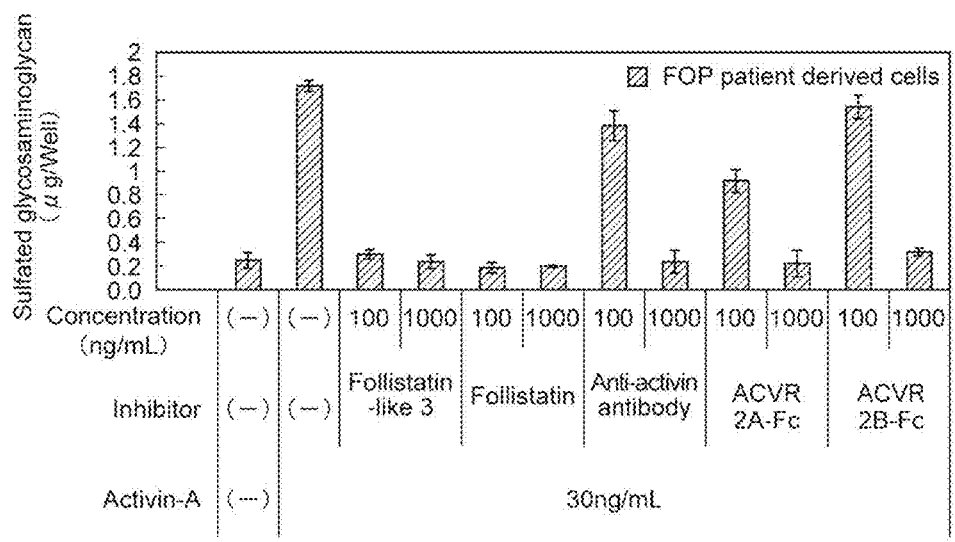

Patient iPS cell line-derived mesenchymal stem cell-like cells were prepared by the same method as Example 1. The mesenchymal stem cell-like cells were cultured for 6 days by the same method as Example 3, for differentiation to chondrocytes. The effect of each factor on differentiation to chondrocytes was examined, with neutralizing antibody for human activin A (product of R&D Systems, Inc., trade name: Human/Mouse/Rat Activin A βA subunit Antibody), follistatin (product of R&D Systems, Inc., trade name: Recombinant Human Follistatin 315 as 30-344), follistatin-like 3 (product of R&D Systems, Inc., trade name: Recombinant Human Follistatin-related Gene Protein/FLRG), ACVR2A-Fc chimeric protein (product of R&D Systems, Inc., trade name: Recombinant Human Activin RIIA Fc Chimera (CHO)), or ACVR2B-Fc chimeric protein (product of R&D Systems, Inc., trade name: Recombinant Human Activin RIIB Fc Chimera), in the copresence of 30 ng/mL of human activin A. The ACVR2A-Fc chimeric protein is a fusion protein in which a polypeptide fragment having the amino acid sequence of positions 20 to 134 of the amino acid sequence listed as SEQ ID NO: 12, and the Fc region of the human-derived antibody, are bonded via a linker sequence (Ile-Glu-Gly-Arg-Met-Asp). The ACVR2B-Fc chimeric protein is a fusion protein in which a polypeptide fragment having the amino acid sequence of positions 19 to 134 of the amino acid sequence listed as SEQ ID NO: 14, and the Fc region of the human-derived antibody, are bonded via a linker sequence (Ile-Glu-Gly-Arg-Met-Asp). The extent of differentiation to chondrocytes was evaluated by Alcian blue staining and sulfated glycosaminoglycan assay, similar to Example 3. The results are shown in FIG. 6. In FIG. 6(B), the bar graph indicates the mean values for each treated group, and the error bars represent S.D.

(Results)

As shown in FIG. 6, the neutralizing antibody for human activin A (anti-activin antibody) follistatin, follistatin-like 3, ACVR2A-Fc chimeric protein and ACVR2B-Fc chimeric protein all inhibited differentiation of FOP patient derived cells to chondrocytes by 30 ng/mL human activin A (ACVR2B-Fc 100 ng/mL P<0.05, anti-activin antibody 100 ng/mL P<0.01, and P<0.001 for all other treatments, Dunnett's multiple comparisons t test with respect to activin-treated group).

Example 6: Effect by Inhibition of Activin Expression (Method)

Figure 7:
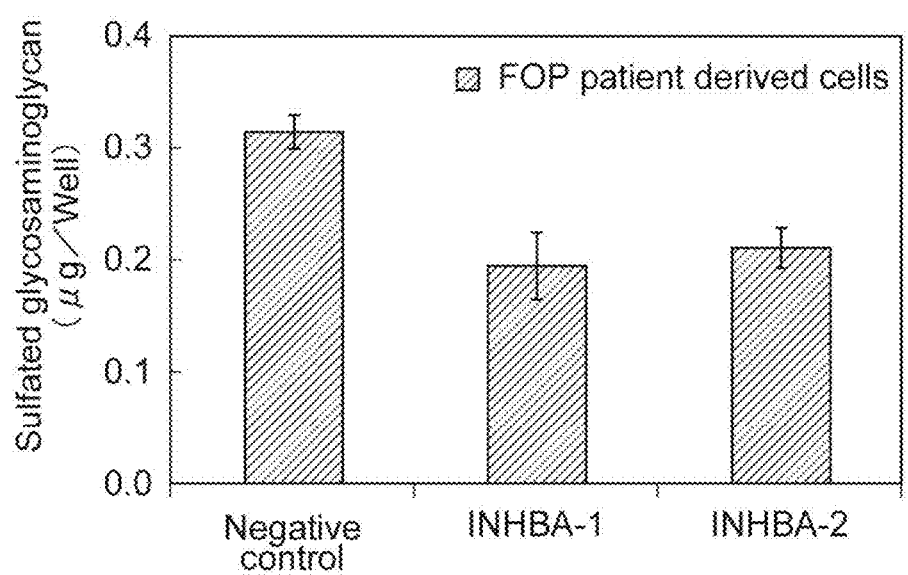
FIG. 7 is a graph showing amounts of sulfated glycosaminoglycan in chondrocytes differentiated from FOP patient derived cells.

Patient iPS cell line-derived mesenchymal stem cell-like cells were prepared by the same method as Example 1. By the same method as in Example 4, FOP patient derived cells were transfected with siRNA for the inhibin βA chain gene, as a polypeptide chain composing activin, to suppress activin expression. The siRNA used for knockdown was siRNA purchased from Applied Biosystems, having two different sequences (INHBA-1 and INHBA-2) (Catalog Nos. S7434 and S7435). This was followed by differentiation to chondrocytes in the same manner as Example 3. The extent of differentiation to chondrocytes was evaluated by sulfated glycosaminoglycan assay, similar to Example 3. The results are shown in FIG. 7. In FIG. 7, "negative control" indicates FOP patient derived cells transfected with negative control siRNA that does not suppress expression of any gene (product of Life Technologies Corp., Catalog No.: 4390843). The bar graph indicates the mean values for each treated group, and the error bars represent S.D.

(Results)

As shown in FIG. 7, when activin expression was suppressed by knockdown of gene expression of the inhibin βA chain, differentiation of FOP patient derived cells to chondrocytes was inhibited (P<0.001 for both siRNAs, Dunnett's multiple comparisons t test).

Example 7: Evaluation of Transcription Activity Via Each Mutant ACVR1

(Method)

Figure 8:
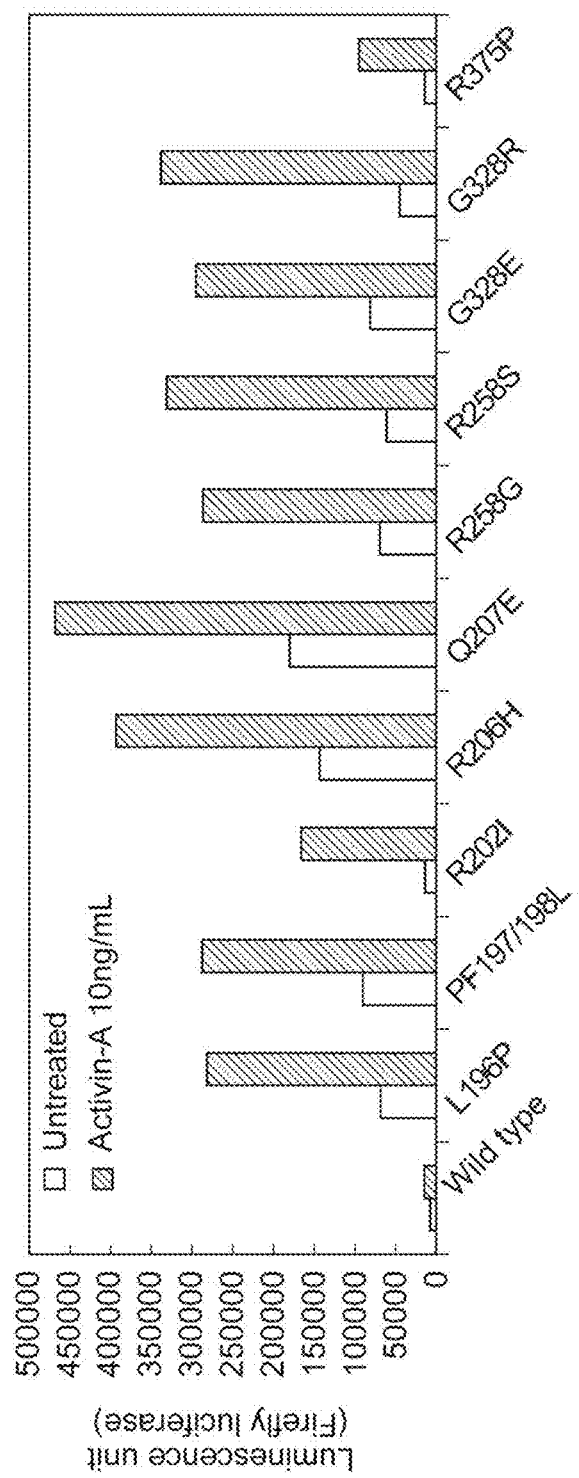
FIG. 8 is a graph showing luminescence unit deriving from expression of a luciferase reporter gene in U2OS cells expressing the gene for wild type ACVR1 or mutant ACVR1.

A Firefly luciferase reporter plasmid having the promoter region of the ID1 gene, as a typical downstream gene of BMP (Genes Cells. 2002 September; 7(9):949-60), was mixed with a plasmid including different mutant ACVR1 genes reported to elicit FOP, and FuGene HD was used on U2OS cells for transfection. At 1 hour after transfection, human activin A (final concentration: 10 ng/mL) was added and the transfected cells were cultured for 20 hours. Next, the luciferase activity was measured according to the protocol provided with a Bright-Glo Luciferase Assay System (product of Promega Corp.). The results are shown in FIG. 8. In FIG. 8, each sample name is listed according to Table 1 above, based on the amino acid mutation of ACVR1.

(Results)

As shown in FIG. 8, treatment with human activin A increased transcription activity via ACVR1 in all of the cells having transfer of a mutant ACVR1 reported to elicit FOP. However, this phenomenon was not observed in cells with transfer of wild type ACVR1. This confirmed that activin A activates the ID1 gene promoter only in cells with transfer of mutant ACVR1 reported to elicit FOP.

Example 8: Evaluation Using Other Activins (Method)

Figure 9:
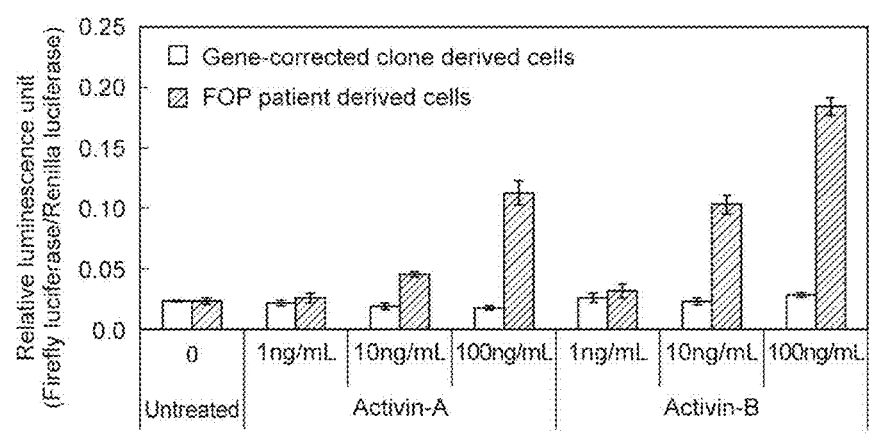
FIG. 9 is a graph showing relative luminescence unit deriving from expression of a luciferase reporter gene, in FOP patient derived cells and gene-corrected clone derived cells.
Figure 9:
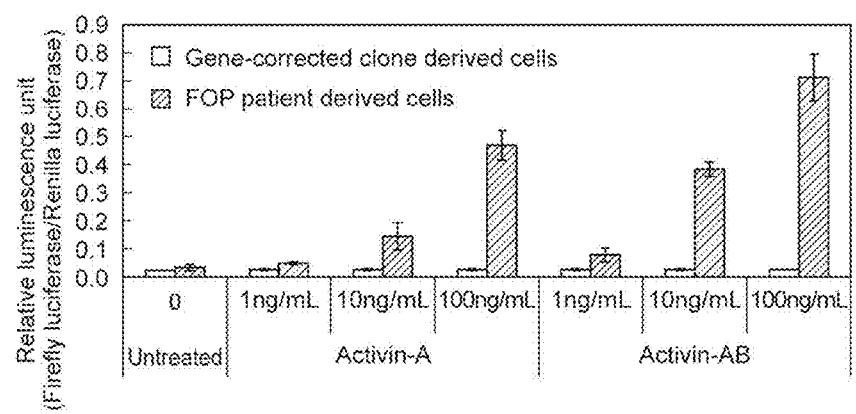

Mesenchymal stem cell-like cells from a patient iPS cell line and a gene-corrected iPS cell clone were each prepared by the same method as Example 1. The cells were transfected with a Firefly luciferase reporter plasmid having the BMP responsive sequence in the promoter region, a plasmid having a nucleic acid sequence coding for *Renilla* luciferase downstream of the CMV promoter, as an internal standard. At 6 hours after transfection, human activin A (product of R&D Systems, Inc., final concentrations: 1 ng/mL, 10 ng/mL, 100 ng/mL) or human activin B (product of R&D Systems, Inc., trade name: Recombinant Human Activin B, final concentrations: 1 ng/mL, 10 ng/mL, 100 ng/mL), or human activin AB (product of R&D Systems, Inc., trade name: Recombinant Human Activin AB, final concentration: 1 ng/mL, 10 ng/mL, 100 ng/mL) was added, and the transfected cells were cultured for 16 hours. Next, the luciferase activity was measured according to the protocol provided with a Dual-Glo Luciferase Assay System (product of Promega Corp.). The results are shown in FIG. 9. In FIG. 9, the bar graph indicates the mean values for each treated group, and the error bars represent S.D.

(Results)

As shown in FIG. 9, similar to treatment with human activin A, treatment with human activin B or human activin AB also significantly increased transcription activity downstream from ACVR1 in FOP patient derived cells (P<0.001 for treatment with 10 ng/mL and 100 ng/mL of activin B and activin AB, Dunnett's multiple comparisons t test with respect to untreated group). This phenomenon was not seen with the gene-corrected clone derived cells. This indicated that activin B and activin AB have similar activity to activin A for FOP patient derived cells.

Example 9: Formation of Three-Dimensional Cartilage Pellets and Transplant Experiment in Mice (Method)

Formation of Three-Dimensional Cartilage Pellets

Mesenchymal stem cell-like cells from a patient iPS cell line and a gene-corrected iPS cell clone were each prepared by the same method as Example 1. The mesenchymal stem cell-like cells were transferred to a 15 mL tube, and chondrocyte pellets were formed by centrifugal separation (1200 rpm×5 min). Culturing was conducted for 21 days as pellets, in the copresence of 100 ng/mL of human activin A under the same medium conditions as Example 3 to prepare three-dimensional cartilage pellets (hereunder also referred to as "cartilage pellets") (photograph (a) of FIG. 10).

Transplant Experiment of Three-Dimensional Cartilage Pellets into Mice

The three-dimensional cartilage pellets obtained by the method described above were subcutaneously transplanted into the dorsal sides of immune-deficient mice (NOD-SCID mice). The transplanted mice were then observed by X-ray image analysis over a 4-week period (photograph (b) in FIG. 10). Ten mice were used for the transplantation. Cartilage pellets prepared from FOP patient derived cells (FOP patient derived cartilage pellets) were transplanted into the right side of each mouse, and cartilage pellets prepared from gene-corrected clone derived cells (gene-corrected clone derived cartilage pellets) were transplanted into the left side. At 4 weeks after transplantation, micro-computed tomography analysis (μCT analysis) was conducted (photograph (c) in FIG. 10). The heterotopically formed osteocartilage masses were then recovered and fixed with 4% paraformaldehyde, and analysis was conducted by tissue staining (HE staining, Alcian blue staining, von Kossa staining) (photograph (d) in FIG. 10).

(Results)

Figure 10:
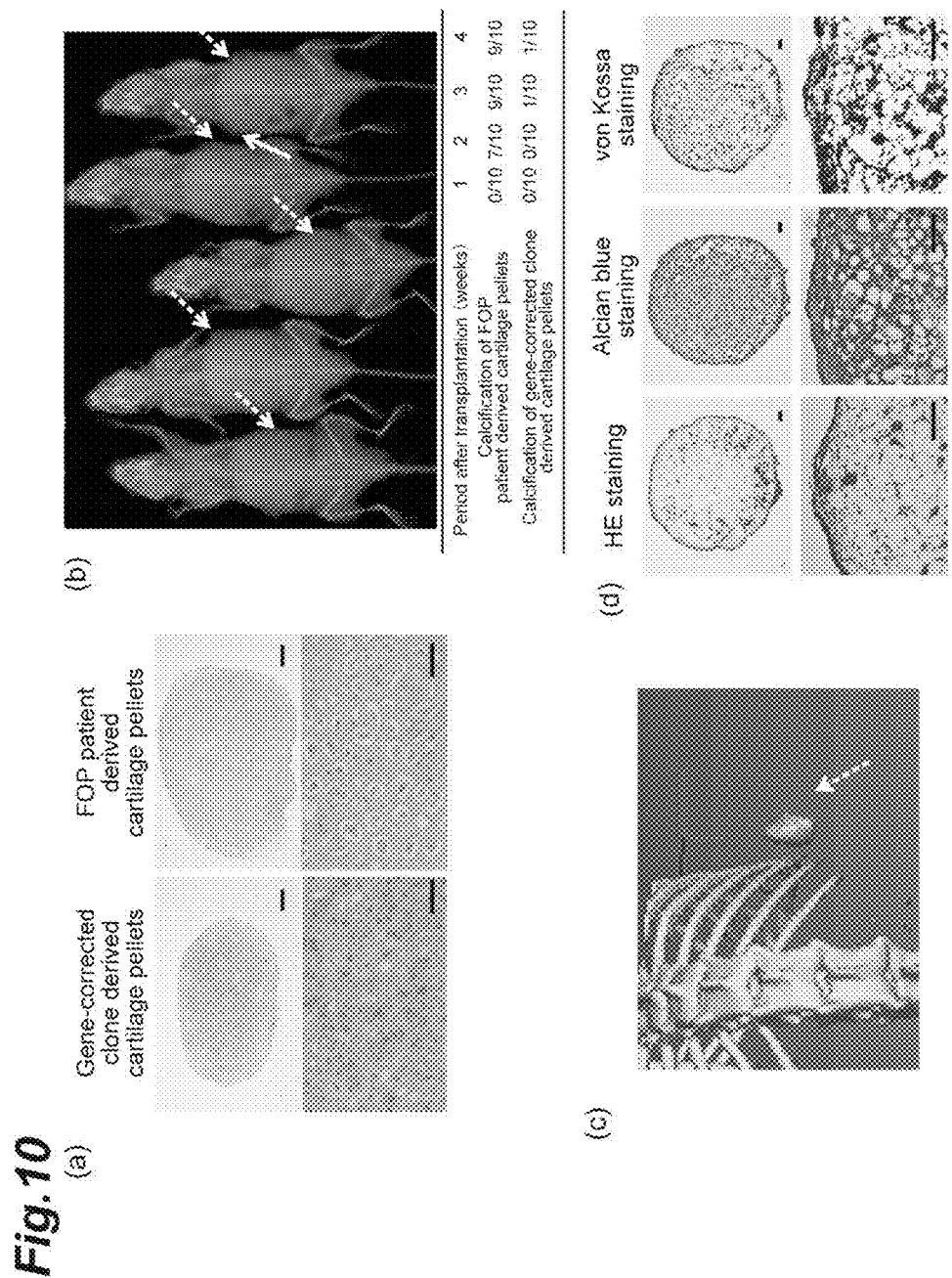
FIG. 10 is a photograph showing the results of a transplant experiment of FOP patient derived cartilage pellets and gene-corrected clone derived cartilage pellets, into mice.

Photographs (a) of the prepared cartilage pellets are shown in FIG. 10. The FOP patient derived cartilage pellets had larger sizes than the gene-corrected clone derived cartilage pellets, and more matured chondrocytes were observed.

Photograph (b) of an X-ray image of mice at 4 weeks after transplantation is shown FIG. 10. The white broken line arrows indicate sites of calcification produced at the locations where the FOP patient derived cartilage pellets were transplanted. The white solid line arrow indicates a site of calcification produced at the location where the gene-corrected clone derived cartilage pellets were transplanted. Heterotopic calcification was observed in 7 of the 10 mice by the second week and in 9 by the third week, at the sites where the FOP patient derived cartilage pellets had been transplanted. On the other hand, heterotopic calcification was observed only in one mouse by the third week, at the site where the gene-corrected clone derived cartilage pellets had been transplanted.

FIG. 10 shows a μCT analysis photograph (photograph (c)) of a site of heterotopic calcification (white broken line arrow) occurring by transplantation of FOP cell derived cartilage pellets. Also, photograph (d) in FIG. 10 shows tissue staining of heterotopically formed osteocartilage masses in mice in which the FOP patient derived cartilage pellets had been transplanted. In all of the analyses, heterotopic calcification was confirmed in all of the transplant sites by transplantation of FOP patient derived cartilage pellets into mice.

INDUSTRIAL APPLICABILITY

FOP is a disease for which no method of confirmed effective clinical treatment exists. The present invention provides an effective prophylactic agent and/or therapeutic agent that suppresses the cardinal symptom of flare-up, and/or abnormal formation and growth of cartilage or bone, in FOP. More specifically, it provides a prophylactic agent and a method of prevention, as well as a therapeutic agent and method of treatment, which suppresses flare-up as the cardinal symptom of FOP, and/or abnormal formation and growth of cartilage or bone, by inhibiting interaction between activin and ACVR1 or suppressing expression of activin.

[Sequence Listing]

The invention claimed is:

1. A method of suppressing onset of flare-up or ectopic ossification or treating fibrodysplasia ossificans progressiva, including administering, to a mammal, an effective dose of a binding inhibitor that inhibits interaction between activin and activin A receptor type I (ACVR1), wherein the binding inhibitor is selected from the group consisting of:
   (a) a polypeptide fragment of activin receptor or a fusion protein of the polypeptide fragment and a carrier protein, wherein the polypeptide fragment is (i) a membrane receptor comprising the extracellular ligand-binding domain and transmembrane region, or (ii) a soluble receptor comprising the entire extracellular domain of a receptor, or a portion of the extracellular domain including the ligand-binding domain, and
   (b) an antibody for activin and an activin binding fragment thereof.

2. The method according to claim 1, wherein the mammal is a human.

3. The method according to claim 2, wherein the human has an amino acid mutation in ACVR1.

4. The method according to claim 3, wherein the amino acid mutation includes an amino acid mutation in the GS domain or kinase domain of the ACVR1.

5. The method according to claim 4, wherein the amino acid mutation in the GS domain or kinase domain includes at least one amino acid mutation selected from the group consisting of amino acid mutations in which the 196th amino acid residue is proline, amino acid mutations in which the 197th amino acid residue is leucine and the 198th amino acid is deleted, amino acid mutations in which the 202nd amino acid residue is isoleucine, amino acid mutations in which the 206th amino acid residue is histidine, amino acid mutations in which the 207th amino acid residue is glutamic acid, amino acid mutations in which the 258th amino acid residue is glycine or serine, amino acid mutations in which the 325th amino acid residue is alanine, amino acid mutations in which the 328th amino acid residue is glutamic acid, arginine or tryptophan, amino acid mutations in which the 356th amino acid residue is aspartic acid, and amino acid mutations in which the 375th amino acid residue is proline, in the amino acid sequence of SEQ ID NO: 10.

6. The method according to claim 4, including an amino acid mutation in the ACVR1 GS domain, the amino acid mutation in the GS domain including an amino acid mutation in which the 206th amino acid residue of the amino acid sequence of SEQ ID NO: 10 is histidine.

7. The method according to claim 1, wherein the activin receptor of the binding inhibitor (a) is ACVR2A or ACVR2B.

8. The method according to claim 7, wherein the activin receptor of the binding inhibitor (a) is ACVR2A.

9. The method according to claim 8, wherein the ACVR2A includes a protein including the amino acid sequence of SEQ ID NO: 12.

10. The method according to claim 1, wherein the polypeptide fragment has an amino acid sequence corresponding to amino acid positions 20 to 135 of the amino acid sequence of SEQ ID NO: 12.

11. The method according to claim 7, wherein the activin receptor of the binding inhibitor (a) is ACVR2B.

12. The method according to claim 11, wherein ACVR2B includes a protein including the amino acid sequence of SEQ ID NO: 14.

13. The method according to claim 1, wherein the polypeptide fragment has an amino acid sequence corresponding to amino acid positions 19 to 134 of the amino acid sequence of SEQ ID NO: 14.

14. The method according to claim 1, wherein
the binding inhibitor is the fusion protein of the polypeptide fragment and the carrier protein,
the polypeptide fragment is the soluble receptor comprising the entire extracellular domain of ACVR2A, or a portion of its extracellular domain including the ligand-binding domain, and
the carrier protein is a Fc region of a human-derived antibody in which the soluble receptor linked either directly or via a linker sequence with the Fc region.

15. The method according to claim 1, wherein the polypeptide fragment is the soluble receptor consisting of a polypeptide fragment of 100 to 140 amino acid residues having an amino acid sequence corresponding to the extracellular domain of the activin receptor and having the ability to bind with activin.

16. The method according to claim 1, wherein the polypeptide fragment is the soluble receptor consisting of a polypeptide fragment of 100 to 120 amino acid residues having an amino acid sequence corresponding to the extracellular domain of the activin receptor and having the ability to bind with activin.

17. The method according the claim 1, wherein the binding inhibitor is the fusion protein of the polypeptide fragment and the carrier protein, and the carrier protein is an antibody Fc fragment or a modified form of Fc fragment having an amino acid sequence with a deletion, substitution, insertion or addition of one or several amino acids.

18. The method according to claim 1, wherein the binding inhibitor is the fusion protein of the polypeptide fragment and the carrier protein, wherein the polypeptide fragment is the polypeptide fragment comprising an amino acid sequence of positions 20 to 135 of an amino acid sequence listed as SEQ ID NO: 12, or an amino acid sequence of positions 19 to 134 of the amino acid sequence listed as SEQ ID NO: 14, and the carrier protein is a Fc region of human-derived antibody or a modified form of the Fc region having an amino acid sequence with a deletion, substitution, insertion, or addition of one or several amino acids.

19. The method according to claim 18, wherein the fusion protein is a Sotatercept.

20. The method according to claim 1, wherein the antibody for activin is an antibody whose antigen is at least one inhibin β chain selected from the group consisting of the inhibin βA chain, inhibin βB chain, inhibin βC chain and inhibin βE chain.

21. The method according to claim 1, wherein the antibody for activin is an antibody whose antigen is inhibin βA chain or inhibin βB chain.

22. The method according to claim 1, wherein the antibody for activin is a monoclonal antibody.

23. The method according to claim 1, wherein isotype of the antibody is IgG, IgM or IgA.

24. The method according to claim 1, wherein the antibody is selected from the group consisting of chimeric antibody, humanized antibody, fully humanized antibody, single-chain antibody or antibody fused with a protein.

25. The method according to claim 1, wherein the method treats fibrodysplasia ossificans progressiva.

26. The method according to claim 1, wherein the binding inhibitor is the polypeptide fragment of activin receptor or the fusion protein of the polypeptide fragment and a carrier protein, wherein the polypeptide fragment is (i) the membrane receptor comprising the extracellular ligand-binding domain and transmembrane region, or (ii) the soluble receptor comprising the entire extracellular domain of a receptor or a portion of the extracellular domain including the ligand-binding domain.

* * * * *

```
SEQUENCE LISTING

<160> NUMBER OF SEQ ID NOS: 44

<210> SEQ ID NO 1
<211> LENGTH: 2175
<212> TYPE: DNA
<213> ORGANISM: Homo sapiens
<220> FEATURE:
<221> NAME/KEY: CDS
<222> LOCATION: (248)..(1528)

<400> SEQUENCE: 1
agtacagtat aaaacttcac agtgccaata ccatgaagag gagctcagac agctcttacc      60
acatgataca agagccggct ggtggaagag tggggaccag aaagagaatt tgctgaagag     120
gagaaggaaa aaaaaaacac caaaaaaaaa aataaaaaaa tccacacaca caaaaaaacc     180
tgcgcgtgag gggggaggaa aagcagggcc ttttaaaaag gcaatcacaa caacttttgc     240 tgccagg atg ccc ttg ctt tgg ctg aga gga ttt ctg ttg gca agt tgc     289
        Met Pro Leu Leu Trp Leu Arg Gly Phe Leu Leu Ala Ser Cys
```

```
                 1               5                    10
tgg att ata gtg agg agt tcc ccc acc cca gga tcc gag ggg cac agc        337
Trp Ile Ile Val Arg Ser Ser Pro Thr Pro Gly Ser Glu Gly His Ser
 15              20                   25                  30 gcg gcc ccc gac tgt ccg tcc tgt gcg ctg gcc gcc ctc cca aag gat        385
Ala Ala Pro Asp Cys Pro Ser Cys Ala Leu Ala Ala Leu Pro Lys Asp
                 35                  40                  45 gta ccc aac tct cag cca gag atg gtg gag gcc gtc aag aag cac att        433
Val Pro Asn Ser Gln Pro Glu Met Val Glu Ala Val Lys Lys His Ile
             50                  55                  60 tta aac atg ctg cac ttg aag aag aga ccc gat gtc acc cag ccg gta        481
Leu Asn Met Leu His Leu Lys Lys Arg Pro Asp Val Thr Gln Pro Val
         65                  70                  75 ccc aag gcg gcg ctt ctg aac gcg atc aga aag ctt cat gtg ggc aaa        529
Pro Lys Ala Ala Leu Leu Asn Ala Ile Arg Lys Leu His Val Gly Lys
     80                  85                  90 gtc ggg gag aac ggg tat gtg gag ata gag gat gac att gga agg agg        577
Val Gly Glu Asn Gly Tyr Val Glu Ile Glu Asp Asp Ile Gly Arg Arg
 95                 100                 105                 110 gca gaa atg aat gaa ctt atg gag cag acc tcg gag atc atc acg ttt        625
Ala Glu Met Asn Glu Leu Met Glu Gln Thr Ser Glu Ile Ile Thr Phe
                115                 120                 125 gcc gag tca gga aca gcc agg aag acg ctg cac ttc gag att tcc aag        673
Ala Glu Ser Gly Thr Ala Arg Lys Thr Leu His Phe Glu Ile Ser Lys
            130                 135                 140 gaa ggc agt gac ctg tca gtg gtg gag cgt gca gaa gtc tgg ctc ttc        721
Glu Gly Ser Asp Leu Ser Val Val Glu Arg Ala Glu Val Trp Leu Phe
        145                 150                 155 cta aaa gtc ccc aag gcc aac agg acc agg acc aaa gtc acc atc cgc        769
Leu Lys Val Pro Lys Ala Asn Arg Thr Arg Thr Lys Val Thr Ile Arg
    160                 165                 170 ctc ttc cag cag cag aag cac ccg cag ggc agc ttg gac aca ggg gaa        817
Leu Phe Gln Gln Gln Lys His Pro Gln Gly Ser Leu Asp Thr Gly Glu
175                 180                 185                 190 gag gcc gag gaa gtg ggc tta aag ggg gag agg agt gaa ctg ttg ctc        865
Glu Ala Glu Glu Val Gly Leu Lys Gly Glu Arg Ser Glu Leu Leu Leu
                195                 200                 205 tct gaa aaa gta gta gac gct cgg aag agc acc tgg cat gtc ttc cct        913
Ser Glu Lys Val Val Asp Ala Arg Lys Ser Thr Trp His Val Phe Pro
            210                 215                 220 gtc tcc agc agc atc cag cgg ttg ctg gac cag ggc aag agc tcc ctg        961
Val Ser Ser Ser Ile Gln Arg Leu Leu Asp Gln Gly Lys Ser Ser Leu
        225                 230                 235 gac gtt cgg att gcc tgt gag cag tgc cag gag agt ggc gcc agc ttg       1009
Asp Val Arg Ile Ala Cys Glu Gln Cys Gln Glu Ser Gly Ala Ser Leu
    240                 245                 250 gtt ctc ctg ggc aag aag aag aaa gaa gag gag ggg gaa ggg aaa           1057
Val Leu Leu Gly Lys Lys Lys Lys Glu Glu Glu Gly Glu Gly Lys
255                 260                 265                 270 aag aag ggc gga ggt gaa ggt ggg gca gga gca gat gag gaa aag gag       1105
Lys Lys Gly Gly Gly Glu Gly Gly Ala Gly Ala Asp Glu Glu Lys Glu
                275                 280                 285 cag tcg cac aga cct ttc ctc atg ctg cag gcc cgg cag tct gaa gac       1153
Gln Ser His Arg Pro Phe Leu Met Leu Gln Ala Arg Gln Ser Glu Asp
            290                 295                 300 cac cct cat cgc cgg cgt cgg cgg ggc ttg gag tgt gat ggc aag gtc       1201
His Pro His Arg Arg Arg Arg Gly Leu Glu Cys Asp Gly Lys Val
        305                 310                 315 aac atc tgc tgt aag aaa cag ttc ttt gtc agt ttc aag gac atc ggc       1249
```

-continued

```
                Asn Ile Cys Cys Lys Lys Gln Phe Phe Val Ser Phe Lys Asp Ile Gly
                    320                 325                 330 tgg aat gac tgg atc att gct ccc tct ggc tat cat gcc aac tac tgc           1297
Trp Asn Asp Trp Ile Ile Ala Pro Ser Gly Tyr His Ala Asn Tyr Cys
335                 340                 345                 350 gag ggt gag tgc ccg agc cat ata gca ggc acg tcc ggg tcc tca ctg           1345
Glu Gly Glu Cys Pro Ser His Ile Ala Gly Thr Ser Gly Ser Ser Leu
                355                 360                 365 tcc ttc cac tca aca gtc atc aac cac tac cgc atg cgg ggc cat agc           1393
Ser Phe His Ser Thr Val Ile Asn His Tyr Arg Met Arg Gly His Ser
            370                 375                 380 ccc ttt gcc aac ctc aaa tcg tgc tgt gtg ccc acc aag ctg aga ccc           1441
Pro Phe Ala Asn Leu Lys Ser Cys Cys Val Pro Thr Lys Leu Arg Pro
        385                 390                 395 atg tcc atg ttg tac tat gat gat ggt caa aac atc atc aaa aag gac           1489
Met Ser Met Leu Tyr Tyr Asp Asp Gly Gln Asn Ile Ile Lys Lys Asp
    400                 405                 410 att cag aac atg atc gtg gag gag tgt ggg tgc tca tag agttgcccag            1538
Ile Gln Asn Met Ile Val Glu Glu Cys Gly Cys Ser
415                 420                 425 cccagggga aagggagcaa gagttgtcca gagaagacag tggcaaaatg aagaaatttt          1598
taaggtttct gagttaacca gaaaataga aattaaaaac aaaacaaaaa aaaaaacaaa          1658
aaaaaacaaa agtaaattaa aaacaaaacc tgatgaaaca gatgaaggaa gatgtggaaa         1718
aaatccttag ccagggctca gagatgaagc agtgaaagag acaggaattg ggagggaaag         1778
ggagaatggt gtacccttta tttcttctga aatcacactg atgacatcag ttgtttaaac         1838
ggggtattgt cctttccccc cttgaggttc ccttgtgagc cttgaatcaa ccaatctagt         1898
ctgcagtagt gtggactaga acaacccaaa tagcatctag aaagccatga gtttgaaagg         1958
gcccatcaca ggcactttcc tacccaatta cccaggtcat aaggtatgtc tgtgtgacac         2018
ttatctctgt gtatatcagc atacacacac acacacacac acacacacac acacacaggc        2078
atttccacac attacatata tacacatact ggtaaaagaa caatcgtgtg caggtggtca        2138
cacttccttt ttctgtacca cttttgcaac aaaacaa                                 2175
```

<210> SEQ ID NO 2
<211> LENGTH: 426
<212> TYPE: PRT
<213> ORGANISM: Homo sapiens

<400> SEQUENCE: 2

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
                100                 105                 110

Met Asn Glu Leu Met Glu Gln Thr Ser Glu Ile Ile Thr Phe Ala Glu
```

```
            115                 120                 125
Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Glu Glu Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
        355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 3
<211> LENGTH: 3218
<212> TYPE: DNA
<213> ORGANISM: Homo sapiens
<220> FEATURE:
<221> NAME/KEY: CDS
<222> LOCATION: (47)..(1270)

<400> SEQUENCE: 3
actcggctcg cctcgcggcg ggcgccctcg tcgccagcgg cgcacc atg gac ggg      55
                                                 Met Asp Gly
                                                   1 ctg ccc ggt cgg gcg ctg ggg gcc gcc tgc ctt ctg ctg ctg gcg gcc    103
Leu Pro Gly Arg Ala Leu Gly Ala Ala Cys Leu Leu Leu Leu Ala Ala
  5                  10                  15 ggc tgg ctg ggg cct gag gcc tgg ggc tca ccc acg ccc ccg ccg acg    151
```

| | | | | | | | | | | | | | | | |
|---|---|---|---|---|---|---|---|---|---|---|---|---|---|---|---|
|Gly|Trp|Leu|Gly|Pro|Glu|Ala|Trp|Gly|Ser|Pro|Thr|Pro|Pro|Thr| |
|20| | | |25| | | |30| | | |35| | | |

| cct | gcc | gcg | ccg | ccg | cca | ccc | ccg | cca | ccc | gga | tcc | ccg | ggt | ggc | tcg | 199 |
|---|---|---|---|---|---|---|---|---|---|---|---|---|---|---|---|---|
| Pro | Ala | Ala | Pro | Pro | Pro | Pro | Pro | Pro | Pro | Gly | Ser | Pro | Gly | Gly | Ser | |
| | | | 40 | | | | | 45 | | | | | | 50 | | |

| cag | gac | acc | tgt | acg | tcg | tgc | ggc | ggc | ttc | cgg | cgg | cca | gag | gag | ctc | 247 |
|---|---|---|---|---|---|---|---|---|---|---|---|---|---|---|---|---|
| Gln | Asp | Thr | Cys | Thr | Ser | Cys | Gly | Gly | Phe | Arg | Arg | Pro | Glu | Glu | Leu | |
| | | | 55 | | | | | 60 | | | | | 65 | | | |

| ggc | cga | gtg | gac | ggc | gac | ttc | ctg | gag | gcg | gtg | aag | cgg | cac | atc | ttg | 295 |
|---|---|---|---|---|---|---|---|---|---|---|---|---|---|---|---|---|
| Gly | Arg | Val | Asp | Gly | Asp | Phe | Leu | Glu | Ala | Val | Lys | Arg | His | Ile | Leu | |
| | | | 70 | | | | | 75 | | | | | 80 | | | |

| agc | cgc | ctg | cag | atg | cgg | ggc | cgg | ccc | aac | atc | acg | cac | gcc | gtg | cct | 343 |
|---|---|---|---|---|---|---|---|---|---|---|---|---|---|---|---|---|
| Ser | Arg | Leu | Gln | Met | Arg | Gly | Arg | Pro | Asn | Ile | Thr | His | Ala | Val | Pro | |
| | | 85 | | | | | 90 | | | | | 95 | | | | |

| aag | gcc | gcc | atg | gtc | acg | gcc | ctg | cgc | aag | ctg | cac | gcg | ggc | aag | gtg | 391 |
|---|---|---|---|---|---|---|---|---|---|---|---|---|---|---|---|---|
| Lys | Ala | Ala | Met | Val | Thr | Ala | Leu | Arg | Lys | Leu | His | Ala | Gly | Lys | Val | |
| 100 | | | | | 105 | | | | | 110 | | | | | 115 | |

| cgc | gag | gac | ggc | cgc | gtg | gag | atc | ccg | cac | ctc | gac | ggc | cac | gcc | agc | 439 |
|---|---|---|---|---|---|---|---|---|---|---|---|---|---|---|---|---|
| Arg | Glu | Asp | Gly | Arg | Val | Glu | Ile | Pro | His | Leu | Asp | Gly | His | Ala | Ser | |
| | | | 120 | | | | | 125 | | | | | 130 | | | |

| ccg | ggc | gcc | gac | ggc | cag | gag | cgc | gtt | tcc | gaa | atc | atc | agc | ttc | gcc | 487 |
|---|---|---|---|---|---|---|---|---|---|---|---|---|---|---|---|---|
| Pro | Gly | Ala | Asp | Gly | Gln | Glu | Arg | Val | Ser | Glu | Ile | Ile | Ser | Phe | Ala | |
| | | | 135 | | | | | 140 | | | | | 145 | | | |

| gag | aca | gat | ggc | ctc | gcc | tcc | tcc | cgg | gtc | cgc | cta | tac | ttc | ttc | atc | 535 |
|---|---|---|---|---|---|---|---|---|---|---|---|---|---|---|---|---|
| Glu | Thr | Asp | Gly | Leu | Ala | Ser | Ser | Arg | Val | Arg | Leu | Tyr | Phe | Phe | Ile | |
| | | 150 | | | | | 155 | | | | | 160 | | | | |

| tcc | aac | gaa | ggc | aac | cag | aac | ctg | ttt | gtg | gtc | cag | gcc | agc | ctg | tgg | 583 |
|---|---|---|---|---|---|---|---|---|---|---|---|---|---|---|---|---|
| Ser | Asn | Glu | Gly | Asn | Gln | Asn | Leu | Phe | Val | Val | Gln | Ala | Ser | Leu | Trp | |
| | 165 | | | | | 170 | | | | | 175 | | | | | |

| ctt | tac | ctg | aaa | ctc | ctg | ccc | tac | gtc | ctg | gag | aag | ggc | agc | cgg | cgg | 631 |
|---|---|---|---|---|---|---|---|---|---|---|---|---|---|---|---|---|
| Leu | Tyr | Leu | Lys | Leu | Leu | Pro | Tyr | Val | Leu | Glu | Lys | Gly | Ser | Arg | Arg | |
| 180 | | | | | 185 | | | | | 190 | | | | | 195 | |

| aag | gtg | cgg | gtc | aaa | gtg | tac | ttc | cag | gag | cag | ggc | cac | ggt | gac | agg | 679 |
|---|---|---|---|---|---|---|---|---|---|---|---|---|---|---|---|---|
| Lys | Val | Arg | Val | Lys | Val | Tyr | Phe | Gln | Glu | Gln | Gly | His | Gly | Asp | Arg | |
| | | | 200 | | | | | 205 | | | | | 210 | | | |

| tgg | aac | atg | gtg | gag | aag | agg | gtg | gac | ctc | aag | cgc | agc | ggc | tgg | cat | 727 |
|---|---|---|---|---|---|---|---|---|---|---|---|---|---|---|---|---|
| Trp | Asn | Met | Val | Glu | Lys | Arg | Val | Asp | Leu | Lys | Arg | Ser | Gly | Trp | His | |
| | | | 215 | | | | | 220 | | | | | 225 | | | |

| acc | ttc | cca | ctc | acg | gag | gcc | atc | cag | gcc | ttg | ttt | gag | cgg | ggc | gag | 775 |
|---|---|---|---|---|---|---|---|---|---|---|---|---|---|---|---|---|
| Thr | Phe | Pro | Leu | Thr | Glu | Ala | Ile | Gln | Ala | Leu | Phe | Glu | Arg | Gly | Glu | |
| | | 230 | | | | | 235 | | | | | 240 | | | | |

| cgg | cga | ctc | aac | cta | gac | gtg | cag | tgt | gac | agc | tgc | cag | gag | ctg | gcc | 823 |
|---|---|---|---|---|---|---|---|---|---|---|---|---|---|---|---|---|
| Arg | Arg | Leu | Asn | Leu | Asp | Val | Gln | Cys | Asp | Ser | Cys | Gln | Glu | Leu | Ala | |
| | 245 | | | | | 250 | | | | | 255 | | | | | |

| gtg | gtg | ccg | gtg | ttc | gtg | gac | cca | ggc | gaa | gag | tcg | cac | cgg | ccc | ttt | 871 |
|---|---|---|---|---|---|---|---|---|---|---|---|---|---|---|---|---|
| Val | Val | Pro | Val | Phe | Val | Asp | Pro | Gly | Glu | Glu | Ser | His | Arg | Pro | Phe | |
| 260 | | | | | 265 | | | | | 270 | | | | | 275 | |

| gtg | gtg | gtg | cag | gct | cgg | ctg | ggc | gac | agc | agg | cac | cgc | att | cgc | aag | 919 |
|---|---|---|---|---|---|---|---|---|---|---|---|---|---|---|---|---|
| Val | Val | Val | Gln | Ala | Arg | Leu | Gly | Asp | Ser | Arg | His | Arg | Ile | Arg | Lys | |
| | | | 280 | | | | | 285 | | | | | 290 | | | |

| cga | ggc | ctg | gag | tgc | gat | ggc | cgg | acc | aac | ctc | tgt | tgc | agg | caa | cag | 967 |
|---|---|---|---|---|---|---|---|---|---|---|---|---|---|---|---|---|
| Arg | Gly | Leu | Glu | Cys | Asp | Gly | Arg | Thr | Asn | Leu | Cys | Cys | Arg | Gln | Gln | |
| | | 295 | | | | | 300 | | | | | 305 | | | | |

| ttc | ttc | att | gac | ttc | cgc | ctc | atc | ggc | tgg | aac | gac | tgg | atc | ata | gca | 1015 |
|---|---|---|---|---|---|---|---|---|---|---|---|---|---|---|---|---|
| Phe | Phe | Ile | Asp | Phe | Arg | Leu | Ile | Gly | Trp | Asn | Asp | Trp | Ile | Ile | Ala | |
| | | | 310 | | | | | 315 | | | | | 320 | | | |

| ccc | acc | ggc | tac | tac | ggg | aac | tac | tgt | gag | ggc | agc | tgc | cca | gcc | tac | 1063 |
|---|---|---|---|---|---|---|---|---|---|---|---|---|---|---|---|---|
| Pro | Thr | Gly | Tyr | Tyr | Gly | Asn | Tyr | Cys | Glu | Gly | Ser | Cys | Pro | Ala | Tyr | |
| | 325 | | | | | 330 | | | | | 335 | | | | | |

```
ctg gca ggg gtc ccc ggc tct gcc tcc tcc ttc cac acg gct gtg gtg     1111
Leu Ala Gly Val Pro Gly Ser Ala Ser Ser Phe His Thr Ala Val Val
340             345                 350                 355 aac cag tac cgc atg cgg ggt ctg aac ccc ggc acg gtg aac tcc tgc     1159
Asn Gln Tyr Arg Met Arg Gly Leu Asn Pro Gly Thr Val Asn Ser Cys
            360                 365                 370 tgc att ccc acc aag ctg agc acc atg tcc atg ctg tac ttc gat gat     1207
Cys Ile Pro Thr Lys Leu Ser Thr Met Ser Met Leu Tyr Phe Asp Asp
        375                 380                 385 gag tac aac atc gtc aag cgg gac gtg ccc aac atg att gtg gag gag     1255
Glu Tyr Asn Ile Val Lys Arg Asp Val Pro Asn Met Ile Val Glu Glu
    390                 395                 400 tgc ggc tgc gcc tga cagtgcaagg caggggcacg gtggtggggc acggagggca     1310
Cys Gly Cys Ala
    405 gtcccgggtg ggcttcttcc agcccccgcg ggaacggggg tacacggtgg gctgagtaca     1370 gtcattctgt tgggctgtgg agatagtgcc agggtgcggc ctgagatatt tttctacagc     1430 ttcatagagc aaccagtcaa aaccagagcg agaaccctca actgacatga aatactttaa     1490 aatgcacacg tagccacgca cagccagacg catcctgcca cccacacagc agcctccagg     1550 ataccagcaa atggatgcgg tgacaaatgg cagcttagct acaaatgcct gtcagtcgga     1610 gagaatgggg tgagcagcca ccattcccac cagctggccc ggccactctg aattgcgcct     1670 tccgagcaca cataaaagca caagacaga gacgcagaga gagagagaga gccacggaga      1730 ggaaaagcag atgcaggggt ggggagcgca gctcggcgga ggctgcgtgt gccccgtggc     1790 ttttaccagg cctgctctgc ctggctcgat gtctgcttct tccccagcct gggatccttc     1850 gtgcttcaag gcctggggag cctgtccttc catgcccttg tcgagggaaa gagacccaga     1910 aaggacacaa cccgtcagag acctgggagc aggggcaatg accgtttgac tgtttgtggc     1970 ttgggcctct gacatgactt atgtgtgtgt gtgtttttgg ggtggggagg gagggagaga     2030 agaggggggct aaatttgatg ctttaactga tctccaacag ttgacaggtc atccttgcca    2090 gttgtataac tgaaaaagga cttttctacc aggtatgacc ttttaagtga aaatctgaat     2150 tgttctaaat ggaaagaaaa aaagttgcaa tctgtgccct tcattgggga cattcctcta     2210 ggactggttt ggggacgggt gggaatgacc cctaggcaag gggatgagac cgcaggagga     2270 aatggcgggg aggaggcatt cttgaactgc tgaggatggg gggtgtcccc tcagcggagg     2330 ccaagggagg ggagcagcct agttggtctt ggagagatgg ggaaggcttt cagctgattt     2390 gcagaagttg cccatgtggg ccccagccat cagggctggc cgtggacgtg gcccctgccc     2450 actcacctgc ccgcctgccc gcccgcccgc atagcacttg cagacctgcc tgaacgcaca     2510 tgacatagca cttgccgatc tgcgtgtgtc cagaagtggc ccttggccga cgccgaact      2570 cgctcgccct ctagatgtcc aagtgccacg tgaactatgc aatttaaagg gttgacccac     2630 actagacgaa actggactcg tacgactctt tttatatttt ttatacttga aatgaaatcc     2690 tttgcttctt ttttaagcga atgattgctt ttaatgtttg cactgattta gttgcatgat     2750 tagtcagaaa ctgccatttg aaaaaaagtt attttatag cagcaaaaaa aaaaaaaaa       2810 gaatacagtt aaatgtatta tacataattt tggaaccaaa gaggccaaca gatcagtttt     2870 aatttttatta gacggtgagg ccatctgaga tgaggtggac gttctgagca gtcccttgag    2930 tggcctgcca acgtttcagg gtatgaatgg attttgttta ttcggtttga tgtgtctttt     2990 ccatccttac acacccagaa ggtagagtaa aaatgactat gatagaatgc aggtgtgtat     3050 ccttaaatcc tcatctttat gtttatttaa taaagctccc cttagattct gtttcataat     3110
```

```
aatttaaaac caaacaattt tcccatagac ttgctgttaa agtattgtac gtttgtgtac    3170
agtttaagaa aataaaagat tgagtgccac gggaaaaaaa aaaaaaaa                 3218
```

<210> SEQ ID NO 4
<211> LENGTH: 407
<212> TYPE: PRT
<213> ORGANISM: Homo sapiens

<400> SEQUENCE: 4

```
Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Pro Pro Pro Pro Pro Pro Gly Ser Pro
            35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Phe His Thr
            340                 345                 350
```

```
Ala Val Val Asn Gln Tyr Arg Met Arg Gly Leu Asn Pro Gly Thr Val
            355                 360                 365

Asn Ser Cys Cys Ile Pro Thr Lys Leu Ser Thr Met Ser Met Leu Tyr
    370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 5
<211> LENGTH: 3315
<212> TYPE: DNA
<213> ORGANISM: Homo sapiens
<220> FEATURE:
<221> NAME/KEY: CDS
<222> LOCATION: (203)..(1261)

<400> SEQUENCE: 5
```

| | |
|---|---:|
| agattctgcc aagttctacc tgtaactggc ttcattttca agtcagacgt ttggctgctg | 60 |
| ctctgtcccc tgcaacaagg agccatgcca gctggacaca cacttcttcc agggcctctg | 120 |
| gcagccagga cagagttgag accacagctg ttgagaccct gagccctgag tctgtattgc | 180 |
| tcaagaaggg ccttccccag ca atg acc tcc tca ttg ctt ctg gcc ttt ctc | 232 |
|     Met Thr Ser Ser Leu Leu Leu Ala Phe Leu | |
|     1               5                   10 | |
| ctc ctg gct cca acc aca gtg gcc act ccc aga gct ggc ggt cag tgt | 280 |
| Leu Leu Ala Pro Thr Thr Val Ala Thr Pro Arg Ala Gly Gly Gln Cys | |
|             15                  20                  25 | |
| cca gca tgt ggg ggg ccc acc ttg gaa ctg gag agc cag cgg gag ctg | 328 |
| Pro Ala Cys Gly Gly Pro Thr Leu Glu Leu Glu Ser Gln Arg Glu Leu | |
|         30                  35                  40 | |
| ctt ctt gat ctg gcc aag aga agc atc ttg gac aag ctg cac ctc acc | 376 |
| Leu Leu Asp Leu Ala Lys Arg Ser Ile Leu Asp Lys Leu His Leu Thr | |
|     45                  50                  55 | |
| cag cgc cca aca ctg aac cgc cct gtg tcc aga gct gct ttg agg act | 424 |
| Gln Arg Pro Thr Leu Asn Arg Pro Val Ser Arg Ala Ala Leu Arg Thr | |
| 60                  65                  70 | |
| gca ctg cag cac ctc cac ggg gtc cca cag ggg gca ctt cta gag gac | 472 |
| Ala Leu Gln His Leu His Gly Val Pro Gln Gly Ala Leu Leu Glu Asp | |
| 75                  80                  85                  90 | |
| aac agg gaa cag gaa tgt gaa atc atc agc ttt gct gag aca ggc ctc | 520 |
| Asn Arg Glu Gln Glu Cys Glu Ile Ile Ser Phe Ala Glu Thr Gly Leu | |
|                 95                 100                 105 | |
| tcc acc atc aac cag act cgt ctt gat ttt cac ttc tcc tct gat aga | 568 |
| Ser Thr Ile Asn Gln Thr Arg Leu Asp Phe His Phe Ser Ser Asp Arg | |
|             110                 115                 120 | |
| act gct ggt gac agg gag gtc cag cag gcc agt ctc atg ttc ttt gtg | 616 |
| Thr Ala Gly Asp Arg Glu Val Gln Gln Ala Ser Leu Met Phe Phe Val | |
|         125                 130                 135 | |
| cag ctc cct tcc aat acc act tgg acc ttg aaa gtg aga gtc ctt gtg | 664 |
| Gln Leu Pro Ser Asn Thr Thr Trp Thr Leu Lys Val Arg Val Leu Val | |
|     140                 145                 150 | |
| ctg ggt cca cat aat acc aac ctc acc ttg gct act cag tac ctg ctg | 712 |
| Leu Gly Pro His Asn Thr Asn Leu Thr Leu Ala Thr Gln Tyr Leu Leu | |
| 155                 160                 165                 170 | |
| gag gtg gat gcc agt ggc tgg cat caa ctc ccc cta ggg cct gaa gct | 760 |
| Glu Val Asp Ala Ser Gly Trp His Gln Leu Pro Leu Gly Pro Glu Ala | |
|                 175                 180                 185 | |
| caa gct gcc tgc agc cag ggg cac ctg acc ctg gag ctg gta ctt gaa | 808 |
| Gln Ala Ala Cys Ser Gln Gly His Leu Thr Leu Glu Leu Val Leu Glu | |

```
                    190                 195                 200
ggc cag gta gcc cag agc tca gtc atc ctg ggt gga gct gcc cat agg      856
Gly Gln Val Ala Gln Ser Ser Val Ile Leu Gly Gly Ala Ala His Arg
        205                 210                 215 cct ttt gtg gca gcc cgg gtg aga gtt ggg ggc aaa cac cag att cac      904
Pro Phe Val Ala Ala Arg Val Arg Val Gly Gly Lys His Gln Ile His
220                 225                 230 cga cga ggc atc gac tgc caa gga ggg tcc agg atg tgc tgt cga caa      952
Arg Arg Gly Ile Asp Cys Gln Gly Gly Ser Arg Met Cys Cys Arg Gln
235                 240                 245                 250 gag ttt ttt gtg gac ttc cgt gag att ggc tgg cac gac tgg atc atc     1000
Glu Phe Phe Val Asp Phe Arg Glu Ile Gly Trp His Asp Trp Ile Ile
                    255                 260                 265 cag cct gag ggc tac gcc atg aac ttc tgc ata ggg cag tgc cca cta     1048
Gln Pro Glu Gly Tyr Ala Met Asn Phe Cys Ile Gly Gln Cys Pro Leu
                270                 275                 280 cac ata gca ggc atg cct ggt att gct gcc tcc ttt cac act gca gtg     1096
His Ile Ala Gly Met Pro Gly Ile Ala Ala Ser Phe His Thr Ala Val
                285                 290                 295 ctc aat ctt ctc aag gcc aac aca gct gca ggc acc act gga ggg ggc     1144
Leu Asn Leu Leu Lys Ala Asn Thr Ala Ala Gly Thr Thr Gly Gly Gly
300                 305                 310 tca tgc tgt gta ccc acg gcc cgg cgc ccc ctg tct ctg ctc tat tat     1192
Ser Cys Cys Val Pro Thr Ala Arg Arg Pro Leu Ser Leu Leu Tyr Tyr
315                 320                 325                 330 gac agg gac agc aac att gtc aag act gac ata cct gac atg gta gta     1240
Asp Arg Asp Ser Asn Ile Val Lys Thr Asp Ile Pro Asp Met Val Val
                    335                 340                 345 gag gcc tgt ggg tgc agt tag tctatgtgtg gtatgggcag cccaaggttg        1291
Glu Ala Cys Gly Cys Ser
                350 catgggaaaa cacgcccta cagaagtgca cttccttgag aggagggaat gacctcattc     1351
tctgtccaga atgtggactc cctcttcctg agcatcttat ggaaattacc ccacctttga    1411
cttgaagaaa ccttcatcta aagcaagtca ctgtgccatc ttcctgacca ctaccctctt    1471
tcctagggca tagtccatcc cgctagtcca tcccgctagc cccactccag ggactcagac    1531
ccatctccaa ccatgagcaa tgccatctgg ttcccaggca agacaccct tagctcacct     1591
ttaatagacc ccataaccca ctatgccttc ctgtcctttc tactcaatgg tccccactcc    1651
aagatgagtt gacacaaccc cttcccccaa tttttgtgga tctccagaga ggcccttctt    1711
tggattcacc aaagtttaga tcactgctgc caaaataga ggcttaccta ccccctctt     1771
tgttgtgagc ccctgtcctt cttagttgtc caggtgaact actaaagctc tctttgcata    1831
ccttcatcca ttttttgtcc ttctctgcct ttctctatgc ccttaagggc tgacttgcct    1891
gagctctatc acctgagctc ccctgccctc tggcttcctg ctgaggtcag gcatttctt    1951
atccctgttc cctctctgtc taggtgtcat ggttctgtgt aactgtggct attctgtgtc    2011
cctacactac ctggctaccc ccttccatgg ccccagctct gcctacattc tgatataact    2071
gcttcaacac tagggggtcc taaaggcttt ctatcttgct agtccctggg gcctcaacat    2131
ctcatactgg ttcccttaac tctgcctata cctctgtaaa taattccttc actaagttct    2191
cttgatgaag caaaaacaga cagctgaaaa gtcctctatc tcctacaagg ccctaactg    2251
gcacccccaga tgcacagag cctgcctgct tatgctgtag tctgcctact ctgctgtctc    2311
ttcacatggt ctcctcagaa ctgaactatt gtatccatct cacactttat gcctcttctt    2371
tcttaggcac cccgtccctc catccttcca gaaccatctt tgaggtctca tggctaataa    2431
```

```
aaacctaggc tttacctgtt ccctctgtaa tccctccaaa agatgagaca gatctatgct    2491
tggtcatcca gtaaactgac cagctgtggg cacgcaagtg tgggaggcag aggcatgctc    2551
agagctggct gccaggacct ctgacttgcc ttcctttcac ccaccccag tgctccaccc     2611 aggagtcctg cctggaagct ggaatgggca agggctgctg gagtgggaca gggagaagag    2671
gaaggcctgg atgaggagag ggtggcattt gctctgagac tgggtccttt ttagaccttt    2731
gcccgtcctc ccccacatct cctcccttg gctggacagt cctgaaccat gaggtcgata     2791
atgtctgcag cccaaggccg agtttgcgca aacccatgt gttctttggt aaacgtgatg     2851
tctgtgtttg ctcagtttat gacccctcc tatgagggta agaggtccct gaataggaa      2911 ccctagagga gaaagtctga aaaggactgc ctggggact gtaaatctga gcttgagggc     2971
ttcctgagca acccatggaa gttatcccac ctttgacttg aggagacctt catctaagga    3031
gaatctaagg aggccttctg gtgtctcccc cacacatccc cgaccccag atctaacctc     3091 cttcccaatt acagcttagt ctccaggggct aggactgggg taaagcaaag tgagtcattc   3151
acctgggggg gctaaatttt aaggggggtgg tgaacaattt attaatcaag ataggactttt  3211 aatgcaatat tattttaaag tcaaaattaa tgcaaaaaat ccatgatgaa caaaatagcc    3271
tacttttaaa taaaaacagg atcagcatta aaaaaaaaaa aaaa                    3315
```

<210> SEQ ID NO 6
<211> LENGTH: 352
<212> TYPE: PRT
<213> ORGANISM: Homo sapiens

<400> SEQUENCE: 6

```
Met Thr Ser Ser Leu Leu Leu Ala Phe Leu Leu Leu Ala Pro Thr Thr
1               5                   10                  15

Val Ala Thr Pro Arg Ala Gly Gly Gln Cys Pro Ala Cys Gly Gly Pro
            20                  25                  30

Thr Leu Glu Leu Glu Ser Gln Arg Glu Leu Leu Leu Asp Leu Ala Lys
        35                  40                  45

Arg Ser Ile Leu Asp Lys Leu His Leu Thr Gln Arg Pro Thr Leu Asn
    50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
                85                  90                  95

Glu Ile Ile Ser Phe Ala Glu Thr Gly Leu Ser Thr Ile Asn Gln Thr
            100                 105                 110

Arg Leu Asp Phe His Phe Ser Ser Asp Arg Thr Ala Gly Asp Arg Glu
        115                 120                 125

Val Gln Gln Ala Ser Leu Met Phe Phe Val Gln Leu Pro Ser Asn Thr
    130                 135                 140

Thr Trp Thr Leu Lys Val Arg Val Leu Val Leu Gly Pro His Asn Thr
145                 150                 155                 160

Asn Leu Thr Leu Ala Thr Gln Tyr Leu Leu Glu Val Asp Ala Ser Gly
                165                 170                 175

Trp His Gln Leu Pro Leu Gly Pro Glu Ala Gln Ala Ala Cys Ser Gln
            180                 185                 190

Gly His Leu Thr Leu Glu Leu Val Leu Glu Gly Gln Val Ala Gln Ser
        195                 200                 205

Ser Val Ile Leu Gly Gly Ala Ala His Arg Pro Phe Val Ala Ala Arg
```

```
                    210                 215                 220
Val Arg Val Gly Gly Lys His Gln Ile His Arg Arg Gly Ile Asp Cys
225                 230                 235                 240

Gln Gly Gly Ser Arg Met Cys Cys Arg Gln Glu Phe Phe Val Asp Phe
                245                 250                 255

Arg Glu Ile Gly Trp His Asp Trp Ile Ile Gln Pro Glu Gly Tyr Ala
            260                 265                 270

Met Asn Phe Cys Ile Gly Gln Cys Pro Leu His Ile Ala Gly Met Pro
        275                 280                 285

Gly Ile Ala Ala Ser Phe His Thr Ala Val Leu Asn Leu Leu Lys Ala
    290                 295                 300

Asn Thr Ala Ala Gly Thr Thr Gly Gly Gly Ser Cys Cys Val Pro Thr
305                 310                 315                 320

Ala Arg Arg Pro Leu Ser Leu Leu Tyr Tyr Asp Arg Asp Ser Asn Ile
                325                 330                 335

Val Lys Thr Asp Ile Pro Asp Met Val Val Glu Ala Cys Gly Cys Ser
                340                 345                 350

<210> SEQ ID NO 7
<211> LENGTH: 2453
<212> TYPE: DNA
<213> ORGANISM: Homo sapiens
<220> FEATURE:
<221> NAME/KEY: CDS
<222> LOCATION: (225)..(1277)

<400> SEQUENCE: 7
cagacatgag ctgtgagggt caagcacagc tatccatcag atgatctact ttcagccttc    60
ctgagtccca gacaatagaa acaggtggc tgtacccttg ccaagggta ggtgtggcag     120 tggtgtctgc tgtcactgtg ccctcattgg cccccagcaa tcagactcaa cagacggagc   180
aactgccatc cgaggctcct gaaccagggc cattccaccag gagc atg cgg ctc cct   236
                                                 Met Arg Leu Pro
                                                   1 gat gtc cag ctc tgg ctg gtg ctg ctg tgg gca ctg gtg cga gca cag    284
Asp Val Gln Leu Trp Leu Val Leu Leu Trp Ala Leu Val Arg Ala Gln
  5              10                  15                  20 ggg aca ggg tct gtg tgt ccc tcc tgt ggg ggc tcc aaa ctg gca ccc    332
Gly Thr Gly Ser Val Cys Pro Ser Cys Gly Gly Ser Lys Leu Ala Pro
                25                  30                  35 caa gca gaa cga gct ctg gtg ctg gag cta gcc aag cag caa atc ctg    380
Gln Ala Glu Arg Ala Leu Val Leu Glu Leu Ala Lys Gln Gln Ile Leu
            40                  45                  50 gat ggg ttg cac ctg acc agt cgt ccc aga ata act cat cct cca ccc    428
Asp Gly Leu His Leu Thr Ser Arg Pro Arg Ile Thr His Pro Pro Pro
        55                  60                  65 cag gca gcg ctg acc aga gcc ctc cgg aga cta cag cca ggg agt gtg    476
Gln Ala Ala Leu Thr Arg Ala Leu Arg Arg Leu Gln Pro Gly Ser Val
    70                  75                  80 gct cca ggg aat ggg gag gag gtc atc agc ttt gct act gtc aca gac    524
Ala Pro Gly Asn Gly Glu Glu Val Ile Ser Phe Ala Thr Val Thr Asp
85                  90                  95                  100 tcc act tca gcc tac agc tcc ctg ctc act ttt cac ctg tcc act cct    572
Ser Thr Ser Ala Tyr Ser Ser Leu Leu Thr Phe His Leu Ser Thr Pro
                105                 110                 115 cgg tcc cac cac ctg tac cat gcc cgc ctg tgg ctg cac gtg ctc ccc    620
Arg Ser His His Leu Tyr His Ala Arg Leu Trp Leu His Val Leu Pro
            120                 125                 130
```

-continued

| | |
|---|---|
| acc ctt cct ggc act ctt tgc ttg agg atc ttc cga tgg gga cca agg<br>Thr Leu Pro Gly Thr Leu Cys Leu Arg Ile Phe Arg Trp Gly Pro Arg<br>135      140      145 | 668 |
| agg agg cgc caa ggg tcc cgc act ctc ctg gct gag cac cac atc acc<br>Arg Arg Arg Gln Gly Ser Arg Thr Leu Leu Ala Glu His His Ile Thr<br>150      155      160 | 716 |
| aac ctg ggc tgg cat acc tta act ctg ccc tct agt ggc ttg agg ggt<br>Asn Leu Gly Trp His Thr Leu Thr Leu Pro Ser Ser Gly Leu Arg Gly<br>165      170      175      180 | 764 |
| gag aag tct ggt gtc ctg aaa ctg caa cta gac tgc aga ccc cta gaa<br>Glu Lys Ser Gly Val Leu Lys Leu Gln Leu Asp Cys Arg Pro Leu Glu<br>      185      190      195 | 812 |
| ggc aac agc aca gtt act gga caa ccg agg cgg ctc ttg gac aca gca<br>Gly Asn Ser Thr Val Thr Gly Gln Pro Arg Arg Leu Leu Asp Thr Ala<br>      200      205      210 | 860 |
| gga cac cag cag ccc ttc cta gag ctt aag atc cga gcc aat gag cct<br>Gly His Gln Gln Pro Phe Leu Glu Leu Lys Ile Arg Ala Asn Glu Pro<br>215      220      225 | 908 |
| gga gca ggc cgg gcc agg agg agg acc ccc acc tgt gag cct gcg acc<br>Gly Ala Gly Arg Ala Arg Arg Arg Thr Pro Thr Cys Glu Pro Ala Thr<br>230      235      240 | 956 |
| ccc tta tgt tgc agg cga gac cat tac gta gac ttc cag gaa ctg gga<br>Pro Leu Cys Cys Arg Arg Asp His Tyr Val Asp Phe Gln Glu Leu Gly<br>245      250      255      260 | 1004 |
| tgg cgg gac tgg ata ctg cag ccc gag ggg tac cag ctg aat tac tgc<br>Trp Arg Asp Trp Ile Leu Gln Pro Glu Gly Tyr Gln Leu Asn Tyr Cys<br>      265      270      275 | 1052 |
| agt ggg cag tgc cct ccc cac ctg gct ggc agc cca ggc att gct gcc<br>Ser Gly Gln Cys Pro Pro His Leu Ala Gly Ser Pro Gly Ile Ala Ala<br>      280      285      290 | 1100 |
| tct ttc cat tct gcc gtc ttc agc ctc ctc aaa gcc aac aat cct tgg<br>Ser Phe His Ser Ala Val Phe Ser Leu Leu Lys Ala Asn Asn Pro Trp<br>295      300      305 | 1148 |
| cct gcc agt acc tcc tgt tgt gtc cct act gcc cga agg ccc ctc tct<br>Pro Ala Ser Thr Ser Cys Cys Val Pro Thr Ala Arg Arg Pro Leu Ser<br>310      315      320 | 1196 |
| ctc ctc tac ctg gat cat aat ggc aat gtg gtc aag acg gat gtg cca<br>Leu Leu Tyr Leu Asp His Asn Gly Asn Val Val Lys Thr Asp Val Pro<br>325      330      335      340 | 1244 |
| gat atg gtg gtg gag gcc tgt ggc tgc agc tag caagaggacc tggggctttg<br>Asp Met Val Val Glu Ala Cys Gly Cys Ser<br>      345      350 | 1297 |
| gagtgaagag accaagatga agtttcccag gcacagggca tctgtgactg gaggcatcag | 1357 |
| attcctgatc cacaccccaa cccaacaacc acctggcaat atgactcact tgacccctat | 1417 |
| gggacccaaa tgggcacttt cttgtctgag actctggctt attccaggtt ggctgatgtg | 1477 |
| ttgggagatg ggtaaagcgt ttcttctaaa ggggtctacc cagaaagcat gatttcctgc | 1537 |
| cctaagtcct gtgagaagat gtcagggact agggagggag ggaggggaagg cagagaaaaa | 1597 |
| ttacttagcc tctcccaaga tgagaaagtc ctcaagtgag gggaggagga agcagataga | 1657 |
| tggtccagca ggcttgaagc agggtaagca ggctggccca gggtaagggc tgttgaggta | 1717 |
| ccttaaggga aggtcaagag ggagatgggc aaggcgctga gggaggatgc ttaggggacc | 1777 |
| cccagaaaca ggagtcagga aaatgaggca ctaagcctaa gaagttccct ggttttttccc | 1837 |
| agggggacagg acccactggg agacaagcat ttatactttc tttcttctttt tttattttttt | 1897 |
| tgagatcgag tctcgctctg tcaccaggct ggagtgcagt gacacgatct ggctctactg | 1957 |
| caacctccgt ctcctgggtt caagtgattc ttctgcctca gcctcccgag cagctgggat | 2017 |

```
tacaggcgcc cactaatttt tgtattctta gtagaaacga ggtttcaaca tgttggccag    2077
gatggtctca atctcttgac ctcttgatcc acccgacttg gcctcccgaa gtgatgagat    2137
tataggcgtg agccaccgcg cctggcttat actttcttaa taaaaaggag aaagaaaatc    2197
aacaaatgtg agtcataaag aagggttagg gtgatggtcc agagcaacag ttcttcaagt    2257
gtactctgta ggcttctggg aggtcccttt tcagggtgt ccacaaagtc aaagctattt    2317
tcataataat actaacatgt tatttgcctt ttgaattctc attatcttaa aattgtattg    2377
tggagttttc cagaggccgt gtgacatgtg attacatcat ctttctgaca tcattgttaa    2437
aaaaaaaaaa aaaaa                                                    2453
```

<210> SEQ ID NO 8
<211> LENGTH: 350
<212> TYPE: PRT
<213> ORGANISM: Homo sapiens

<400> SEQUENCE: 8

```
Met Arg Leu Pro Asp Val Gln Leu Trp Leu Val Leu Leu Trp Ala Leu
1               5                   10                  15

Val Arg Ala Gln Gly Thr Gly Ser Val Cys Pro Ser Cys Gly Gly Ser
            20                  25                  30

Lys Leu Ala Pro Gln Ala Glu Arg Ala Leu Val Leu Glu Leu Ala Lys
        35                  40                  45

Gln Gln Ile Leu Asp Gly Leu His Leu Thr Ser Arg Pro Arg Ile Thr
    50                  55                  60

His Pro Pro Gln Ala Ala Leu Thr Arg Ala Leu Arg Arg Leu Gln
65                  70                  75                  80

Pro Gly Ser Val Ala Pro Gly Asn Gly Glu Glu Val Ile Ser Phe Ala
                85                  90                  95

Thr Val Thr Asp Ser Thr Ser Ala Tyr Ser Leu Leu Thr Phe His
            100                 105                 110

Leu Ser Thr Pro Arg Ser His His Leu Tyr His Ala Arg Leu Trp Leu
        115                 120                 125

His Val Leu Pro Thr Leu Pro Gly Thr Leu Cys Leu Arg Ile Phe Arg
    130                 135                 140

Trp Gly Pro Arg Arg Arg Gln Gly Ser Arg Thr Leu Leu Ala Glu
145                 150                 155                 160

His His Ile Thr Asn Leu Gly Trp His Thr Leu Thr Leu Pro Ser Ser
                165                 170                 175

Gly Leu Arg Gly Glu Lys Ser Gly Val Leu Lys Leu Gln Leu Asp Cys
            180                 185                 190

Arg Pro Leu Glu Gly Asn Ser Thr Val Thr Gly Gln Pro Arg Arg Leu
        195                 200                 205

Leu Asp Thr Ala Gly His Gln Gln Pro Phe Leu Glu Leu Lys Ile Arg
    210                 215                 220

Ala Asn Glu Pro Gly Ala Gly Arg Ala Arg Arg Thr Pro Thr Cys
225                 230                 235                 240

Glu Pro Ala Thr Pro Leu Cys Cys Arg Arg Asp His Tyr Val Asp Phe
                245                 250                 255

Gln Glu Leu Gly Trp Arg Asp Trp Ile Leu Gln Pro Glu Gly Tyr Gln
            260                 265                 270

Leu Asn Tyr Cys Ser Gly Gln Cys Pro Pro His Leu Ala Gly Ser Pro
        275                 280                 285
```

```
Gly Ile Ala Ala Ser Phe His Ser Ala Val Phe Ser Leu Leu Lys Ala
    290                 295                 300

Asn Asn Pro Trp Pro Ala Ser Thr Ser Cys Cys Val Pro Thr Ala Arg
305                 310                 315                 320

Arg Pro Leu Ser Leu Leu Tyr Leu Asp His Asn Gly Asn Val Val Lys
                325                 330                 335

Thr Asp Val Pro Asp Met Val Val Glu Ala Cys Gly Cys Ser
                340                 345                 350

<210> SEQ ID NO 9
<211> LENGTH: 3062
<212> TYPE: DNA
<213> ORGANISM: Homo sapiens
<220> FEATURE:
<221> NAME/KEY: CDS
<222> LOCATION: (431)..(1960)

<400> SEQUENCE: 9
gaagagatgt gggcctctgg ggccgctgga ttcagtaact tccgtcgggt tctagactgg      60
ctcggctctg tccagtttgt gccagatagt ctcccacccc ctccccaccc ctcctttccc     120
ctggagattt gaacgctgct tgcatgggag aaaagctact tagagaagaa aacgttccac     180
ttagtaacag aagaaaagtc ttggttaaaa agttgtcatg aatttggctt ttggagagag     240
gcagcaagcc tggagcattg gtaagcgtca cactgccaaa gtgagagctg ctggagaact     300
cataatccca ggaacgcctc ttctactctc cgagtacccc agtgaccaga gtgagagaag     360
ctctgaacga gggcacgcgg cttgaaggac tgtgggcaga tgtgaccaag agcctgcatt     420
aagttgtaca atg gta gat gga gtg atg att ctt cct gtg ctt atc atg       469
            Met Val Asp Gly Val Met Ile Leu Pro Val Leu Ile Met
              1               5                  10 att gct ctc ccc tcc cct agt atg gaa gat gag aag ccc aag gtc aac       517
Ile Ala Leu Pro Ser Pro Ser Met Glu Asp Glu Lys Pro Lys Val Asn
 15                  20                  25 ccc aaa ctc tac atg tgt gtg tgt gaa ggt ctc tcc tgc ggt aat gag       565
Pro Lys Leu Tyr Met Cys Val Cys Glu Gly Leu Ser Cys Gly Asn Glu
 30                  35                  40                  45 gac cac tgt gaa ggc cag cag tgc ttt tcc tca ctg agc atc aac gat       613
Asp His Cys Glu Gly Gln Gln Cys Phe Ser Ser Leu Ser Ile Asn Asp
                 50                  55                  60 ggc ttc cac gtc tac cag aaa ggc tgc ttc cag gtt tat gag cag gga       661
Gly Phe His Val Tyr Gln Lys Gly Cys Phe Gln Val Tyr Glu Gln Gly
             65                  70                  75 aag atg acc tgt aag acc ccg ccg tcc cct ggc caa gcc gtg gag tgc       709
Lys Met Thr Cys Lys Thr Pro Pro Ser Pro Gly Gln Ala Val Glu Cys
         80                  85                  90 tgc caa ggg gac tgg tgt aac agg aac atc acg gcc cag ctg ccc act       757
Cys Gln Gly Asp Trp Cys Asn Arg Asn Ile Thr Ala Gln Leu Pro Thr
     95                 100                 105 aaa gga aaa tcc ttc cct gga aca cag aat ttc cac ttg gag gtt ggc       805
Lys Gly Lys Ser Phe Pro Gly Thr Gln Asn Phe His Leu Glu Val Gly
110                 115                 120                 125 ctc att att ctc tct gta gtg ttc gca gta tgt ctt tta gcc tgc ctg       853
Leu Ile Ile Leu Ser Val Val Phe Ala Val Cys Leu Leu Ala Cys Leu
                130                 135                 140 ctg gga gtt gct ctc cga aaa ttt aaa agg cgc aac caa gaa cgc ctc       901
Leu Gly Val Ala Leu Arg Lys Phe Lys Arg Arg Asn Gln Glu Arg Leu
            145                 150                 155 aat ccc cga gac gtg gag tat ggc act atc gaa ggg ctc atc acc acc       949
Asn Pro Arg Asp Val Glu Tyr Gly Thr Ile Glu Gly Leu Ile Thr Thr
```

-continued

```
               160                 165                 170
aat gtt gga gac agc act tta gca gat tta ttg gat cat tcg tgt aca    997
Asn Val Gly Asp Ser Thr Leu Ala Asp Leu Leu Asp His Ser Cys Thr
            175                 180                 185 tca gga agt ggc tct ggt ctt cct ttt ctg gta caa aga aca gtg gct   1045
Ser Gly Ser Gly Ser Gly Leu Pro Phe Leu Val Gln Arg Thr Val Ala
190                 195                 200                 205 cgc cag att aca ctg ttg gag tgt gtc ggg aaa ggc agg tat ggt gag   1093
Arg Gln Ile Thr Leu Leu Glu Cys Val Gly Lys Gly Arg Tyr Gly Glu
                210                 215                 220 gtg tgg agg ggc agc tgg caa ggg gag aat gtt gcc gtg aag atc ttc   1141
Val Trp Arg Gly Ser Trp Gln Gly Glu Asn Val Ala Val Lys Ile Phe
            225                 230                 235 tcc tcc cgt gat gag aag tca tgg ttc agg gaa acg gaa ttg tac aac   1189
Ser Ser Arg Asp Glu Lys Ser Trp Phe Arg Glu Thr Glu Leu Tyr Asn
        240                 245                 250 act gtg atg ctg agg cat gaa aat atc tta ggt ttc att gct tca gac   1237
Thr Val Met Leu Arg His Glu Asn Ile Leu Gly Phe Ile Ala Ser Asp
            255                 260                 265 atg aca tca aga cac tcc agt acc cag ctg tgg tta att aca cat tat   1285
Met Thr Ser Arg His Ser Ser Thr Gln Leu Trp Leu Ile Thr His Tyr
270                 275                 280                 285 cat gaa atg gga tcg ttg tac gac tat ctt cag ctt act act ctg gat   1333
His Glu Met Gly Ser Leu Tyr Asp Tyr Leu Gln Leu Thr Thr Leu Asp
                290                 295                 300 aca gtt agc tgc ctt cga ata gtg ctg tcc ata gct agt ggt ctt gca   1381
Thr Val Ser Cys Leu Arg Ile Val Leu Ser Ile Ala Ser Gly Leu Ala
            305                 310                 315 cat ttg cac ata gag ata ttt ggg acc caa ggg aaa cca gcc att gcc   1429
His Leu His Ile Glu Ile Phe Gly Thr Gln Gly Lys Pro Ala Ile Ala
        320                 325                 330 cat cga gat tta aag agc aaa aat att ctg gtt aag aag aat gga cag   1477
His Arg Asp Leu Lys Ser Lys Asn Ile Leu Val Lys Lys Asn Gly Gln
            335                 340                 345 tgt tgc ata gca gat ttg ggc ctg gca gtc atg cat tcc cag agc acc   1525
Cys Cys Ile Ala Asp Leu Gly Leu Ala Val Met His Ser Gln Ser Thr
350                 355                 360                 365 aat cag ctt gat gtg ggg aac aat ccc cgt gtg ggc acc aag cgc tac   1573
Asn Gln Leu Asp Val Gly Asn Asn Pro Arg Val Gly Thr Lys Arg Tyr
                370                 375                 380 atg gcc ccc gaa gtt cta gat gaa acc atc cag gtg gat tgt ttc gat   1621
Met Ala Pro Glu Val Leu Asp Glu Thr Ile Gln Val Asp Cys Phe Asp
            385                 390                 395 tct tat aaa agg gtc gat att tgg gcc ttt gga ctt gtt ttg tgg gaa   1669
Ser Tyr Lys Arg Val Asp Ile Trp Ala Phe Gly Leu Val Leu Trp Glu
        400                 405                 410 gtg gcc agg cgg atg gtg agc aat ggt ata gtg gag gat tac aag cca   1717
Val Ala Arg Arg Met Val Ser Asn Gly Ile Val Glu Asp Tyr Lys Pro
            415                 420                 425 ccg ttc tac gat gtg gtt ccc aat gac cca agt ttt gaa gat atg agg   1765
Pro Phe Tyr Asp Val Val Pro Asn Asp Pro Ser Phe Glu Asp Met Arg
430                 435                 440                 445 aag gta gtc tgt gtg gat caa caa agg cca aac ata ccc aac aga tgg   1813
Lys Val Val Cys Val Asp Gln Gln Arg Pro Asn Ile Pro Asn Arg Trp
                450                 455                 460 ttc tca gac ccg aca tta acc tct ctg gcc aag cta atg aaa gaa tgc   1861
Phe Ser Asp Pro Thr Leu Thr Ser Leu Ala Lys Leu Met Lys Glu Cys
            465                 470                 475 tgg tat caa aat cca tcc gca aga ctc aca gca ctg cgt atc aaa aag   1909
```

```
               Trp Tyr Gln Asn Pro Ser Ala Arg Leu Thr Ala Leu Arg Ile Lys Lys
                   480                 485                 490 act ttg acc aaa att gat aat tcc ctc gac aaa ttg aaa act gac tgt       1957
Thr Leu Thr Lys Ile Asp Asn Ser Leu Asp Lys Leu Lys Thr Asp Cys
    495                 500                 505 tga cattttcata gtgtcaagaa ggaagatttg acgttgttgt cattgtccag            2010
ctgggaccta atgctggcct gactggttgt cagaatggaa tccatctgtc tccctcccca     2070 aatgctgct ttgacaaggc agacgtcgta cccagccatg tgttggggag acatcaaaac      2130
caccctaacc tcgctcgatg actgtgaact gggcatttca cgaactgttc acactgcaga     2190
gactaatgtt ggacagacac tgttgcaaag gtagggactg gaggaacaca gagaaatcct    2250
aaaagagatc tgggcattaa gtcagtggct ttgcatagct ttcacaagtc tcctagacac    2310
tccccacggg aaactcaagg aggtggtgaa ttttaatca gcaatattgc ctgtgcttct     2370
cttctttatt gcactaggaa ttctttgcat tccttacttg cactgttact cttaatttta    2430
aagacccaac ttgccaaaat gttggctgcg tactccactg gtctgtcttt ggataatagg    2490
aattcaattt ggcaaaacaa atgtaatgt cagactttgc tgcattttac acatgtgctg     2550
atgtttacaa tgatgccgaa cattaggaat tgttttataca aactttgca aattatttat    2610 tacttgtgca cttagtagtt tttacaaaac tgctttgtgc atatgttaaa gcttattttt    2670
atgtggtctt atgattttat tacagaaatg ttttaacac tatactctaa aatggacatt     2730
ttcttttatt atcagttaaa atcacatttt aagtgcttca catttgtatg tgtgtagact    2790
gtaacttttt ttcagttcat atgcagaacg tatttagcca ttacccacgt gacaccaccg    2850
aatatattac tgatttagaa gcaaagattt cagtagaatt ttagtcctga acgctacggg    2910
gaaaatgcat tttcttcaga attatccatt acgtgcattt aaactctgcc agaaaaaaat    2970
aactattttg ttttaatcta cttttgtat ttagtagtta tttgtataaa ttaaataaac     3030
tgttttcaag tcaaaaaaaa aaaaaaaaaa aa                                   3062
```

<210> SEQ ID NO 10
<211> LENGTH: 509
<212> TYPE: PRT
<213> ORGANISM: Homo sapiens

<400> SEQUENCE: 10

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

```
Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
            165                 170                 175

Asp Ser Thr Leu Ala Asp Leu Leu Asp His Ser Cys Thr Ser Gly Ser
        180                 185                 190

Gly Ser Gly Leu Pro Phe Leu Val Gln Arg Thr Val Ala Arg Gln Ile
    195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 11
<211> LENGTH: 5263
<212> TYPE: DNA
<213> ORGANISM: Homo sapiens
<220> FEATURE:
<221> NAME/KEY: CDS
<222> LOCATION: (159)..(1700)
```

<400> SEQUENCE: 11

```
tgagcgtttt tttttttttt tttttttttt tttggtctgg gcttccgaat atgttttatg      60
acggttgatt ttacaccagg aggtttgtct ccgaggaaga cccagggaac tggatatcta     120
gcgagaactt cctccggatt ccccggcgcc tcgggaaa atg gga gct gct gca aag     176
                                          Met Gly Ala Ala Ala Lys
                                            1               5 ttg gcg ttt gcc gtc ttt ctt atc tcc tgt tct tca ggt gct ata ctt      224
Leu Ala Phe Ala Val Phe Leu Ile Ser Cys Ser Ser Gly Ala Ile Leu
         10                  15                  20 ggt aga tca gaa act cag gag tgt ctt ttc ttt aat gct aat tgg gaa      272
Gly Arg Ser Glu Thr Gln Glu Cys Leu Phe Phe Asn Ala Asn Trp Glu
     25                  30                  35 aaa gac aga acc aat caa act ggt gtt gaa ccg tgt tat ggt gac aaa      320
Lys Asp Arg Thr Asn Gln Thr Gly Val Glu Pro Cys Tyr Gly Asp Lys
 40                  45                  50 gat aaa cgg cgg cat tgt ttt gct acc tgg aag aat att tct ggt tcc      368
Asp Lys Arg Arg His Cys Phe Ala Thr Trp Lys Asn Ile Ser Gly Ser
 55                  60                  65                  70 att gaa ata gtg aaa caa ggt tgt tgg ctg gat gat atc aac tgc tat      416
Ile Glu Ile Val Lys Gln Gly Cys Trp Leu Asp Asp Ile Asn Cys Tyr
                 75                  80                  85 gac agg act gat tgt gta gaa aaa aaa gac agc cct gaa gta tat ttt      464
Asp Arg Thr Asp Cys Val Glu Lys Lys Asp Ser Pro Glu Val Tyr Phe
             90                  95                 100 tgt tgc tgt gag ggc aat atg tgt aat gaa aag ttt tct tat ttt ccg      512
Cys Cys Cys Glu Gly Asn Met Cys Asn Glu Lys Phe Ser Tyr Phe Pro
         105                 110                 115 gag atg gaa gtc aca cag ccc act tca aat cca gtt aca cct aag cca      560
Glu Met Glu Val Thr Gln Pro Thr Ser Asn Pro Val Thr Pro Lys Pro
 120                 125                 130 ccc tat tac aac atc ctg ctc tat tcc ttg gtg cca ctt atg tta att      608
Pro Tyr Tyr Asn Ile Leu Leu Tyr Ser Leu Val Pro Leu Met Leu Ile
135                 140                 145                 150 gcg ggg att gtc att tgt gca ttt tgg gtg tac agg cat cac aag atg      656
Ala Gly Ile Val Ile Cys Ala Phe Trp Val Tyr Arg His His Lys Met
                 155                 160                 165 gcc tac cct cct gta ctt gtt cca act caa gac cca gga cca ccc cca      704
Ala Tyr Pro Pro Val Leu Val Pro Thr Gln Asp Pro Gly Pro Pro Pro
             170                 175                 180 cct tct cca tta cta ggt ttg aaa cca ctg cag tta tta gaa gtg aaa      752
Pro Ser Pro Leu Leu Gly Leu Lys Pro Leu Gln Leu Leu Glu Val Lys
         185                 190                 195 gca agg gga aga ttt ggt tgt gtc tgg aaa gcc cag ttg ctt aac gaa      800
Ala Arg Gly Arg Phe Gly Cys Val Trp Lys Ala Gln Leu Leu Asn Glu
 200                 205                 210 tat gtg gct gtc aaa ata ttt cca ata cag gac aaa cag tca tgg caa      848
Tyr Val Ala Val Lys Ile Phe Pro Ile Gln Asp Lys Gln Ser Trp Gln
215                 220                 225                 230 aat gaa tac gaa gtc tac agt ttg cct gga atg aag cat gag aac ata      896
Asn Glu Tyr Glu Val Tyr Ser Leu Pro Gly Met Lys His Glu Asn Ile
                 235                 240                 245 tta cag ttc att ggt gca gaa aaa cga ggc acc agt gtt gat gtg gat      944
Leu Gln Phe Ile Gly Ala Glu Lys Arg Gly Thr Ser Val Asp Val Asp
             250                 255                 260 ctt tgg ctg atc aca gca ttt cat gaa aag ggt tca cta tca gac ttt      992
Leu Trp Leu Ile Thr Ala Phe His Glu Lys Gly Ser Leu Ser Asp Phe
         265                 270                 275 ctt aag gct aat gtg gtc tct tgg aat gaa ctg tgt cat att gca gaa     1040
Leu Lys Ala Asn Val Val Ser Trp Asn Glu Leu Cys His Ile Ala Glu
```

```
Leu Lys Ala Asn Val Val Ser Trp Asn Glu Leu Cys His Ile Ala Glu
    280                 285                 290 acc atg gct aga gga ttg gca tat tta cat gag gat ata cct ggc cta     1088
Thr Met Ala Arg Gly Leu Ala Tyr Leu His Glu Asp Ile Pro Gly Leu
295                 300                 305                 310 aaa gat ggc cac aaa cct gcc ata tct cac agg gac atc aaa agt aaa     1136
Lys Asp Gly His Lys Pro Ala Ile Ser His Arg Asp Ile Lys Ser Lys
                315                 320                 325 aat gtg ctg ttg aaa aac aac ctg aca gct tgc att gct gac ttt ggg     1184
Asn Val Leu Leu Lys Asn Asn Leu Thr Ala Cys Ile Ala Asp Phe Gly
            330                 335                 340 ttg gcc tta aaa ttt gag gct ggc aag tct gca ggc gat acc cat gga     1232
Leu Ala Leu Lys Phe Glu Ala Gly Lys Ser Ala Gly Asp Thr His Gly
        345                 350                 355 cag gtt ggt acc cgg agg tac atg gct cca gag gta tta gag ggt gct     1280
Gln Val Gly Thr Arg Arg Tyr Met Ala Pro Glu Val Leu Glu Gly Ala
    360                 365                 370 ata aac ttc caa agg gat gca ttt ttg agg ata gat atg tat gcc atg     1328
Ile Asn Phe Gln Arg Asp Ala Phe Leu Arg Ile Asp Met Tyr Ala Met
375                 380                 385                 390 gga tta gtc cta tgg gaa ctg gct tct cgc tgt act gct gca gat gga     1376
Gly Leu Val Leu Trp Glu Leu Ala Ser Arg Cys Thr Ala Ala Asp Gly
                395                 400                 405 cct gta gat gaa tac atg ttg cca ttt gag gag gaa att ggc cag cat     1424
Pro Val Asp Glu Tyr Met Leu Pro Phe Glu Glu Glu Ile Gly Gln His
            410                 415                 420 cca tct ctt gaa gac atg cag gaa gtt gtt gtg cat aaa aaa aag agg     1472
Pro Ser Leu Glu Asp Met Gln Glu Val Val Val His Lys Lys Lys Arg
        425                 430                 435 cct gtt tta aga gat tat tgg cag aaa cat gct gga atg gca atg ctc     1520
Pro Val Leu Arg Asp Tyr Trp Gln Lys His Ala Gly Met Ala Met Leu
    440                 445                 450 tgt gaa acc att gaa gaa tgt tgg gat cac gac gca gaa gcc agg tta     1568
Cys Glu Thr Ile Glu Glu Cys Trp Asp His Asp Ala Glu Ala Arg Leu
455                 460                 465                 470 tca gct gga tgt gta ggt gaa aga att acc cag atg cag aga cta aca     1616
Ser Ala Gly Cys Val Gly Glu Arg Ile Thr Gln Met Gln Arg Leu Thr
                475                 480                 485 aat att att acc aca gag gac att gta aca gtg gtc aca atg gtg aca     1664
Asn Ile Ile Thr Thr Glu Asp Ile Val Thr Val Val Thr Met Val Thr
            490                 495                 500 aat gtt gac ttt cct ccc aaa gaa tct agt cta tga tggttgcgcc         1710
Asn Val Asp Phe Pro Pro Lys Glu Ser Ser Leu
        505                 510 atctgtgcac actaagaaat gggactctga actggagctg ctaagctaaa gaaactgctt   1770
acagtttatt ttctgtgtaa aatgagtagg atgtctcttg gaaatgttaa gaagaagac    1830 cctttgttga aaatgttgc tctgggagac ttactgcatt gccgacagca cagatgtgaa    1890
ggacatgaga ctaagagaaa ccttgcaaac tctataaaga aacttttgaa aaagtgtaca   1950
tgaagaatgt agccctctcc aaatcaagga tcttttggac ctggctaatg gagtgtttga   2010
aaactgacat cagattcctt aatgtctgtc agaagacact aattccttaa atgaactact   2070
gctatttttt ttaaatcaaa aacttttcat ttcagatttt aaaaagggta acttgttttt   2130
attgcatttg ctgttgtttc tataaatgac tattgtaatg ccaatatgac acagcttgtg   2190
aatgtttagt gtgctgctgt tctgtgtaca taaagtcatc aaagtggggt acagtaaaga   2250
ggcttccaag cattactttta acctccctca acaaggtata cctcagttcc acggttgcta   2310
```

```
aattataaaa ttgaaaacac taacaaaatt tgaataataa atcgatccat gttttgtaac    2370
aaattcactg tgttatttaa ggaaaaaaag gtaagctatg cttagtgcca acaataagtg    2430
gccattcgta aagcagtgtt ttagcatttc ttgtgctggc ttgtaatgta gggaaaaaaa    2490
gtgctgtttt ttgaaaagat ggtgtcattt ccccttctt cccatgtttt aaagccccat     2550
cttatatcca gttcccaaaa tttgcatact tacctaagta ttttttttag gtgtgctgtg    2610
tttggggaat atttgaaaat ttaaagcatg atttaaaatt tttaaagtg agctgtgaca     2670 ctggaaagct cttcatttta tcttttaaaa tagagttttt tctatttata tatgtaaaat    2730
tgtagtgtat ttcttttcac caaacagtgt gtgggacatt ctttatcact gttttaggat    2790
cacctcagga agtgtcgtta cccagaattc cccactgtct gctatgagac ttgtaacttt    2850
atcactatac ttctgcttgg tgccatcttg tcagagtaat atttgatgtc tgtgatatgt    2910
aaagaattat cctaggataa agatattaaa ctttaagcag atttcagatg ttactgcttt    2970
aaaacaaatc agggataaca aattaaacgt ataacttaaa atatgcaatg acatttagag    3030
gtaaccaatg ttgatatagg tagcatagcc tagcctcctc cccaaaattg cttttacaac    3090
taacactgat actaatttag gatagttcat gccttatcct tgctaagaaa atggaattga    3150
tggtaggcag gtgctaaagt gcttttcaaa acaatattac gttagaatac aattggattc    3210
ttcctcaaat ttatacaggc caaaaagtaa aacattaatt ttctgaattt ccagattacc    3270
aatcaattaa tcaacaaata gccagtatta tgctgtgtat ttctgtcagg tcattttaaa    3330
atccatgtta attttataaa agaattttt acatgtcact gtcaggagct cactgtgaat     3390
gtgttgtctt caaatggtta tttaaccaca cagtacacta cattttacat atatgtacgt    3450
aatctctggg aatagtaaat taattatgtt atttataaac aatacatagg tcaacagact    3510
ttaagcaggg aggaaaagaa gagtaatagc gtctgtgtgc tgcagaccat tcagaactgt    3570
cacgtgtgtc cccatggtct cattcattgt attcctagca attccttttt caatgttgag    3630
ttcacctctt tatttcacaa agtacttggt ctctcaattt cttgatctgg ttttgcttcc    3690
atttaaaaac taatcaagaa gggaaaatat tgagaatgtg catacaagaa aatcattaat    3750
ttcctgaaga tgaatttcta cctgttgtga acatttaact ttcttttttaa aagttaaaca    3810 aaaataaaca agggatatta tgatgaatgt ttggcttatg tgagtactag agataaaatt    3870
tttaaaccca gttattcaca atataaaatg ttttcaagtt agaaaaaatt tttagaaatc    3930
ctgggtattg tatttaactg tagctaacca attttaaaac ttgtattctt ttgagaacta    3990
ttattaatag aaaaactttt tataagcagt aaaataagaa tgttccagtg actacctgtc    4050
cttataccta gtcttgttaa aactttcttt tgcagggtat ttagtgtttg gtttacagtc    4110
agtgcagagt gggcaagtta acagaaagtt tgagctagag atactggaaa aaaaaagat     4170 caaagaatga gaaaaatggt gatccatttt ggggcaaact gagacccccc aaataactct    4230
ttcctcatgt gtatggtgct cctcatgact cgtcttgtat tttgcctttc tgatacccat    4290
cagaactgct gctgctctaa cttatactct ttaccttgcc cagatctccg cgtaaggaat    4350
gctttatgat caacttgcca taggactgat ggattaacca gtgttcggct ttatttgaag    4410
tctatgccct gcacagctct tgtatgtatt ttagatgcta gaagtttttt tagcatgtga    4470
tgtgtgattc ttgtttgaat tctaggtacc ttgtgaattc cagaaaaaga gactgtgctt    4530
cacgattgtt agtcccatga acttgcacta tctatctttc atggtgatgt tttgaaaata    4590
caatcaggaa aaaacccaac accctttggaa tttaaaatag aatcatatca tgaaatttaa    4650
aaagaatctc ttctgttgca tttcctcacc cctaagtaac agctacattt aagtaaaatg    4710
```

```
caggtggtag gggaaaaaaa accatggcga gatggtggtt tagtggaata aactgattac    4770
tggttttttt gtttttttt tttttttaa agaaagaagc ttcatcacag atactttcca    4830
gtttctcttt tatactttt tgaaagatta cttttagga acatttggta tgatatgcat    4890
aaaattattt atccatttat gggcaaaatg atacaagtag catcttgatt gaacatcatt    4950
tacctcagat attcaaccag cagtacgttt tttatgcagt ctcaacccat atcccatttg    5010
ttacctctca gaatattggt aagcagttat tttcgcttta ctctgtattt cttgtgtttt    5070
gggcacaggt tattgtacta ctgtcaaatc gtacttgcta ttttttctgc aagtatttaa    5130
cagaaagctt aaaatcccca taaaacccca ccttggataa gtgattgtta aatattgtac    5190
aaataaaatg tatgctatcc ccattccatc cccaagttaa ataaaaaaat gaatacggta    5250
tgaaaaaaaa aaa    5263
```

<210> SEQ ID NO 12
<211> LENGTH: 513
<212> TYPE: PRT
<213> ORGANISM: Homo sapiens

<400> SEQUENCE: 12

```
Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270
```

```
Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
                355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
    435                 440                 445

Ala Gly Met Ala Met Leu Cys Glu Thr Ile Glu Glu Cys Trp Asp His
    450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 13
<211> LENGTH: 11373
<212> TYPE: DNA
<213> ORGANISM: Homo sapiens
<220> FEATURE:
<221> NAME/KEY: CDS
<222> LOCATION: (25)..(1563)

<400> SEQUENCE: 13
gtgcgcgggg cggcgccgcg gaac atg acg gcg ccc tgg gtg gcc ctc gcc        51
                         Met Thr Ala Pro Trp Val Ala Leu Ala
                           1               5 ctc ctc tgg gga tcg ctg tgc gcc ggc tct ggg cgt ggg gag gct gag        99
Leu Leu Trp Gly Ser Leu Cys Ala Gly Ser Gly Arg Gly Glu Ala Glu
 10              15                  20                  25 aca cgg gag tgc atc tac tac aac gcc aac tgg gag ctg gag cgc acc       147
Thr Arg Glu Cys Ile Tyr Tyr Asn Ala Asn Trp Glu Leu Glu Arg Thr
             30                  35                  40 aac cag agc ggc ctg gag cgc tgc gaa ggc gag cag gac aag cgg ctg       195
Asn Gln Ser Gly Leu Glu Arg Cys Glu Gly Glu Gln Asp Lys Arg Leu
         45                  50                  55 cac tgc tac gcc tcc tgg cgc aac agc tct ggc acc atc gag ctc gtg       243
His Cys Tyr Ala Ser Trp Arg Asn Ser Ser Gly Thr Ile Glu Leu Val
     60                  65                  70
```

-continued

| | | |
|---|---|---|
| aag aag ggc tgc tgg cta gat gac ttc aac tgc tac gat agg cag gag<br>Lys Lys Gly Cys Trp Leu Asp Asp Phe Asn Cys Tyr Asp Arg Gln Glu<br>75              80              85 | 291 |
| tgt gtg gcc act gag gag aac ccc cag gtg tac ttc tgc tgc tgt gaa<br>Cys Val Ala Thr Glu Glu Asn Pro Gln Val Tyr Phe Cys Cys Cys Glu<br>90              95              100             105 | 339 |
| ggc aac ttc tgc aac gaa cgc ttc act cat ttg cca gag gct ggg ggc<br>Gly Asn Phe Cys Asn Glu Arg Phe Thr His Leu Pro Glu Ala Gly Gly<br>110             115             120 | 387 |
| ccg gaa gtc acg tac gag cca ccc ccg aca gcc ccc acc ctg ctc acg<br>Pro Glu Val Thr Tyr Glu Pro Pro Pro Thr Ala Pro Thr Leu Leu Thr<br>125             130             135 | 435 |
| gtg ctg gcc tac tca ctg ctg ccc atc ggg ggc ctt tcc ctc atc gtc<br>Val Leu Ala Tyr Ser Leu Leu Pro Ile Gly Gly Leu Ser Leu Ile Val<br>140             145             150 | 483 |
| ctg ctg gcc ttt tgg atg tac cgg cat cgc aag ccc ccc tac ggt cat<br>Leu Leu Ala Phe Trp Met Tyr Arg His Arg Lys Pro Pro Tyr Gly His<br>155             160             165 | 531 |
| gtg gac atc cat gag gac cct ggg cct cca cca cca tcc cct ctg gtg<br>Val Asp Ile His Glu Asp Pro Gly Pro Pro Pro Pro Ser Pro Leu Val<br>170             175             180             185 | 579 |
| ggc ctg aag cca ctg cag ctg ctg gag atc aag gct cgg ggg cgc ttt<br>Gly Leu Lys Pro Leu Gln Leu Leu Glu Ile Lys Ala Arg Gly Arg Phe<br>190             195             200 | 627 |
| ggc tgt gtc tgg aag gcc cag ctc atg aat gac ttt gta gct gtc aag<br>Gly Cys Val Trp Lys Ala Gln Leu Met Asn Asp Phe Val Ala Val Lys<br>205             210             215 | 675 |
| atc ttc cca ctc cag gac aag cag tcg tgg cag agt gaa cgg gag atc<br>Ile Phe Pro Leu Gln Asp Lys Gln Ser Trp Gln Ser Glu Arg Glu Ile<br>220             225             230 | 723 |
| ttc agc aca cct ggc atg aag cac gag aac ctg cta cag ttc att gct<br>Phe Ser Thr Pro Gly Met Lys His Glu Asn Leu Leu Gln Phe Ile Ala<br>235             240             245 | 771 |
| gcc gag aag cga ggc tcc aac ctc gaa gta gag ctg tgg ctc atc acg<br>Ala Glu Lys Arg Gly Ser Asn Leu Glu Val Glu Leu Trp Leu Ile Thr<br>250             255             260             265 | 819 |
| gcc ttc cat gac aag ggc tcc ctc acg gat tac ctc aag ggg aac atc<br>Ala Phe His Asp Lys Gly Ser Leu Thr Asp Tyr Leu Lys Gly Asn Ile<br>270             275             280 | 867 |
| atc aca tgg aac gaa ctg tgt cat gta gca gag acg atg tca cga ggc<br>Ile Thr Trp Asn Glu Leu Cys His Val Ala Glu Thr Met Ser Arg Gly<br>285             290             295 | 915 |
| ctc tca tac ctg cat gag gat gtg ccc tgg tgc cgt ggc gag ggc cac<br>Leu Ser Tyr Leu His Glu Asp Val Pro Trp Cys Arg Gly Glu Gly His<br>300             305             310 | 963 |
| aag ccg tct att gcc cac agg gac ttt aaa agt aag aat gta ttg ctg<br>Lys Pro Ser Ile Ala His Arg Asp Phe Lys Ser Lys Asn Val Leu Leu<br>315             320             325 | 1011 |
| aag agc gac ctc aca gcc gtg ctg gct gac ttt ggc ttg gct gtt cga<br>Lys Ser Asp Leu Thr Ala Val Leu Ala Asp Phe Gly Leu Ala Val Arg<br>330             335             340             345 | 1059 |
| ttt gag cca ggg aaa cct cca ggg gac acc cac gga cag gta ggc acg<br>Phe Glu Pro Gly Lys Pro Pro Gly Asp Thr His Gly Gln Val Gly Thr<br>350             355             360 | 1107 |
| aga cgg tac atg gct cct gag gtg ctc gag gga gcc atc aac ttc cag<br>Arg Arg Tyr Met Ala Pro Glu Val Leu Glu Gly Ala Ile Asn Phe Gln<br>365             370             375 | 1155 |
| aga gat gcc ttc ctg cgc att gac atg tat gcc atg ggg ttg gtg ctg<br>Arg Asp Ala Phe Leu Arg Ile Asp Met Tyr Ala Met Gly Leu Val Leu<br>380             385             390 | 1203 |

```
tgg gag ctt gtg tct cgc tgc aag gct gca gac gga ccc gtg gat gag    1251
Trp Glu Leu Val Ser Arg Cys Lys Ala Ala Asp Gly Pro Val Asp Glu
    395                 400                 405 tac atg ctg ccc ttt gag gaa gag att ggc cag cac cct tcg ttg gag    1299
Tyr Met Leu Pro Phe Glu Glu Glu Ile Gly Gln His Pro Ser Leu Glu
410                 415                 420                 425 gag ctg cag gag gtg gtg gtg cac aag aag atg agg ccc acc att aaa    1347
Glu Leu Gln Glu Val Val Val His Lys Lys Met Arg Pro Thr Ile Lys
                430                 435                 440 gat cac tgg ttg aaa cac ccg ggc ctg gcc cag ctt tgt gtg acc atc    1395
Asp His Trp Leu Lys His Pro Gly Leu Ala Gln Leu Cys Val Thr Ile
            445                 450                 455 gag gag tgc tgg gac cat gat gca gag gct cgc ttg tcc gcg ggc tgt    1443
Glu Glu Cys Trp Asp His Asp Ala Glu Ala Arg Leu Ser Ala Gly Cys
        460                 465                 470 gtg gag gag cgg gtg tcc ctg att cgg agg tcg gtc aac ggc act acc    1491
Val Glu Glu Arg Val Ser Leu Ile Arg Arg Ser Val Asn Gly Thr Thr
    475                 480                 485 tcg gac tgt ctc gtt tcc ctg gtg acc tct gtc acc aat gtg gac ctg    1539
Ser Asp Cys Leu Val Ser Leu Val Thr Ser Val Thr Asn Val Asp Leu
490                 495                 500                 505 ccc cct aaa gag tca agc atc taa gcccaggaca tgagtgtctg tccagactca   1593
Pro Pro Lys Glu Ser Ser Ile
                510 gtggatctga agaaaaaagg aaaaaaagtt gtgttttgtt ttggaaatcc cataaaacca   1653 acaaacacat aaaatgcagc tgctatttta ccttgacttt ttattattat tattataatt   1713 attataatta ttattattaa tattattttt tggattggat cagttttttac cagcatattg   1773 ctctactgta tcacaaacag cggacacgtc agcaggcgtt gaggtgctga gctgtggatg   1833 cagaaccagc gccatgctga agagcctcag ccacctcctg tcctttggga ttcgttttc    1893 ccgctttctc tttgtttgtc gtctcagaat ctgtgacaca agaaaccca tctcctgtct    1953 taggaaacct aatgctgcaa actctaccta gaggaacctt tgaagactgt tacataagaa   2013 catccttcc tcagaagagg agtttcctct gccctctgcc cttctccct gcctccctcc     2073 ctcccctcct tttattttgt tttagtgagc ttaagaaaca gcagatgtgt ctttcacgga   2133 tctaacgggt gttgtcctga tcgagaaaaa aactgggatg agaatggttt ggactggagt   2193 tggaagggga ggacggtact gggggtaggg tttgaacag agctacactg gactcgggca    2253 cattcggagc agcatccttt agtatggagg ctacttctca ggtaaccagg aattgagggg   2313 aaggaccttg tggaggccga gcattaacag caagagcggg gtttggagaa agtctgagat   2373 tgggtgcagc cctgacttac ctgctggccc tgaccagttt cttttcacta acttggcctt   2433 gggcatagga tgaaacattt ttctgccct aattttaaaa ctaggtgagg gtagaatcat    2493 cacaggttag aatacattc ttcataagac acgatgctgt aaatacccttt aatggacgaa   2553 aagttgaaat acttttgttt cctcttggag cagttcaggg aaatgcccac aggggattgt   2613 cctgcacaga tagggcaaga ggatttcctg ggtggagtct gccaaggcct gcctcgctgg   2673 ggaccccaga gtcctgcacc tctggttccg ccccaggtgg tgacattact gtccccgttc   2733 tgtggctcgt ggacaagact ttctccagac cccttaaagt ggtacatatt ctaaaaaact   2793 gttttttctat tatgccataa ccttgctcta gtcagtgaat gttcctaatg ctgctgtttc   2853 aacatttgaa ttcttttttaa tttatgaaac atgctaaatt ttttttttca acaaaaacac   2913 acacatccac atatacacat gcttcgctat gtggcttcca aggtttaaat tttgaaaagt   2973
```

```
aaaagaatta aaacttcacg accacagatc acctcaaacc agaaatacct cagaattttc    3033
tacttatgta aggtttatta tatattttgt tagttgtgtt gtcttgtagt aagtatattt    3093
taatgtaagt tggcttttgt gacaaggaag tttaaaagaa atagagaaaa agaaaaaagt    3153
ttgcatcttc tagggagtgc taccattttt gtttgataac gcccccttgt aaataattgt    3213
catcaactgt aggttggctg tctgggccaa gtctgggcat ttatcagtct tgtttgtgaa    3273
ggcttttcct tctggtttct ttagatcatt ttatttaaaa acagtgcatc tcttcatcgt    3333
gagggtaggc aaggcggggg ccgtggggag aggttgacct gggtgagaac tgaagaggcc    3393
gcctcctctt gggttgtttg gagcttcaca tgtaattcac atgtaacatg taacttgatc    3453
ggtcagtgtt cagaatgaca agtaaccccg cttaaacttg gtagaaggat ggcccttaga    3513
cctgaatggg gtgattttac ttgggattta acttcttcag caaattaaca gcaacgttgg    3573
aagagatctg tggcgcctct gtgaagcaca ccgtgactca ggccagtctt ttagtgcagc    3633
gtgtctggga gtgaagggtt ttgcccttgc tggtcttgga gtccacagtg tgagggcac     3693 tgcacatgcc tgggcatcta cctagtgtgc tatgttcagt gtctgggct tactgccccg     3753 gggtcctttc ctctgggtgt tggggcacag ggtgctatgg gaggcccatt tgcttccctc    3813
tcggagctca gtttttgctt catgggtcaa aatgtgggct ggccaagtgg ttacaggaac    3873
agggtttcgg taagctatgt tgtctttttt tttttttttt tttttttttt taatggtttg    3933
attttgtgct gtggtatttt ttttcccttla gaataatttt taatggcaaa acaggcctta    3993
cagcagttgc ttttctttac catttatttc tttaagaagc tttaaaatat ttattgaaaa    4053
gtgccatatc taatttcttt agctttcgcc tcaggcagtg caggcatctt tacttttcat    4113
cctcagaaga aacaaacgac taacaaatgt agcaaattta ctgcaggaat agttaggtca    4173
tgatactacc tgaacactaa accccagcct cttttgtttgg ttttagttcc tctgggtggt    4233 ttttctttttg tgtgctggct tgattcttgt gagaagtttt gacctggcca agggagggtt    4293
gagccatggt tctggtgtgg gactttgcgg tcaagacaca gtacagacag gtcaggcctg    4353
cgtgcctttt ctctgggtgg cctccccgtt aggcccaccg tacgctcagc cactatagtg    4413
tccctgtggg gccttgccat cagattgtgt gtcaggagat ggtaccttt tggtgtggct     4473 ggggaggagt gtggtccatg ccagttcttt gggcttcagg ccactcttcc cctcatgctg    4533
tggtgtaaag tgcacccatc aggtggtata tctggttctg atggcaagaa gaaggtgggg    4593
gatctcctta tagggcatgg gtctaggagc acagatgggc cttttgcccc gggtaaatgc    4653
ttgtctgttt gctgtcatgt gttctttgag gagtgagcca tctcgagccc tgctttgaat    4713
ttactgggtc atagagcctc tgcctgtgct cttttccata atgacttcat gtgacatgca    4773
cttttggtgg gctcagataa ttggtttctt tttgttttttg acctcaggct ctgtggcaga    4833
ctggggaaaa tggggcctgg catcattttc cctgtcaatg ggaggggctg ttccatgcag    4893
ggtgggaggg gaccaagtta gcagagagta gccaaggatc cttgcttctt cctttctagt    4953
gtgctgtcat ccaagcaggc tcctggctgt agggatgggc cttggggaag aatcttcttt    5013
gaaagcatct atgataactg agaagtcatc cctagttgga gaaatccagt aatgagcaga    5073
aggaggaagc aagtgaggac agaggccatt gtattacagt gtcacgcaga gggccctcaa    5133
tgatggggca ttggggaagg ctgtagacat agtcatcaga acatcctggc ctggcataag    5193
ctgggttttc tcctgggacc attggtcctc agcaggagtt ctttgcatga gttgctcagg    5253
ggcaagggct gcaagtgggc tgtgcttagg agaaagtgac acctggcagt gagggaagat    5313
ggtgagcatt attagccttt gttgtccagc atggccttct tgtcctgtct gctctggaga    5373
```

```
ggagcctgtg ggaccagtcc tgcctgggga gggcataccc acacgtgcca gctgattctg    5433
actctgaata catcatgtcc ggacttgggg gtgtttctgc agaaaaagga ggttgttttt    5493
cagccttgaa catcttcagg aggatagaga ctcttgctca catattctta gcaaagggaa    5553
gggtctctca tctccaggcc acagagatag ttcttccatt gccctaagag ctaggctaa    5613 ccctcttgac ataacttaga cagcaaagca cttcatcctg tagttgggct ctgtcacctt    5673
tctcttcagt tggccacatt ctcgtttcct ccatcctgct atgctttgtg tgctcgggct    5733
gtgtgtgggg tttttccctg gtggaaggaa gcccagctgt gtattgaatg tccttcatgt    5793
gttgtgtgtg gctcagaaag cctgtcactt ggccctgtg ctctgagccg tgagggtggg    5853
gaggtggctg ttccattaaa gtgggagtat tggatggccc tcttgaaact agaattttgc    5913 ctttttagt atgcagtata aagtttccag catctattgg taacacaaag atttgctggt    5973
ttttaaaata atacagtaag cataagtatg taagttttta gaattggtac tagaagttgg    6033
acagctagtt attctcgaga actttatttc actagaaaaa tatactaatt ggaaagcagt    6093
ttccaggagt taactcagtt taattttcag tctcagttat tttagcctgt tgagttttg    6153 atggcacacc tttggagaga tggccacgcc tgattcccat ttcaggggca tcagaccata    6213
cctttttaag aagctccgtg aatctagtca tctacccttc atcctgggcg aacagccaaa    6273
aagagaaggg gacaaggtgt cttttttctcc ttctcactgg ggtgacatga attcttttag    6333
ttaatggctg tttgcaaatt ctaaactaat gaaatactta gcagctaaca tgttcaatct    6393
agtaatgatg agtttaaatc tcaattgaca gtaatgtttt agataaacag gcccagtaat    6453
tcagttgatg aactgtatat cttctcagtc tagatttgta aatgtttaat gaattcaggg    6513
ttataagcat agttctttaa gtaagattcc agatagttga tttgcaacca gcagtctacc    6573
tatgaatgta tcccaaacct ttagaagatt ggaaaagatt tttgaaataa tgatttagtt    6633
ttgtaggaaa acaccccct tgaaaattaa ttcggttgac ccagtaacat tttttaaaac    6693
aattggtggc tccaaaaggc ctgccaacaa agaaaagtcc aaattatcta gtgggacatt    6753
ttgaatgttt tatgtttatt ttgggtccac tgtaaacttt ggttcaaaaa agaatttgaa    6813
tttaaagaat ttaccattat ttaaattatt accaagtttt tacattttca tgatggtatt    6873
ttccaggtat gaatgaaaca tgactttttg attgtggtac ttcctgtatc ccctgtagtg    6933
ccaaaaccag tgatacttta tttgctccta tggcagctca tagaggtaac cgaagtgatt    6993
tttcctcagt aattgaaaca catattctct aaatgccaat gtgtggtgat gggccctgca    7053
ctgccttcat ttctctaggg cagtgtcttt ggattgtcta gggcctaggt aattctgaga    7113
actactgtaa accaaccaca gggcactaaa gcaatgtaca caccactctt tgtgtgtatg    7173
gaaggggtta tataaacctg gctatgctg acatctaca aagagtatt acattcactt    7233 gcaaagttta cattttgag ctcacagtta tgaaaaatat gacccacaag ttttcaggc    7293 aggtgaggat gggtcttctt gcaaatgcat gagttctgtc ttgagtcctg gaacttctc    7353 tgttggttga gtgtgggctc attccctgac tctcctaatc atgtttgcgt cagaatgtta    7413
gcattgtaaa taaagaata ggttgtaaa tagatacaca acacttgaaa ctttacttta    7473
aaaaaatcga tagttctaca tatatattta gttatatcac ttgacagatt tcttctacac    7533
agtgtggaga ttgttttata ccacagatta ttttttataaa gttagtgaat ttgaatgatt    7593
ttgtaatcag agctaatgag ctttacctttt caagagaaac gtacactgga gcatgagtgg    7653
tgtggaactt ttacttagtg tttatatgga ttcttgtgat acactggcag actggagtca    7713
```

-continued

```
atttgcgggt cttttttggc caaaactcca cttgtggttg tgtaggacag tgatattcag    7773
ctcagcttct tgtggattgg gaggagagag ggcctgcaat gtgttttaca ttggtgcttc    7833
ctcctgagat ttctgttgaa caaagggttc tgaggtcaaa aattagtttg taagcctttg    7893
ccataggaca tagtcatgtg agagtgtttg ggggaacaga aattgtatag gggtgcctat    7953
tggggtggga tgggactcga ataagattca ggtacaaaaa ctttgaaatg agaatctggt    8013
ggtttgagta atccaccaga ctgaattatc taagatcaca ttatccaggt tgggggggcag   8073
aattacccag ttaagtaatt gttcagaaaa gtggggaggg tggcatgtgg atgcagtgat   8133
ccaattaaat ggagagctgc caggcacatt ttgtcctctc tggtcagtga aatggttgg    8193
gttggctcgc tgcttcaatc tgtggaatca gccaggagcc cagtgaggaa gctcagaacc    8253
ccagtaacag cagagcatct ttcagatagc tccagagttt tcctgctttt ctgaggaagc    8313
tcagcatcac tgccacaata cggaaagtgg tcttcatttt agcctattta tttttaggca   8373
gagagtggat ggttatttgt gtgggacttt tggtggcgat atataatgaa taattaagtt   8433
aatttctggt atgcataatg ccagtcctg aggcccagct gaagacctgt cccccagacc    8493
ctgcccgctg gcttcaggct gctgcttcta gacagaggtg cactggacgg atagttttta  8553
tcaagagaat ccctaatgtg tcattttaaa ccagctgtgc ttttattca ttctggttga   8613
gcgtataggt ttacacttta cccttttat acttggaata aatttagttc cagcagatct   8673
agtagcactc cagaaaccaa ccccatctgt tccccataaa aagaacattt tctctgctct   8733
ccagccacgt gtcttggaat gtaattctgt tgtgcctttg tttttatcac tctcttcgcc   8793
ccaaaagcaa ctgctgtaag cttttttcta cttgtctttt ctagtcccca acctctacct   8853
ttttcctttt tcccagccct aatttctgga tgcacttctg tgatccaggt atttaagaa   8913
ccagttacct cagacctcat gttgaacagt gtcgccatct gggtcctctt gatactgcag    8973
acttttaacg tacacatgca ggaaccctgc tgagcgtggg cacttgtttt aaagcaaaac   9033
tcttcccaag gactgaagaa agggcttctg gcaagctcgt catggcattg tggtgggatg   9093
ggtctagagt gtcatctgaa tggtgcttcc tgtgttcctc tttgaattct gccattttca   9153
gtattcttgt gtgtctgaat aggcaaagcg atttaattgg ctggtcttgc acgcaaatta   9213
gttccaaaga taagctcttt gtaacacatt tccagtcgct aatgctcaaa tgtagaacat   9273
tcctttaaat ggcaggataa aaacccact atccaccata gtgcattttg ggaagatgtc    9333
tgtagcatat gttgctgtga aattaggcct tgtgggatat ggctgtttgt cattttgatg   9393
tattttaaat aaatatatat atttttaaa gagccttttt taccagttca aaaagtttaa    9453
ttaaccagca gtcaccgcat ctgaattttt gtctctgggg catagatggc agaccaagat    9513
taaaagtggt aactcagcta tacgagcatg ggctaccttc ctgggctctc ctgcagtcct   9573
gtagacctgc tgttccgcag accatgggac acaaggtcag tgtgttccca gtgagggtcc   9633
caagtcagtc atcttaagtg tttgttctct gccccattca gtggactgtt gacttcagtc    9693
cctgcaagtg ctttagcccg agtgggggttt tctcagagca ctgccacgag ttaagtgtgt   9753
gtttagccaa ataatttctc cgtaagggaa aaatgcagtc acccaaattt taccaacaat    9813
gacagagatg agagtagaaa agattaggca acatctgagt tttaacttga aaagtgtcca   9873
agtcatcatg aaaggccgac tgggagcaag tgattattag agattcttca ggagacctca   9933
tctgaaaatg ttaagactgc cagtgaggga aggaattgtt aaaatgccag cggctttttt    9993
ttcctctttt tttctgtaat tctgtaaaaa tgcagagaaa gttgagtggt acttcagaat   10053
tgagggagag ggttaccgca gagtagaaat atatttctag atttcagttc cacaccacaa   10113
```

```
atccacaaca atgccatttt tcaactgtac aaaaatctgc ttatgaactg gacatgatct   10173
taatggtagt gtcaaaggcc aagttttttca cctgttaata ttttttccaca tttgtccttg   10233 aatctgaata actttataca gtactgtaaa tttaacttac atcgagtttg ttgtcaattc   10293
ttatgaaaag agctttctgc atgtaacaca tacggttaaa gaacacagca aaggacaaaa   10353
tttgcaggaa cagttttgga accaacagaa aatgtcacct tttatttgcc atcttatata   10413
tatctatcag ttttaccagc tacttctaaa tttgtacatt atttgtaagg gaaagaagga   10473
aaaccctaag acttgtctaa cttagtggag aatgtgtgtg ttgggcttag gatggatagc   10533
taagtcttat tgagctgtgt tacctaactt gtatataaaa attgtaatta aaagtttggg   10593
ttcacctgtt tctcacagtt taaaatgatg agtaattgca aactctggaa atgtgactag   10653
tatatgattt aaggctgtag aagcaaggaa gctctttcaa gtgctaaaac taaagacttc   10713 tagttttttgg ctcaaataag tactgtttgt ataccaggat atgtgagatg taaatgtagt   10773
aggtcacttt tcacccttgt agctataaaa taaaaatttt gtagaacaga aatagcttgt   10833
actactgaat taacaaaagt tatactaaag tatcatgttt aaaaaaaata tatatatata   10893
tacagagtta agcttgttgc tgttaccctg tctggatttg aaaagtgtgc tgatttatat   10953
atatatatta cacacacaca cacacacaca cacacacaca cacacacaca cacacacaca   11013
cacacacaca cacacacaca catacaccta aaatggccta aagcagacat ccatgtaatt   11073
acagttgcaa aatgaaaaca ttttggaaag aacattgtat catagttcat tcatttgcag   11133
tggatctttg ttccttttta ctgtggtaat tttagaaatg agtgtcaagt ttgaaattag   11193
atctgctaag ttggggtttt gctgcttgaa ctctgcactg ggtcctcaaa taaaccgatg   11253
tgaatgtagt ttttttccccc tgtgtgaaga agcagttaca ccccaacaat aggaggaaaa   11313
atctagaact atttcaagtt ttatcttttt gtatatgaaa ataaaataat aataaaacaa   11373
```

<210> SEQ ID NO 14
<211> LENGTH: 512
<212> TYPE: PRT
<213> ORGANISM: Homo sapiens

<400> SEQUENCE: 14

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
```

```
            145                 150                 155                 160
Arg His Arg Lys Pro Pro Tyr Gly His Val Asp Ile His Glu Asp Pro
                    165                 170                 175

Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
                    195                 200                 205

Leu Met Asn Asp Phe Val Ala Val Lys Ile Phe Pro Leu Gln Asp Lys
            210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                    245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
                    275                 280                 285

His Val Ala Glu Thr Met Ser Arg Gly Leu Ser Tyr Leu His Glu Asp
            290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                    325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
                    355                 360                 365

Val Leu Glu Gly Ala Ile Asn Phe Gln Arg Asp Ala Phe Leu Arg Ile
            370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                    405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
                    435                 440                 445

Gly Leu Ala Gln Leu Cys Val Thr Ile Glu Glu Cys Trp Asp His Asp
            450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                    485                 490                 495

Val Thr Ser Val Thr Asn Val Asp Leu Pro Pro Lys Glu Ser Ser Ile
            500                 505                 510

<210> SEQ ID NO 15
<211> LENGTH: 2098
<212> TYPE: DNA
<213> ORGANISM: Homo sapiens
<220> FEATURE:
<221> NAME/KEY: CDS
<222> LOCATION: (359)..(1312)

<400> SEQUENCE: 15
```

-continued

```
ttgggaaggg tttccagaag gtgggaaatg tcacctgatt cacactgaac ttttgaaagc      60
tccccacccc caaggagccg cgcacaccct cgctcgcggc cgccctccca cagccccaca     120
cactgggaga ccgcccaccg caaaccgcgg agaccccgt ctagatttaa agcgcggctg      180
cgcccggctt ctgacgtcca ttgaatcgcg cgggcggccg gcggcgagcg cggggctgcg     240
ccgggatcgc tgcgccctcc gccgctggcc tctgcgacgc gcgccgctcg cccgagccac     300
ccgccgccgc gccggctccc cgccgcgctg cgctcctcgc cccgcgcctg ccccccagg     358
```

| atg gtc cgc gcg agg cac cag ccg ggt ggg ctt tgc ctc ctg ctg ctg | 406 |
| Met Val Arg Ala Arg His Gln Pro Gly Gly Leu Cys Leu Leu Leu Leu | |
| 1         5              10             15 | |

| ctg ctc tgc cag ttc atg gag gac cgc agt gcc cag gct ggg aac tgc | 454 |
| Leu Leu Cys Gln Phe Met Glu Asp Arg Ser Ala Gln Ala Gly Asn Cys | |
| 20             25             30 | |

| tgg ctc cgt caa gcg aag aac ggc cgc tgc cag gtc ctg tac aag acc | 502 |
| Trp Leu Arg Gln Ala Lys Asn Gly Arg Cys Gln Val Leu Tyr Lys Thr | |
| 35             40             45 | |

| gaa ctg agc aag gag gag tgc tgc agc acc ggc cgg ctg agc acc tcg | 550 |
| Glu Leu Ser Lys Glu Glu Cys Cys Ser Thr Gly Arg Leu Ser Thr Ser | |
| 50             55             60 | |

| tgg acc gag gag gac gtg aat gac aac aca ctc ttc aag tgg atg att | 598 |
| Trp Thr Glu Glu Asp Val Asn Asp Asn Thr Leu Phe Lys Trp Met Ile | |
| 65             70             75             80 | |

| ttc aac ggg ggc gcc ccc aac tgc atc ccc tgt aaa gaa acg tgt gag | 646 |
| Phe Asn Gly Gly Ala Pro Asn Cys Ile Pro Cys Lys Glu Thr Cys Glu | |
| 85             90             95 | |

| aac gtg gac tgt gga cct ggg aaa aaa tgc cga atg aac aag aag aac | 694 |
| Asn Val Asp Cys Gly Pro Gly Lys Lys Cys Arg Met Asn Lys Lys Asn | |
| 100            105            110 | |

| aaa ccc cgc tgc gtc tgc gcc ccg gat tgt tcc aac atc acc tgg aag | 742 |
| Lys Pro Arg Cys Val Cys Ala Pro Asp Cys Ser Asn Ile Thr Trp Lys | |
| 115            120            125 | |

| ggt cca gtc tgc ggg ctg gat ggg aaa acc tac cgc aat gaa tgt gca | 790 |
| Gly Pro Val Cys Gly Leu Asp Gly Lys Thr Tyr Arg Asn Glu Cys Ala | |
| 130            135            140 | |

| ctc cta aag gca aga tgt aaa gag cag cca gaa ctg gaa gtc cag tac | 838 |
| Leu Leu Lys Ala Arg Cys Lys Glu Gln Pro Glu Leu Glu Val Gln Tyr | |
| 145            150            155            160 | |

| caa ggc aga tgt aaa aag act tgt cgg gat gtt ttc tgt cca ggc agc | 886 |
| Gln Gly Arg Cys Lys Lys Thr Cys Arg Asp Val Phe Cys Pro Gly Ser | |
| 165            170            175 | |

| tcc aca tgt gtg gtg gac cag acc aat aat gcc tac tgt gtg acc tgt | 934 |
| Ser Thr Cys Val Val Asp Gln Thr Asn Asn Ala Tyr Cys Val Thr Cys | |
| 180            185            190 | |

| aat cgg att tgc cca gag cct gct tcc tct gag caa tat ctc tgt ggg | 982 |
| Asn Arg Ile Cys Pro Glu Pro Ala Ser Ser Glu Gln Tyr Leu Cys Gly | |
| 195            200            205 | |

| aat gat gga gtc acc tac tcc agt gcc tgc cac ctg aga aag gct acc | 1030 |
| Asn Asp Gly Val Thr Tyr Ser Ser Ala Cys His Leu Arg Lys Ala Thr | |
| 210            215            220 | |

| tgc ctg ctg ggc aga tct att gga tta gcc tat gag gga aag tgt atc | 1078 |
| Cys Leu Leu Gly Arg Ser Ile Gly Leu Ala Tyr Glu Gly Lys Cys Ile | |
| 225            230            235            240 | |

| aaa gca aag tcc tgt gaa gat atc cag tgc act ggt ggg aaa aaa tgt | 1126 |
| Lys Ala Lys Ser Cys Glu Asp Ile Gln Cys Thr Gly Gly Lys Lys Cys | |
| 245            250            255 | |

| tta tgg gat ttc aag gtt ggg aga ggc cgg tgt tcc ctc tgt gat gag | 1174 |
| Leu Trp Asp Phe Lys Val Gly Arg Gly Arg Cys Ser Leu Cys Asp Glu | |
| 260            265            270 | |

| | | | | | | | | | | | | | | | |
|---|---|---|---|---|---|---|---|---|---|---|---|---|---|---|---|
| ctg | tgc | cct | gac | agt | aag | tcg | gat | gag | cct | gtc | tgt | gcc | agt | gac | aat | 1222 |
| Leu | Cys | Pro | Asp | Ser | Lys | Ser | Asp | Glu | Pro | Val | Cys | Ala | Ser | Asp | Asn | |
| | | 275 | | | | | 280 | | | | | 285 | | | | |

| | | | | | | | | | | | | | | | |
|---|---|---|---|---|---|---|---|---|---|---|---|---|---|---|---|
| gcc | act | tat | gcc | agc | gag | tgt | gcc | atg | aag | gaa | gct | gcc | tgc | tcc | tca | 1270 |
| Ala | Thr | Tyr | Ala | Ser | Glu | Cys | Ala | Met | Lys | Glu | Ala | Ala | Cys | Ser | Ser | |
| | 290 | | | | | 295 | | | | | 300 | | | | | |

| | | | | | | | | | | | | |
|---|---|---|---|---|---|---|---|---|---|---|---|---|
| ggt | gtg | cta | ctg | gaa | gta | aag | cac | tcc | gga | tct | tgc | aac tga | 1312 |
| Gly | Val | Leu | Leu | Glu | Val | Lys | His | Ser | Gly | Ser | Cys | Asn | |
| 305 | | | | 310 | | | | | 315 | | | | |

```
atctgcccgt aaaacctgag ccattgattc ttcagaactt tctgcagttt ttgacttcat    1372
agattatgct ttaaaaaaat ttttttaact tattgcataa cagcagatgc caaaacaaa     1432
aaaagcatct cactgcaagt cacataaaaa tgcaacgctg taatatggct gtatcagagg    1492
gctttgaaaa catacactga gctgcttctg cgctgttgtt gtccgtattt aaacaacagc    1552
tcccctgtat tccccatct agccatttcg gaagacaccg aggaagagga ggaagatgaa     1612
gaccaggact acagctttcc tatatcttct attctagagt ggtaaactct ctataagtgt    1672
tcagtgttga catagccttt gtgcaaaaaa aaaaaaaaaa aaaagaaaaa agaaaaaaag    1732
aaaaatatat tgtccatact gtaaataagt gtatgcttat ttatttgggg ggaaaactat    1792
acattaaagg acctttgtcc taaagctctc tcccaggcca ccttgttact cattggacac    1852
ggagaggcat tcattgtgag gtctactgga tgaggcccat agttgagact tgtagacatt    1912
tatttatact gtgtcatgtt ttataattta acataaaat gtctggttga ctgtatacct     1972
tgttttgaa gaaatttatt cgtgaaagga agagcagttg ttatttattg tgaggtctct     2032
tgcttgtaaa gtaaaagctt tttttccttg taaaccattt aagtccattc cttactattc    2092
actcac                                                                2098
```

<210> SEQ ID NO 16
<211> LENGTH: 317
<212> TYPE: PRT
<213> ORGANISM: Homo sapiens

<400> SEQUENCE: 16

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

```
Gln Gly Arg Cys Lys Lys Thr Cys Arg Asp Val Phe Cys Pro Gly Ser
            165                 170                 175

Ser Thr Cys Val Val Asp Gln Thr Asn Asn Ala Tyr Cys Val Thr Cys
        180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
        290                 295                 300

Gly Val Leu Leu Glu Val Lys His Ser Gly Ser Cys Asn
305                 310                 315

<210> SEQ ID NO 17
<211> LENGTH: 3840
<212> TYPE: DNA
<213> ORGANISM: Homo sapiens
<220> FEATURE:
<221> NAME/KEY: CDS
<222> LOCATION: (176)..(1102)

<400> SEQUENCE: 17
aggagaatgg ggaggagctg gggggcagg caggcgggga aggagaggtc ttaaggggcg      60
gcgaggggag gtcgcatttc ctccgaggct ggcgatcggc ggagctccca cctccgctta    120
cagctcgctg ccgccgtcct gccccgcgcc cccaggagac ctggaccaga ccacg atg    178
                                                                Met
                                                                  1 tgg aaa cgc tgg ctc gcg ctc gcg ctc gcg ctg gtg gcg gtc gcc tgg      226
Trp Lys Arg Trp Leu Ala Leu Ala Leu Ala Leu Val Ala Val Ala Trp
  5                  10                  15 gtc cgc gcc gag gaa gag cta agg agc aaa tcc aag atc tgt gcc aat      274
Val Arg Ala Glu Glu Glu Leu Arg Ser Lys Ser Lys Ile Cys Ala Asn
         20                  25                  30 gtg ttt tgt gga gcc ggc cgg gaa tgt gca gtc aca gag aaa ggg gaa      322
Val Phe Cys Gly Ala Gly Arg Glu Cys Ala Val Thr Glu Lys Gly Glu
     35                  40                  45 ccc acc tgt ctc tgc att gag caa tgc aaa cct cac aag agg cct gtg      370
Pro Thr Cys Leu Cys Ile Glu Gln Cys Lys Pro His Lys Arg Pro Val
 50                  55                  60                  65 tgt ggc agt aat ggc aag acc tac ctc aac cac tgt gaa ctg cat cga      418
Cys Gly Ser Asn Gly Lys Thr Tyr Leu Asn His Cys Glu Leu His Arg
                 70                  75                  80 gat gcc tgc ctc act gga tcc aaa atc cag gtt gat tac gat gga cac      466
Asp Ala Cys Leu Thr Gly Ser Lys Ile Gln Val Asp Tyr Asp Gly His
             85                  90                  95 tgc aaa gag aag aaa tcc gta agt cca tct gcc agc cca gtt gtt tgc      514
Cys Lys Glu Lys Lys Ser Val Ser Pro Ser Ala Ser Pro Val Val Cys
        100                 105                 110 tat cag tcc aac cgt gat gag ctc cga cgt cgc atc atc cag tgg ctg      562
Tyr Gln Ser Asn Arg Asp Glu Leu Arg Arg Arg Ile Ile Gln Trp Leu
```

```
              115                 120                 125
gaa gct gag atc att cca gat ggc tgg ttc tct aaa ggc agc aac tac    610
Glu Ala Glu Ile Ile Pro Asp Gly Trp Phe Ser Lys Gly Ser Asn Tyr
130                 135                 140                 145 agt gaa atc cta gac aag tat ttt aag aac ttt gat aat ggt gat tct    658
Ser Glu Ile Leu Asp Lys Tyr Phe Lys Asn Phe Asp Asn Gly Asp Ser
                150                 155                 160 cgc ctg gac tcc agt gaa ttc ctg aag ttt gtg gaa cag aat gaa act    706
Arg Leu Asp Ser Ser Glu Phe Leu Lys Phe Val Glu Gln Asn Glu Thr
            165                 170                 175 gcc atc aat att aca acg tat cca gac cag gag aac aac aag ttg ctt    754
Ala Ile Asn Ile Thr Thr Tyr Pro Asp Gln Glu Asn Asn Lys Leu Leu
        180                 185                 190 agg gga ctc tgt gtt gat gct ctc att gaa ctg tct gat gaa aat gct    802
Arg Gly Leu Cys Val Asp Ala Leu Ile Glu Leu Ser Asp Glu Asn Ala
    195                 200                 205 gat tgg aaa ctc agc ttc caa gag ttt ctc aag tgc ctc aac cca tct    850
Asp Trp Lys Leu Ser Phe Gln Glu Phe Leu Lys Cys Leu Asn Pro Ser
210                 215                 220                 225 ttc aac cct cct gag aag aag tgt gcc ctg gag gat gaa acg tat gca    898
Phe Asn Pro Pro Glu Lys Lys Cys Ala Leu Glu Asp Glu Thr Tyr Ala
                230                 235                 240 gat gga gct gag acc gag gtg gac tgt aac cgc tgt gtc tgt gcc tgt    946
Asp Gly Ala Glu Thr Glu Val Asp Cys Asn Arg Cys Val Cys Ala Cys
            245                 250                 255 gga aat tgg gtc tgt aca gcc atg acc tgt gac gga aag aat cag aag    994
Gly Asn Trp Val Cys Thr Ala Met Thr Cys Asp Gly Lys Asn Gln Lys
        260                 265                 270 ggg gcc cag acc cag aca gag gag gag atg acc aga tat gtc cag gag    1042
Gly Ala Gln Thr Gln Thr Glu Glu Glu Met Thr Arg Tyr Val Gln Glu
    275                 280                 285 ctc caa aag cat cag gaa aca gct gaa aag acc aag aga gtg agc acc    1090
Leu Gln Lys His Gln Glu Thr Ala Glu Lys Thr Lys Arg Val Ser Thr
290                 295                 300                 305 aaa gag atc taa tgaggaggca cagaccagtg tctggatccc agcatcttct        1142
Lys Glu Ile ccacttcagc gctgagttca gtatacacaa gtgtctgcta cagtcgccaa atcaccagta  1202
tttgcttata tagcaatgag tttttatttt tttatttgtt ttgcaataaa ggatatgaag  1262
gtggctggct aggaagggaa gggccacagc cttcatttct aggagtgctt taagagaaac  1322
tgtaaatggt gctctgggc tggaggctag taaggaaact gcatcacgat gaaagagga   1382 acagacccaa atctgaacct cttttgagtt tactgcatct gtcagcaggc tgcagggagt  1442
gcacacgatg ccagagagaa cttagcaggg tgtccccgga ggagaggttt gggaagctcc  1502
acggagagga acgctctctg cttccagcct ctttccattg ccgtcagcat gacagacctc  1562
cagcatccac gcatctcttg gtcccaataa ctgcctctag atacatagcc atactgctag  1622
ttaacccagt gtccctcaga cttggatgga gtttctggga gggtacaccc aaatgatgca  1682
gatacttgta tactttgagc cccttagcga cctaaccaaa ttttaaaaat acttttttacc 1742 aaaggtgcta tttctctgta aaacactttt ttttggcaag ttgactttat tcttcaatta  1802
ttatcattat attattgttt tttaatattt tattttcttg actaggtatt aagcttttgt  1862
aattattttt cagtagtccc accacttcat aggtggaagg agtttggggt tcttcctggt  1922
gcaggggctg aaataaccca gatgccccca ccctgccaca tactagatgc agcccatagt  1982 tggccccccct agcttccagc agtccactat ctgccagagg agcaagggtg ccttagaccg  2042
```

| | |
|---|---|
| aagccagggg aagaagcatc ttcataaaaa actttcaaga tccaaacatt aatttgtttt | 2102 |
| tatttattct gagaagttga ggcaaatcag tattcccaag gatggcgaca agggcagcca | 2162 |
| agcagggctt aggatatccc agcctaccaa tatgctcatt cgactaacta ggagggtgag | 2222 |
| ttggccctgt ctcttctttt ttctggacct cagtttcctc agtgagctgg taagaatgca | 2282 |
| ctaaccttt gatttgataa gttataaatt ctgtggttct gatcattggt ccagagggga | 2342 |
| gataggttcc tgtgattttt ccttcttctc tatagaataa atgaaatctt gttactagaa | 2402 |
| caagaaatgt cagatggcca aaacaagat gaccagattt gatctcagcc tgatgaccct | 2462 |
| acaggtcgtg ctatgatatg gagtcctcat gggtaaagca ggaagagagt gggaaagaga | 2522 |
| accaccccac tctgtcttca tatttgcatt tcatgtttaa cctccggctg gaaatagaaa | 2582 |
| gcattccctt agagatgagg ataaaagaaa gtttcagatt caacaggggg aagaaaatgg | 2642 |
| agatttaatc ctaaaactgt gacttgggga ggtcagtcat ttacagttag tcctgtgtct | 2702 |
| ttcgacttct gtgattatta accccactca ctaccctgtt tcagatgcat ttggaatacc | 2762 |
| aaagattaaa tccttgacat aagatctcat ttgcagaaag cagattaaag accatcagaa | 2822 |
| ggaaattatt taggttgtaa tgcacaggca actgtgagaa actgttgtgc caaaaataga | 2882 |
| attccttcta gtttttcttg ttctcatttg aaaggagaaa attccacttt gtttagcatt | 2942 |
| tcaagctttt atgtatccat cccatctaaa aactcttcaa actccacttg ttcagtctga | 3002 |
| aatgcagctc cctgtccaag tgccttggag aactcacagc agcacgcctt aatcaaaggt | 3062 |
| tttaccagcc cttggacact atgggaggag ggcaagagta caccaatttg ttaaaagcaa | 3122 |
| gaaaccacag tgtctcttca ctagtcattt agaaacatggt tatcatccaa gactactcta | 3182 |
| ccctgcaaca ttgaactccc aagagcaaat ccacattcct cttgagttct gcagcttctg | 3242 |
| tgtaaatagg gcagctgtcg tctatgccgt agaatcacat gatctgagga ccattcatgg | 3302 |
| aagctgctaa atagcctagt ctggggagtc ttccataaag ttttgcatgg agcaaacaaa | 3362 |
| caggattaaa ctaggtttgg ttccttcagc cctctaaaag catagggctt agcctgcagg | 3422 |
| cttccttggg ctttctctgt gtgtgtagtt ttgtaaacac tatagcatct gttaagatcc | 3482 |
| agtgtccatg gaaacattcc cacatgccgt gactctggac tatatcagtt tttggaaagc | 3542 |
| agggttcctc tgcctgctaa caagcccacg tggaccagtc tgaatgtctt tcctttacac | 3602 |
| ctatgttttt aagtagtcaa acttcaagaa acaatctaaa caagtttctg ttgcatatgt | 3662 |
| gtttgtgaac ttgtatttgt atttagtagg cttctatatt gcatttaact tgttttgta | 3722 |
| actcctgatt cttccttttc ggatactatt gatgaataaa gaaattaaag tgatggtttt | 3782 |
| attggtttcc tttcccccaa ttaaggccaa ataaagtcgt gagaacatta cccattta | 3840 |

<210> SEQ ID NO 18
<211> LENGTH: 308
<212> TYPE: PRT
<213> ORGANISM: Homo sapiens

<400> SEQUENCE: 18

Met Trp Lys Arg Trp Leu Ala Leu Ala Leu Ala Leu Val Ala Val Ala
1               5                   10                  15

Trp Val Arg Ala Glu Glu Glu Leu Arg Ser Lys Ser Lys Ile Cys Ala
                20                  25                  30

Asn Val Phe Cys Gly Ala Gly Arg Glu Cys Ala Val Thr Glu Lys Gly
            35                  40                  45

Glu Pro Thr Cys Leu Cys Ile Glu Gln Cys Lys Pro His Lys Arg Pro
        50                  55                  60

```
Val Cys Gly Ser Asn Gly Lys Thr Tyr Leu Asn His Cys Glu Leu His
 65                  70                  75                  80

Arg Asp Ala Cys Leu Thr Gly Ser Lys Ile Gln Val Asp Tyr Asp Gly
                 85                  90                  95

His Cys Lys Glu Lys Lys Ser Val Ser Pro Ser Ala Ser Pro Val Val
            100                 105                 110

Cys Tyr Gln Ser Asn Arg Asp Glu Leu Arg Arg Ile Ile Gln Trp
        115                 120                 125

Leu Glu Ala Glu Ile Ile Pro Asp Gly Trp Phe Ser Lys Gly Ser Asn
    130                 135                 140

Tyr Ser Glu Ile Leu Asp Lys Tyr Phe Lys Asn Phe Asp Asn Gly Asp
145                 150                 155                 160

Ser Arg Leu Asp Ser Ser Glu Phe Leu Lys Phe Val Glu Gln Asn Glu
                165                 170                 175

Thr Ala Ile Asn Ile Thr Thr Tyr Pro Asp Gln Glu Asn Asn Lys Leu
            180                 185                 190

Leu Arg Gly Leu Cys Val Asp Ala Leu Ile Glu Leu Ser Asp Glu Asn
        195                 200                 205

Ala Asp Trp Lys Leu Ser Phe Gln Glu Phe Leu Lys Cys Leu Asn Pro
    210                 215                 220

Ser Phe Asn Pro Pro Glu Lys Lys Cys Ala Leu Glu Asp Glu Thr Tyr
225                 230                 235                 240

Ala Asp Gly Ala Glu Thr Glu Val Asp Cys Asn Arg Cys Val Cys Ala
                245                 250                 255

Cys Gly Asn Trp Val Cys Thr Ala Met Thr Cys Asp Gly Lys Asn Gln
            260                 265                 270

Lys Gly Ala Gln Thr Gln Thr Glu Glu Glu Met Thr Arg Tyr Val Gln
        275                 280                 285

Glu Leu Gln Lys His Gln Glu Thr Ala Glu Lys Thr Lys Arg Val Ser
    290                 295                 300

Thr Lys Glu Ile
305

<210> SEQ ID NO 19
<211> LENGTH: 2525
<212> TYPE: DNA
<213> ORGANISM: Homo sapiens
<220> FEATURE:
<221> NAME/KEY: CDS
<222> LOCATION: (36)..(827)

<400> SEQUENCE: 19
gggaagtcgg tgccgctgcc gtctctgcgt tcgcc atg cgt ccc ggg gcg cca        53
                                       Met Arg Pro Gly Ala Pro
                                         1               5 ggg cca ctc tgg cct ctg ccc tgg ggg gcc ctg gct tgg gcc gtg ggc      101
Gly Pro Leu Trp Pro Leu Pro Trp Gly Ala Leu Ala Trp Ala Val Gly
         10                  15                  20 ttc gtg agc tcc atg ggc tcg ggg aac ccc gcg ccc ggt ggt gtt tgc      149
Phe Val Ser Ser Met Gly Ser Gly Asn Pro Ala Pro Gly Gly Val Cys
             25                  30                  35 tgg ctc cag cag ggc cag gag gcc acc tgc agc ctg gtg ctc cag act      197
Trp Leu Gln Gln Gly Gln Glu Ala Thr Cys Ser Leu Val Leu Gln Thr
     40                  45                  50 gat gtc acc cgg gcc gag tgc tgt gcc tcc ggc aac att gac acc gcc      245
Asp Val Thr Arg Ala Glu Cys Cys Ala Ser Gly Asn Ile Asp Thr Ala
 55                  60                  65                  70
```

| | | |
|---|---|---|
| tgg tcc aac ctc acc cac ccg ggg aac aag atc aac ctc ctc ggc ttc<br>Trp Ser Asn Leu Thr His Pro Gly Asn Lys Ile Asn Leu Leu Gly Phe<br>75 80 85 | | 293 |
| ttg ggc ctt gtc cac tgc ctt ccc tgc aaa gat tcg tgc gac ggc gtg<br>Leu Gly Leu Val His Cys Leu Pro Cys Lys Asp Ser Cys Asp Gly Val<br>90 95 100 | | 341 |
| gag tgc ggc ccg ggc aag gcg tgc cgc atg ctg ggg ggc cgc ccg cgc<br>Glu Cys Gly Pro Gly Lys Ala Cys Arg Met Leu Gly Gly Arg Pro Arg<br>105 110 115 | | 389 |
| tgc gag tgc gcg ccc gac tgc tcg ggg ctc ccg gcg cgg ctg cag gtc<br>Cys Glu Cys Ala Pro Asp Cys Ser Gly Leu Pro Ala Arg Leu Gln Val<br>120 125 130 | | 437 |
| tgc ggc tca gac ggc gcc acc tac cgc gac gag tgc gag ctg cgc gcc<br>Cys Gly Ser Asp Gly Ala Thr Tyr Arg Asp Glu Cys Glu Leu Arg Ala<br>135 140 145 150 | | 485 |
| gcg cgc tgc cgc ggc cac ccg gac ctg agc gtc atg tac cgg ggc cgc<br>Ala Arg Cys Arg Gly His Pro Asp Leu Ser Val Met Tyr Arg Gly Arg<br>155 160 165 | | 533 |
| tgc cgc aag tcc tgt gag cac gtg gtg tgc ccg cgg cca cag tcg tgc<br>Cys Arg Lys Ser Cys Glu His Val Val Cys Pro Arg Pro Gln Ser Cys<br>170 175 180 | | 581 |
| gtc gtg gac cag acg ggc agc gcc cac tgc gtg gtg tgt cga gcg gcg<br>Val Val Asp Gln Thr Gly Ser Ala His Cys Val Val Cys Arg Ala Ala<br>185 190 195 | | 629 |
| ccc tgc cct gtg ccc tcc agc ccc ggc cag gag ctt tgc ggc aac aac<br>Pro Cys Pro Val Pro Ser Ser Pro Gly Gln Glu Leu Cys Gly Asn Asn<br>200 205 210 | | 677 |
| aac gtc acc tac atc tcc tcg tgc cac atg cgc cag gcc acc tgc ttc<br>Asn Val Thr Tyr Ile Ser Ser Cys His Met Arg Gln Ala Thr Cys Phe<br>215 220 225 230 | | 725 |
| ctg ggc cgc tcc atc ggc gtg cgc cac gcg ggc agc tgc gca ggc acc<br>Leu Gly Arg Ser Ile Gly Val Arg His Ala Gly Ser Cys Ala Gly Thr<br>235 240 245 | | 773 |
| cct gag gag ccg cca ggt ggt gag tct gca gaa gag gaa gag aac ttc<br>Pro Glu Glu Pro Pro Gly Gly Glu Ser Ala Glu Glu Glu Glu Asn Phe<br>250 255 260 | | 821 |
| gtg tga gcctgcagga caggcctggg cctggtgccc gaggcccccc atcatcccct<br>Val | | 877 |
| gttatttatt gccacagcag agtctaattt atatgccacg dacactcctt agagcccgga | | 937 |
| ttcggaccac ttggggatcc cagaacctcc ctgacgatat cctggaagga ctgaggaagg | | 997 |
| gaggcctggg ggccggctgg tgggtgggat agacctgcgt tccggacact gagcgcctga | | 1057 |
| tttagggccc ttctctagga tgccccagcc cctaccctaa gacctattgc cggggaggat | | 1117 |
| tccacacttc cgctcctttg gggataaacc tattaattat tgctactatc aagagggctg | | 1177 |
| ggcattctct gctggtaatt cctgaagagg catgactgct tttctcagcc ccaagcctct | | 1237 |
| agtctgggtg tgtacggagg gtctagcctg gtgtgtacg gagggtctag cctgggtgag | | 1297 |
| tacgagggt ctagcctggg tgagtacgga gggtctagcc tgggtgagta cggagggtct | | 1357 |
| agcctgggtg tgtatggagg atctagcctg ggtgagtatg gagggtctag cctgggtgag | | 1417 |
| tatgagggt ctagcctggg tgtgtatgga gggtctagcc tgggtgagta tggagggtct | | 1477 |
| agcctgggtg tgtatggagg gtctagcctg ggtgagtatg gagggtctag cctggtgtg | | 1537 |
| tacgagggt ctagtctgag tgcgtgtggg gacctcagaa cactgtgacc ttagcccagc | | 1597 |
| aagccaggcc cttcatgaag gccaagaagg ctgccaccat tccctgccag cccaagaact | | 1657 |
| ccagcttccc cactgcctct gtgtgcccct ttgcgtcctg tgaaggccat tgagaaatgc | | 1717 |

```
ccagtgtgcc ccctgggaaa gggcacggcc tgtgctcctg acacgggctg tgcttggcca      1777
cagaaccacc cagcgtctcc cctgctgctg tccacgtcag ttcatgaggc aacgtcgcgt      1837
ggtctcagac gtggagcagc cagcggcagc tcagagcagg gcactgtgtc cggcggagcc      1897
aagtccactc tgggggagct ctggcgggga ccacgggcca ctgctcaccc actggccccg      1957 agggggggtgt agacgccaag actcacgcat gtgtgacatc cggagtcctg gagccgggtg      2017
tcccagtggc accactaggt gcctgctgcc tccacagtgg ggttcacacc cagggctcct      2077
tggtccccca caacctgccc cggccaggcc tgcagaccca gactccagcc agacctgcct      2137
cacccaccaa tgcagccggg gctggcgaca ccagccaggt gctggtcttg ggccagttct      2197
cccacgacgg ctcaccctcc cctccatctg cgttgatgct cagaatcgcc tacctgtgcc      2257
tgcgtgtaaa ccacagcctc agaccagcta tggggagagg acaacacgga ggatatccag      2317
cttccccggt ctggggtgag gaatgtgggg agcttgggca tcctcctcca gcctcctcca      2377
gcccccaggc agtgccttac ctgtggtgcc cagaaaagtg cccctaggtt ggtgggtcta      2437
caggagcctc agccaggcag cccacccac cctggggccc tgcctcacca aggaaataaa      2497
gactcaagcc atttaaaaaa aaaaaaaa                                         2525

<210> SEQ ID NO 20
<211> LENGTH: 263
<212> TYPE: PRT
<213> ORGANISM: Homo sapiens

<400> SEQUENCE: 20

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Pro Val Pro Ser Ser Pro Gly Gln
        195                 200                 205

Glu Leu Cys Gly Asn Asn Asn Val Thr Tyr Ile Ser Ser Cys His Met
    210                 215                 220
```

```
Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
                245                 250                 255

Glu Glu Glu Glu Asn Phe Val
            260

<210> SEQ ID NO 21
<211> LENGTH: 2881
<212> TYPE: DNA
<213> ORGANISM: Homo sapiens
<220> FEATURE:
<221> NAME/KEY: CDS
<222> LOCATION: (250)..(1779)

<400> SEQUENCE: 21
ctgcagcgcc cggctgcctc gcactccgcc tccccccggct cagcccccgg ccgcggcggg        60
acccgagcct ggagcattgg taagcgtcac actgccaaag tgagagctgc tggagaactc       120
ataatcccag gaacgcctct tctactctcc gagtacccca gtgaccagag tgagagaagc       180
tctgaacgag ggcacgcggc ttgaaggact gtgggcagat gtgaccaaga gcctgcatta       240 agttgtaca atg gta gat gga gtg atg att ctt cct gtg ctt atc atg att       291
          Met Val Asp Gly Val Met Ile Leu Pro Val Leu Ile Met Ile
            1               5                  10 gct ctc ccc tcc cct agt atg gaa gat gag aag ccc aag gtc aac ccc         339
Ala Leu Pro Ser Pro Ser Met Glu Asp Glu Lys Pro Lys Val Asn Pro
 15                  20                  25                  30 aaa ctc tac atg tgt gtg tgt gaa ggt ctc tcc tgc ggt aat gag gac         387
Lys Leu Tyr Met Cys Val Cys Glu Gly Leu Ser Cys Gly Asn Glu Asp
                 35                  40                  45 cac tgt gaa ggc cag cag tgc ttt tcc tca ctg agc atc aac gat ggc         435
His Cys Glu Gly Gln Gln Cys Phe Ser Ser Leu Ser Ile Asn Asp Gly
             50                  55                  60 ttc cac gtc tac cag aaa ggc tgc ttc cag gtt tat gag cag gga aag         483
Phe His Val Tyr Gln Lys Gly Cys Phe Gln Val Tyr Glu Gln Gly Lys
         65                  70                  75 atg acc tgt aag acc ccg ccg tcc cct ggc caa gcc gtg gag tgc tgc         531
Met Thr Cys Lys Thr Pro Pro Ser Pro Gly Gln Ala Val Glu Cys Cys
     80                  85                  90 caa ggg gac tgg tgt aac agg aac atc acg gcc cag ctg ccc act aaa         579
Gln Gly Asp Trp Cys Asn Arg Asn Ile Thr Ala Gln Leu Pro Thr Lys
 95                 100                 105                 110 gga aaa tcc ttc cct gga aca cag aat ttc cac ttg gag gtt ggc ctc         627
Gly Lys Ser Phe Pro Gly Thr Gln Asn Phe His Leu Glu Val Gly Leu
                115                 120                 125 att att ctc tct gta gtg ttc gca gta tgt ctt tta gcc tgc ctg ctg         675
Ile Ile Leu Ser Val Val Phe Ala Val Cys Leu Leu Ala Cys Leu Leu
            130                 135                 140 gga gtt gct ctc cga aaa ttt aaa agg cgc aac caa gaa cgc ctc aat         723
Gly Val Ala Leu Arg Lys Phe Lys Arg Arg Asn Gln Glu Arg Leu Asn
        145                 150                 155 ccc cga gac gtg gag tat ggc act atc gaa ggg ctc atc acc acc aat         771
Pro Arg Asp Val Glu Tyr Gly Thr Ile Glu Gly Leu Ile Thr Thr Asn
    160                 165                 170 gtt gga gac agc act tta gca gat tta ttg gat cat tcg tgt aca tca         819
Val Gly Asp Ser Thr Leu Ala Asp Leu Leu Asp His Ser Cys Thr Ser
175                 180                 185                 190 gga agt ggc tct ggt ctt cct ttt ctg gta caa aga aca gtg gct cgc         867
Gly Ser Gly Ser Gly Leu Pro Phe Leu Val Gln Arg Thr Val Ala Arg
                195                 200                 205
```

```
cag att aca ctg ttg gag tgt gtc ggg aaa ggc agg tat ggt gag gtg    915
Gln Ile Thr Leu Leu Glu Cys Val Gly Lys Gly Arg Tyr Gly Glu Val
            210                 215                 220 tgg agg ggc agc tgg caa ggg gag aat gtt gcc gtg aag atc ttc tcc    963
Trp Arg Gly Ser Trp Gln Gly Glu Asn Val Ala Val Lys Ile Phe Ser
                225                 230                 235 tcc cgt gat gag aag tca tgg ttc agg gaa acg gaa ttg tac aac act   1011
Ser Arg Asp Glu Lys Ser Trp Phe Arg Glu Thr Glu Leu Tyr Asn Thr
        240                 245                 250 gtg atg ctg agg cat gaa aat atc tta ggt ttc att gct tca gac atg   1059
Val Met Leu Arg His Glu Asn Ile Leu Gly Phe Ile Ala Ser Asp Met
255                 260                 265                 270 aca tca aga cac tcc agt acc cag ctg tgg tta att aca cat tat cat   1107
Thr Ser Arg His Ser Ser Thr Gln Leu Trp Leu Ile Thr His Tyr His
                275                 280                 285 gaa atg gga tcg ttg tac gac tat ctt cag ctt act act ctg gat aca   1155
Glu Met Gly Ser Leu Tyr Asp Tyr Leu Gln Leu Thr Thr Leu Asp Thr
        290                 295                 300 gtt agc tgc ctt cga ata gtg ctg tcc ata gct agt ggt ctt gca cat   1203
Val Ser Cys Leu Arg Ile Val Leu Ser Ile Ala Ser Gly Leu Ala His
                305                 310                 315 ttg cac ata gag ata ttt ggg acc caa ggg aaa cca gcc att gcc cat   1251
Leu His Ile Glu Ile Phe Gly Thr Gln Gly Lys Pro Ala Ile Ala His
320                 325                 330 cga gat tta aag agc aaa aat att ctg gtt aag aag aat gga cag tgt   1299
Arg Asp Leu Lys Ser Lys Asn Ile Leu Val Lys Lys Asn Gly Gln Cys
335                 340                 345                 350 tgc ata gca gat ttg ggc ctg gca gtc atg cat tcc cag agc acc aat   1347
Cys Ile Ala Asp Leu Gly Leu Ala Val Met His Ser Gln Ser Thr Asn
                355                 360                 365 cag ctt gat gtg ggg aac aat ccc cgt gtg ggc acc aag cgc tac atg   1395
Gln Leu Asp Val Gly Asn Asn Pro Arg Val Gly Thr Lys Arg Tyr Met
        370                 375                 380 gcc ccc gaa gtt cta gat gaa acc atc cag gtg gat tgt ttc gat tct   1443
Ala Pro Glu Val Leu Asp Glu Thr Ile Gln Val Asp Cys Phe Asp Ser
                385                 390                 395 tat aaa agg gtc gat att tgg gcc ttt gga ctt gtt ttg tgg gaa gtg   1491
Tyr Lys Arg Val Asp Ile Trp Ala Phe Gly Leu Val Leu Trp Glu Val
        400                 405                 410 gcc agg cgg atg gtg agc aat ggt ata gtg gag gat tac aag cca ccg   1539
Ala Arg Arg Met Val Ser Asn Gly Ile Val Glu Asp Tyr Lys Pro Pro
415                 420                 425                 430 ttc tac gat gtg gtt ccc aat gac cca agt ttt gaa gat atg agg aag   1587
Phe Tyr Asp Val Val Pro Asn Asp Pro Ser Phe Glu Asp Met Arg Lys
                435                 440                 445 gta gtc tgt gtg gat caa caa agg cca aac ata ccc aac aga tgg ttc   1635
Val Val Cys Val Asp Gln Gln Arg Pro Asn Ile Pro Asn Arg Trp Phe
        450                 455                 460 tca gac ccg aca tta acc tct ctg gcc aag cta atg aaa gaa tgc tgg   1683
Ser Asp Pro Thr Leu Thr Ser Leu Ala Lys Leu Met Lys Glu Cys Trp
                465                 470                 475 tat caa aat cca tcc gca aga ctc aca gca ctg cgt atc aaa aag act   1731
Tyr Gln Asn Pro Ser Ala Arg Leu Thr Ala Leu Arg Ile Lys Lys Thr
        480                 485                 490 ttg acc aaa att gat aat tcc ctc gac aaa ttg aaa act gac tgt tga   1779
Leu Thr Lys Ile Asp Asn Ser Leu Asp Lys Leu Lys Thr Asp Cys
495                 500                 505 cattttcata gtgtcaagaa ggaagatttg acgttgttgt cattgtccag ctgggaccta   1839
```

```
atgctggcct gactggttgt cagaatggaa tccatctgtc tccctcccca aatggctgct    1899
ttgacaaggc agacgtcgta cccagccatg tgttggggag acatcaaaac caccctaacc    1959
tcgctcgatg actgtgaact gggcatttca cgaactgttc acactgcaga gactaatgtt    2019
ggacagacac tgttgcaaag gtagggactg gaggaacaca gagaaatcct aaaagagatc    2079
tgggcattaa gtcagtggct tgcatagct ttcacaagtc tcctagacac tccccacggg    2139
aaactcaagg aggtggtgaa ttttaatca gcaatattgc ctgtgcttct cttctttatt    2199
gcactaggaa ttcttttgcat tccttacttg cactgttact cttaatttta aagacccaac    2259
ttgccaaaat gttggctgcg tactccactg gtctgtcttt ggataatagg aattcaattt    2319
ggcaaaacaa aatgtaatgt cagactttgc tgcatttttac acatgtgctg atgtttacaa    2379
tgatgccgaa cattaggaat tgtttataca aactttgca aattatttat tacttgtgca    2439
cttagtagtt tttacaaaac tgctttgtgc atatgttaaa gcttattttt atgtggtctt    2499
atgattttat tacagaaatg ttttaacac tatactctaa aatggacatt ttcttttatt    2559
atcagttaaa atcacatttt aagtgcttca catttgtatg tgtgtagact gtaacttttt    2619
ttcagttcat atgcagaacg tatttagcca ttacccacgt gacaccaccg aatatattac    2679
tgatttagaa gcaaagattt cagtagaatt ttagtcctga acgctacggg gaaaatgcat    2739
tttcttcaga attatccatt acgtgcattt aaactctgcc agaaaaaaat aactattttg    2799
ttttaatcta cttttttgtat ttagtagtta tttgtataaa ttaaataaac tgttttcaag    2859
tcaaaaaaaa aaaaaaaaaa aa                                             2881
```

<210> SEQ ID NO 22
<211> LENGTH: 509
<212> TYPE: PRT
<213> ORGANISM: Homo sapiens

<400> SEQUENCE: 22

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190
```

```
Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 23
<211> LENGTH: 4564
<212> TYPE: DNA
<213> ORGANISM: Homo sapiens
<220> FEATURE:
<221> NAME/KEY: CDS
<222> LOCATION: (78)..(1595)

<400> SEQUENCE: 23
ggggaggcgc cggggggcgcg cgcgcgcgcg ctgggcgctg ctgggctgcg gcggcggcgg      60
cggcggcggt ggttact atg gcg gag tcg gcc gga gcc tcc tcc ttc ttc        110
                Met Ala Glu Ser Ala Gly Ala Ser Ser Phe Phe
                 1               5                  10 ccc ctt gtt gtc ctc ctg ctc gcc ggc agc ggc ggg tcc ggg ccc cgg      158
```

-continued

|  |  |
|---|---|
| Pro Leu Val Val Leu Leu Leu Ala Gly Ser Gly Ser Gly Pro Arg<br>15               20               25 | |
| ggg gtc cag gct ctg ctg tgt gcg tgc acc agc tgc ctc cag gcc aac<br>Gly Val Gln Ala Leu Leu Cys Ala Cys Thr Ser Cys Leu Gln Ala Asn<br>     30                  35               40 | 206 |
| tac acg tgt gag aca gat ggg gcc tgc atg gtt tcc att ttc aat ctg<br>Tyr Thr Cys Glu Thr Asp Gly Ala Cys Met Val Ser Ile Phe Asn Leu<br>45               50               55 | 254 |
| gat ggg atg gag cac cat gtg cgc acc tgc atc ccc aaa gtg gag ctg<br>Asp Gly Met Glu His His Val Arg Thr Cys Ile Pro Lys Val Glu Leu<br>60               65               70               75 | 302 |
| gtc cct gcc ggg aag ccc ttc tac tgc ctg agc tcg gag gac ctg cgc<br>Val Pro Ala Gly Lys Pro Phe Tyr Cys Leu Ser Ser Glu Asp Leu Arg<br>           80                   85               90 | 350 |
| aac acc cac tgc tgc tac act gac tac tgc aac agg atc gac ttg agg<br>Asn Thr His Cys Cys Tyr Thr Asp Tyr Cys Asn Arg Ile Asp Leu Arg<br>               95               100           105 | 398 |
| gtg ccc agt ggt cac ctc aag gag cct gag cac ccg tcc atg tgg ggc<br>Val Pro Ser Gly His Leu Lys Glu Pro Glu His Pro Ser Met Trp Gly<br>           110                 115               120 | 446 |
| ccg gtg gag ctg gta ggc atc atc gcc ggc ccg gtg ttc ctc ctg ttc<br>Pro Val Glu Leu Val Gly Ile Ile Ala Gly Pro Val Phe Leu Leu Phe<br>125               130               135 | 494 |
| ctc atc atc atc att gtt ttc ctt gtc att aac tat cat cag cgt gtc<br>Leu Ile Ile Ile Ile Val Phe Leu Val Ile Asn Tyr His Gln Arg Val<br>140               145               150             155 | 542 |
| tat cac aac cgc cag aga ctg gac atg gaa gat ccc tca tgt gag atg<br>Tyr His Asn Arg Gln Arg Leu Asp Met Glu Asp Pro Ser Cys Glu Met<br>                     160               165               170 | 590 |
| tgt ctc tcc aaa gac aag acg ctc cag gat ctt gtc tac gat ctc tcc<br>Cys Leu Ser Lys Asp Lys Thr Leu Gln Asp Leu Val Tyr Asp Leu Ser<br>               175                 180             185 | 638 |
| acc tca ggg tct ggc tca ggg tta ccc ctc ttt gtc cag cgc aca gtg<br>Thr Ser Gly Ser Gly Ser Gly Leu Pro Leu Phe Val Gln Arg Thr Val<br>           190                 195               200 | 686 |
| gcc cga acc atc gtt tta caa gag att att ggc aag ggt cgg ttt ggg<br>Ala Arg Thr Ile Val Leu Gln Glu Ile Ile Gly Lys Gly Arg Phe Gly<br>205               210               215 | 734 |
| gaa gta tgg cgg ggc cgc tgg agg ggt ggt gat gtg gct gtg aaa ata<br>Glu Val Trp Arg Gly Arg Trp Arg Gly Gly Asp Val Ala Val Lys Ile<br>220               225               230             235 | 782 |
| ttc tct tct cgt gaa gaa cgg tct tgg ttc agg gaa gca gag ata tac<br>Phe Ser Ser Arg Glu Glu Arg Ser Trp Phe Arg Glu Ala Glu Ile Tyr<br>               240                 245             250 | 830 |
| cag acg gtc atg ctg cgc cat gaa aac atc ctt gga ttt att gct gct<br>Gln Thr Val Met Leu Arg His Glu Asn Ile Leu Gly Phe Ile Ala Ala<br>255               260               265 | 878 |
| gac aat aaa gat aat ggc acc tgg aca cag ctg tgg ctt gtt tct gac<br>Asp Asn Lys Asp Asn Gly Thr Trp Thr Gln Leu Trp Leu Val Ser Asp<br>270               275               280 | 926 |
| tat cat gag cac ggg tcc ctg ttt gat tat ctg aac cgg tac aca gtg<br>Tyr His Glu His Gly Ser Leu Phe Asp Tyr Leu Asn Arg Tyr Thr Val<br>           285                 290               295 | 974 |
| aca att gag ggg atg att aag ctg gcc ttg tct gct gct agt ggg ctg<br>Thr Ile Glu Gly Met Ile Lys Leu Ala Leu Ser Ala Ala Ser Gly Leu<br>300               305               310             315 | 1022 |
| gca cac ctg cac atg gag atc gtg ggc acc caa ggg aag cct gga att<br>Ala His Leu His Met Glu Ile Val Gly Thr Gln Gly Lys Pro Gly Ile<br>               320                 325             330 | 1070 |

| | | |
|---|---|---|
| gct cat cga gac tta aag tca aag aac att ctg gtg aag aaa aat ggc<br>Ala His Arg Asp Leu Lys Ser Lys Asn Ile Leu Val Lys Lys Asn Gly<br>335 340 345 | | 1118 |
| atg tgt gcc ata gca gac ctg ggc ctg gct gtc cgt cat gat gca gtc<br>Met Cys Ala Ile Ala Asp Leu Gly Leu Ala Val Arg His Asp Ala Val<br>350 355 360 | | 1166 |
| act gac acc att gac att gcc ccg aat cag agg gtg ggg acc aaa cga<br>Thr Asp Thr Ile Asp Ile Ala Pro Asn Gln Arg Val Gly Thr Lys Arg<br>365 370 375 | | 1214 |
| tac atg gcc cct gaa gta ctt gat gaa acc att aat atg aaa cac ttt<br>Tyr Met Ala Pro Glu Val Leu Asp Glu Thr Ile Asn Met Lys His Phe<br>380 385 390 395 | | 1262 |
| gac tcc ttt aaa tgt gct gat att tat gcc ctc ggg ctt gta tat tgg<br>Asp Ser Phe Lys Cys Ala Asp Ile Tyr Ala Leu Gly Leu Val Tyr Trp<br>400 405 410 | | 1310 |
| gag att gct cga aga tgc aat tct gga gga gtc cat gaa gaa tat cag<br>Glu Ile Ala Arg Arg Cys Asn Ser Gly Gly Val His Glu Glu Tyr Gln<br>415 420 425 | | 1358 |
| ctg cca tat tac gac tta gtg ccc tct gac cct tcc att gag gaa atg<br>Leu Pro Tyr Tyr Asp Leu Val Pro Ser Asp Pro Ser Ile Glu Glu Met<br>430 435 440 | | 1406 |
| cga aag gtt gta tgt gat cag aag ctg cgt ccc aac atc ccc aac tgg<br>Arg Lys Val Val Cys Asp Gln Lys Leu Arg Pro Asn Ile Pro Asn Trp<br>445 450 455 | | 1454 |
| tgg cag agt tat gag gca ctg cgg gtg atg ggg aag atg atg cga gag<br>Trp Gln Ser Tyr Glu Ala Leu Arg Val Met Gly Lys Met Met Arg Glu<br>460 465 470 475 | | 1502 |
| tgt tgg tat gcc aac ggc gca gcc cgc ctg acg gcc ctg cgc atc aag<br>Cys Trp Tyr Ala Asn Gly Ala Ala Arg Leu Thr Ala Leu Arg Ile Lys<br>480 485 490 | | 1550 |
| aag acc ctc tcc cag ctc agc gtg cag gaa gac gtg aag atc taa<br>Lys Thr Leu Ser Gln Leu Ser Val Gln Glu Asp Val Lys Ile<br>495 500 505 | | 1595 |
| ctgctccctc tctccacacg gagctcctgg cagcgagaac tacgcacagc tgccgcgttg | | 1655 |
| agcgtacgat ggaggcctac ctctcgtttc tgcccagccc tctgtggcca ggagccctgg | | 1715 |
| cccgcaagag ggacagagcc cgggagagac tcgctcactc ccatgttggg tttgagacag | | 1775 |
| acaccttttc tatttaccct ctaatggcat ggagactctg agagcgaatt gtgtggagaa | | 1835 |
| ctcagtgcca cacctcgaac tggttgtagt gggaagtccc gcgaaacccg gtgcatctgg | | 1895 |
| cacgtggcca ggagccatga caggggcgct tgggaggggc cggaggaacc gaggtgttgc | | 1955 |
| cagtgctaag ctgccctgag ggtttccttc ggggaccagc ccacagcaca ccaaggtggc | | 2015 |
| ccggaagaac cagaagtgca gcccctctca caggcagctc tgagccgcgc tttcccctcc | | 2075 |
| tccctgggat ggacgctgcc gggagactgc cagtggagac ggaatctgcc gctttgtctg | | 2135 |
| tccagccgtg tgtgcatgtg ccgaggtgcg tcccccgttg tgcctggttc gtgccatgcc | | 2195 |
| cttacacgtg cgtgtgagtg tgtgtgtgtg tctgtaggtg cgcacttacc tgcttgagct | | 2255 |
| ttctgtgcat gtgcaggtcg ggggtgtggt cgtcatgctg tccgtgcttg ctggtgcctc | | 2315 |
| ttttcagtag tgagcagcat ctagtttccc tggtgcccttt ccctggaggt ctctccctcc | | 2375 |
| cccagagccc ctcatgccac agtggtactc tgtgtctggc aggctactct gcccacccca | | 2435 |
| gcatcagcac agctctcctc ctccatctca gactgtggaa ccaaagctgg cccagttgtc | | 2495 |
| catgacaaaa gaggcttttg ggccaaaatg tgagggtggt gggtgggatg gcagggaag | | 2555 |
| gaatcctggt ggaagtcttg ggtgttagtg tcagccatgg gaaatgagcc agcccaaggg | | 2615 |
| catcatcctc agcagcatcg aggaagggcc gaggaatgtg aagccagatc tcgggactca | | 2675 |

```
gattggaatg ttacatctgt ctttcatctc ccagatcctg aaacagcag tgtatatttt    2735 tggtggtggt gggtttgggg tggggaaggg aagggcgggc aaggagtggg gagggagtct    2795
ggggtgggag ggaggcatct gcatgggtct tcttttactg gactgtctga tcagggtgga    2855
gggaaggtga gaggtttgca tccacttcag gagccctact gaagggaaca gcctgagccg    2915
aacatgttat ttaacctgag tatagtattt aacgaagcct agaagcacgg ctgtgggtgg    2975
tgatttggtc agcatatctt aggtatataa taactttgaa gccataactt ttaactggag    3035
tggtttgatt tcttttttta attttattgg gagggtttgg attttaactt ttttaatgt     3095 tgttaaatat taagttttg taaaaggaaa accatctctg tgattacctc tcaatctatt      3155 tgttttaaa gaaatcccta aaaaaaaaa ttatccaatt gaacgcacat agctcaatca       3215
cactggaaat gtttgtcctt gcacctgagc ctgttccac tcagcagtga gagttcctct      3275
ttgccctgag gctcagtctc tctcgtattt tgtccccacc cccaattcct tgagtggttt     3335
ttgctctagg gccctttctt gcactgtcca gctggttgta ccctctccag gcatttattc     3395
aacaaatgtg ggtgaagtgc ctgctgggtg ccaggtgctg ggaatacatc tgtggacaag     3455
acatgcttgg gtcctactcc tggagcactg taaaaagagc tgattcaagt aagtagatgc     3515 ctgtttgag accagaaggt ttcataattg gttctacgac ccttttgagc ctagaattat      3575
tgttcttata taagatcact gaagaaagag gaaccccac aaccccctcc acaaagagac       3635
caggggcggg tgatgagacc tggggtttag aaccccaggt gagacctcaa atcactgcat     3695
tcattctgag cccccttcct gtccccaggg gaggtgtatt tgtatgtag ccttagagca      3755 tctctgcctc caacccagca gttctctgcc aaagcttgtg gaggagggag agccctgtcc    3815
ctgccctcag gctccccagt gctcctggcc cttctatta tttgactgat tattgcttct     3875
ttccttgcat taaaggagat cttcccctaa cctttgggcc aatttactgg ccactaattt    3935
cgtttaaata ccattgtgtc attgggggga ccgtctttac ccctgctgac ctcccaccta    3995
tccgccctgc agcagaacct tggcggttta taggtaatga tggaacttag actcctcttc   4055
ccagagtcac aagtagcctc tgggatctgc caacacacgt ccactcccaa gccactagcc   4115 cactcccag ttggcccttc tgcccttacc ccacacacag tccaactctt ccacctctgg    4175
ggaagatgga gcaggtcttt gggaagctcc cacacccacc tctgccactc ttaacactaa   4235
gtgagagttg gggagaaact gaagccgtgt ttttggcccc ccgaggctaa ccctgatcca   4295
tagtgctacc tgcacctctg gattctggat tcacagacca agtccaagcc cgttcttacg   4355
tcgccataaa ggccccgaa cggcattctc ggtacttctg tttgtttttg tacattttat    4415
tagaaaggac tgtaaaatag ccacttagac actttacctc ttcagtatgc aaatgtaaat   4475
aaattgtaat ataggaaatc ttttgtttta atataagaat gagcctgtcc aatttctgct   4535
gtacattatt aaaagtttta ttcacagag                                      4564
```

<210> SEQ ID NO 24
<211> LENGTH: 505
<212> TYPE: PRT
<213> ORGANISM: Homo sapiens

<400> SEQUENCE: 24

Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

-continued

Leu Cys Ala Cys Thr Ser Cys Leu Gln Ala Asn Tyr Thr Cys Glu Thr
            35                  40                  45

Asp Gly Ala Cys Met Val Ser Ile Phe Asn Leu Asp Gly Met Glu His
 50                  55                  60

His Val Arg Thr Cys Ile Pro Lys Val Glu Leu Val Pro Ala Gly Lys
 65                  70                  75                  80

Pro Phe Tyr Cys Leu Ser Ser Glu Asp Leu Arg Asn Thr His Cys Cys
                 85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
       115                 120                 125

Gly Ile Ile Ala Gly Pro Val Phe Leu Leu Phe Leu Ile Ile Ile Ile
       130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
            165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
       195                 200                 205

Leu Gln Glu Ile Ile Gly Lys Gly Arg Phe Gly Glu Val Trp Arg Gly
       210                 215                 220

Arg Trp Arg Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
            245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
       275                 280                 285

Ser Leu Phe Asp Tyr Leu Asn Arg Tyr Thr Val Thr Ile Glu Gly Met
       290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
            325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
       355                 360                 365

Ile Ala Pro Asn Gln Arg Val Gly Thr Lys Arg Tyr Met Ala Pro Glu
       370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
            405                 410                 415

Cys Asn Ser Gly Gly Val His Glu Glu Tyr Gln Leu Pro Tyr Tyr Asp
            420                 425                 430

Leu Val Pro Ser Asp Pro Ser Ile Glu Glu Met Arg Lys Val Val Cys
       435                 440                 445

Asp Gln Lys Leu Arg Pro Asn Ile Pro Asn Trp Trp Gln Ser Tyr Glu

```
                450                 455                 460
Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505

<210> SEQ ID NO 25
<211> LENGTH: 4516
<212> TYPE: DNA
<213> ORGANISM: Homo sapiens
<220> FEATURE:
<221> NAME/KEY: CDS
<222> LOCATION: (186)..(1547)

<400> SEQUENCE: 25
aatgcttctc ctaagcacct cgtgtgtgtt cttcggcctc actgctctgt ggcttaggta      60
tctgtgctgt ggggtttgag aaacatggtg aaggtgtatg aacagagctt gacatttgtg     120
ctctgctgtg tgcgtgcacc agctgcctcc aggccaacta cacgtgtgag acagatgggg     180 cctgc atg gtt tcc att ttc aat ctg gat ggg atg gag cac cat gtg cgc    230
      Met Val Ser Ile Phe Asn Leu Asp Gly Met Glu His His Val Arg
      1               5                  10                  15 acc tgc atc ccc aaa gtg gag ctg gtc cct gcc ggg aag ccc ttc tac        278
Thr Cys Ile Pro Lys Val Glu Leu Val Pro Ala Gly Lys Pro Phe Tyr
                 20                  25                  30 tgc ctg agc tcg gag gac ctg cgc aac acc cac tgc tgc tac act gac        326
Cys Leu Ser Ser Glu Asp Leu Arg Asn Thr His Cys Cys Tyr Thr Asp
             35                  40                  45 tac tgc aac agg atc gac ttg agg gtg ccc agt ggt cac ctc aag gag        374
Tyr Cys Asn Arg Ile Asp Leu Arg Val Pro Ser Gly His Leu Lys Glu
         50                  55                  60 cct gag cac ccg tcc atg tgg ggc ccg gtg gag ctg gta ggc atc atc        422
Pro Glu His Pro Ser Met Trp Gly Pro Val Glu Leu Val Gly Ile Ile
     65                  70                  75 gcc ggc ccg gtg ttc ctc ctg ttc ctc atc atc atc att gtt ttc ctt        470
Ala Gly Pro Val Phe Leu Leu Phe Leu Ile Ile Ile Ile Val Phe Leu
 80                  85                  90                  95 gtc att aac tat cat cag cgt gtc tat cac aac cgc cag aga ctg gac        518
Val Ile Asn Tyr His Gln Arg Val Tyr His Asn Arg Gln Arg Leu Asp
                100                 105                 110 atg gaa gat ccc tca tgt gag atg tgt ctc tcc aaa gac aag acg ctc        566
Met Glu Asp Pro Ser Cys Glu Met Cys Leu Ser Lys Asp Lys Thr Leu
            115                 120                 125 cag gat ctt gtc tac gat ctc tcc acc tca ggg tct ggc tca ggg tta       614
Gln Asp Leu Val Tyr Asp Leu Ser Thr Ser Gly Ser Gly Ser Gly Leu
        130                 135                 140 ccc ctc ttt gtc cag cgc aca gtg gcc cga acc atc gtt tta caa gag       662
Pro Leu Phe Val Gln Arg Thr Val Ala Arg Thr Ile Val Leu Gln Glu
    145                 150                 155 att att ggc aag ggt cgg ttt ggg gaa gta tgg cgg ggc cgc tgg agg       710
Ile Ile Gly Lys Gly Arg Phe Gly Glu Val Trp Arg Gly Arg Trp Arg
160                 165                 170                 175 ggt ggt gat gtg gct gtg aaa ata ttc tct tct cgt gaa gaa cgg tct       758
Gly Gly Asp Val Ala Val Lys Ile Phe Ser Ser Arg Glu Glu Arg Ser
                180                 185                 190 tgg ttc agg gaa gca gag ata tac cag acg gtc atg ctg cgc cat gaa       806
Trp Phe Arg Glu Ala Glu Ile Tyr Gln Thr Val Met Leu Arg His Glu
            195                 200                 205
```

```
aac atc ctt gga ttt att gct gct gac aat aaa gat aat ggc acc tgg      854
Asn Ile Leu Gly Phe Ile Ala Ala Asp Asn Lys Asp Asn Gly Thr Trp
        210                 215                 220 aca cag ctg tgg ctt gtt tct gac tat cat gag cac ggg tcc ctg ttt      902
Thr Gln Leu Trp Leu Val Ser Asp Tyr His Glu His Gly Ser Leu Phe
    225                 230                 235 gat tat ctg aac cgg tac aca gtg aca att gag ggg atg att aag ctg      950
Asp Tyr Leu Asn Arg Tyr Thr Val Thr Ile Glu Gly Met Ile Lys Leu
240                 245                 250                 255 gcc ttg tct gct gct agt ggg ctg gca cac ctg cac atg gag atc gtg      998
Ala Leu Ser Ala Ala Ser Gly Leu Ala His Leu His Met Glu Ile Val
                260                 265                 270 ggc acc caa ggg aag cct gga att gct cat cga gac tta aag tca aag     1046
Gly Thr Gln Gly Lys Pro Gly Ile Ala His Arg Asp Leu Lys Ser Lys
            275                 280                 285 aac att ctg gtg aag aaa aat ggc atg tgt gcc ata gca gac ctg ggc     1094
Asn Ile Leu Val Lys Lys Asn Gly Met Cys Ala Ile Ala Asp Leu Gly
        290                 295                 300 ctg gct gtc cgt cat gat gca gtc act gac acc att gac att gcc ccg     1142
Leu Ala Val Arg His Asp Ala Val Thr Asp Thr Ile Asp Ile Ala Pro
    305                 310                 315 aat cag agg gtg ggg acc aaa cga tac atg gcc cct gaa gta ctt gat     1190
Asn Gln Arg Val Gly Thr Lys Arg Tyr Met Ala Pro Glu Val Leu Asp
320                 325                 330                 335 gaa acc att aat atg aaa cac ttt gac tcc ttt aaa tgt gct gat att     1238
Glu Thr Ile Asn Met Lys His Phe Asp Ser Phe Lys Cys Ala Asp Ile
                340                 345                 350 tat gcc ctc ggg ctt gta tat tgg gag att gct cga aga tgc aat tct     1286
Tyr Ala Leu Gly Leu Val Tyr Trp Glu Ile Ala Arg Arg Cys Asn Ser
            355                 360                 365 gga gga gtc cat gaa gaa tat cag ctg cca tat tac gac tta gtg ccc     1334
Gly Gly Val His Glu Glu Tyr Gln Leu Pro Tyr Tyr Asp Leu Val Pro
        370                 375                 380 tct gac cct tcc att gag gaa atg cga aag gtt gta tgt gat cag aag     1382
Ser Asp Pro Ser Ile Glu Glu Met Arg Lys Val Val Cys Asp Gln Lys
    385                 390                 395 ctg cgt ccc aac atc ccc aac tgg tgg cag agt tat gag gca ctg cgg     1430
Leu Arg Pro Asn Ile Pro Asn Trp Trp Gln Ser Tyr Glu Ala Leu Arg
400                 405                 410                 415 gtg atg ggg aag atg atg cga gag tgt tgg tat gcc aac ggc gca gcc     1478
Val Met Gly Lys Met Met Arg Glu Cys Trp Tyr Ala Asn Gly Ala Ala
                420                 425                 430 cgc ctg acg gcc ctg cgc atc aag aag acc ctc tcc cag ctc agc gtg     1526
Arg Leu Thr Ala Leu Arg Ile Lys Lys Thr Leu Ser Gln Leu Ser Val
            435                 440                 445 cag gaa gac gtg aag atc taa ctgctccctc tctccacacg gagctcctgg        1577
Gln Glu Asp Val Lys Ile
        450 cagcgagaac tacgcacagc tgccgcgttg agcgtacgat ggaggcctac ctctcgtttc   1637 tgcccagccc tctgtggcca ggagccctgg cccgcaagag ggacagagcc cgggagagac   1697 tcgctcactc ccatgttggg tttgagacag acaccttttc tatttacctc ctaatggcat   1757 ggagactctg agagcgaatt gtgtggagaa ctcagtgcca cacctcgaac tggttgtagt   1817 gggaagtccc gcgaaacccg gtgcatctgg cacgtggcca ggagccatga caggggcgct   1877 tgggaggggc cggaggaacc gaggtgttgc cagtgctaag ctgccctgag ggtttccttc   1937 ggggaccagc ccacagcaca ccaaggtggc ccggaagaac cagaagtgca gcccctctca   1997
```

```
caggcagctc tgagccgcgc tttcccctcc tccctgggat ggacgctgcc gggagactgc    2057
cagtggagac ggaatctgcc gctttgtctg tccagccgtg tgtgcatgtg ccagggtgcg    2117
tccccgttg tgcctggttc gtgccatgcc cttacacgtg cgtgtgagtg tgtgtgtgtg     2177
tctgtaggtc gcacttacc tgcttgagct ttctgtgcat gtgcaggtcg ggggtgtggt     2237
cgtcatgctg tccgtgcttg ctggtgcctc ttttcagtag tgagcagcat ctagtttccc    2297
tggtgccctt ccctggaggt ctctccctcc cccagagccc tcatgccac agtggtactc     2357
tgtgtctggc aggctactct gcccacccca gcatcagcac agctctcctc ctccatctca    2417
gactgtggaa ccaaagctgg cccagttgtc catgacaaaa gaggcttttg gccaaaatg     2477
tgagggtggt gggtgggatg ggcagggaag gaatcctggt ggaagtcttg ggtgttagtg    2537
tcagccatgg gaaatgagcc agcccaaggg catcatcctc agcagcatcg aggaagggcc    2597
gaggaatgtg aagccagatc tcgggactca gattggaatg ttacatctgt ctttcatctc    2657
ccagatcctg gaaacagcag tgtatatttt tggtggtggt gggtttgggg tggggaaggg    2717
aagggcgggc aaggagtggg gagggagtct ggggtgggag ggaggcatct gcatgggtct    2777
tcttttactg gactgtctga tcagggtgga gggaaggtga gaggtttgca tccacttcag    2837
gagccctact gaagggaaca gcctgagccg aacatgttat ttaacctgag tatagtattt    2897
aacgaagcct agaagcacgg ctgtgggtgg tgatttggtc agcatatctt aggtatataa    2957
taactttgaa gccataactt ttaactggag tggtttgatt tctttttta attttattgg     3017
gagggtttgg attttaactt tttttaatgt tgttaaatat taagttttg taaaaggaaa     3077
accatctctg tgattaccte tcaatctatt tgttttaaa gaaatcccta aaaaaaaaa      3137
ttatccaatt gaacgcacat agctcaatca cactggaaat gtttgtcctt gcacctgagc    3197
ctgttcccac tcagcagtga gagttcctct ttgccctgag gctcagtctc tctcgtattt    3257
tgtccccacc cccaattcct tgagtggttt ttgctctagg gccctttctt gcactgtcca    3317
gctggttgta ccctctccag gcattttattc aacaaatgtg ggtgaagtgc ctgctgggtg   3377
ccaggtgctg ggaatacatc tgtggacaag acatgcttgg gtcctactcc tggagcactg    3437
taaaaagagc tgattcaagt aagtagatgc ctgttttgag accagaaggt ttcataattg    3497
gttctacgac ccttttgagc ctagaattat tgttcttata taagatcact gaagaaagag    3557
gaacccccac aacccctcc acaaagagac caggggcggg tgatgagacc tggggtttag     3617
aaccccaggt gagacctcaa atcactgcat tcattctgag cccccttcct gtccccaggg    3677
gaggtgtatt gtgtatgtag ccttagagca tctctgcctc caacccagca gttctctgcc    3737
aaagcttgtg gaggagggag agccctgtcc ctgccctcag gctccccagt gctcctggcc    3797
cttctattta tttgactgat tattgcttct ttccttgcat taaaggagat cttcccctaa    3857
cctttgggcc aatttactgg ccactaattt cgtttaaata ccattgtgtc attgggggga    3917
ccgtctttac ccctgctgac ctcccaccta tccgccctgc agcagaacct tggcggttta    3977
taggtaatga tggaacttag actcctcttc ccagagtcac aagtagcctc tgggatctgc    4037
caacacacgt ccactcccaa gccactagcc cactccccag ttggcccttc tgcccttacc    4097
ccacacacag tccaactctt ccacctctgg ggaagatgga gcaggtcttt gggaagctcc    4157
cacacccacc tctgccactc ttaacactaa gtgagagttg gggagaaact gaagccgtgt    4217
ttttggcccc ccgaggctaa ccctgatcca tagtgctacc tgcacctctg gattctggat    4277
tcacagacca agtccaagcc cgttcttacg tcgcctaaaa ggccccgaa cggcattctc     4337
ggtacttctg tttgtttttg tacatttttat tagaaaggac tgtaaaatag ccacttagac   4397
```

```
actttacctc ttcagtatgc aaatgtaaat aaattgtaat ataggaaatc ttttgtttta    4457
atataagaat gagcctgtcc aatttctgct gtacattatt aaaagttta ttcacagag     4516
```

<210> SEQ ID NO 26
<211> LENGTH: 453
<212> TYPE: PRT
<213> ORGANISM: Homo sapiens

<400> SEQUENCE: 26

```
Met Val Ser Ile Phe Asn Leu Asp Gly Met Glu His His Val Arg Thr
1               5                   10                  15

Cys Ile Pro Lys Val Glu Leu Val Pro Ala Gly Lys Pro Phe Tyr Cys
            20                  25                  30

Leu Ser Ser Glu Asp Leu Arg Asn Thr His Cys Cys Tyr Thr Asp Tyr
        35                  40                  45

Cys Asn Arg Ile Asp Leu Arg Val Pro Ser Gly His Leu Lys Glu Pro
    50                  55                  60

Glu His Pro Ser Met Trp Gly Pro Val Glu Leu Val Gly Ile Ile Ala
65                  70                  75                  80

Gly Pro Val Phe Leu Leu Phe Leu Ile Ile Ile Val Phe Leu Val
                85                  90                  95

Ile Asn Tyr His Gln Arg Val Tyr His Asn Arg Gln Arg Leu Asp Met
            100                 105                 110

Glu Asp Pro Ser Cys Glu Met Cys Leu Ser Lys Asp Lys Thr Leu Gln
        115                 120                 125

Asp Leu Val Tyr Asp Leu Ser Thr Gly Ser Gly Ser Gly Leu Pro
    130                 135                 140

Leu Phe Val Gln Arg Thr Val Ala Arg Thr Ile Val Leu Gln Glu Ile
145                 150                 155                 160

Ile Gly Lys Gly Arg Phe Gly Glu Val Trp Arg Gly Arg Trp Arg
                165                 170                 175

Gly Asp Val Ala Val Lys Ile Phe Ser Ser Arg Glu Glu Arg Ser Trp
            180                 185                 190

Phe Arg Glu Ala Glu Ile Tyr Gln Thr Val Met Leu Arg His Glu Asn
        195                 200                 205

Ile Leu Gly Phe Ile Ala Ala Asp Asn Lys Asp Asn Gly Thr Trp Thr
    210                 215                 220

Gln Leu Trp Leu Val Ser Asp Tyr His Glu His Gly Ser Leu Phe Asp
225                 230                 235                 240

Tyr Leu Asn Arg Tyr Thr Val Thr Ile Glu Gly Met Ile Lys Leu Ala
                245                 250                 255

Leu Ser Ala Ala Ser Gly Leu Ala His Leu His Met Glu Ile Val Gly
            260                 265                 270

Thr Gln Gly Lys Pro Gly Ile Ala His Arg Asp Leu Lys Ser Lys Asn
        275                 280                 285

Ile Leu Val Lys Lys Asn Gly Met Cys Ala Ile Ala Asp Leu Gly Leu
    290                 295                 300

Ala Val Arg His Asp Ala Val Thr Asp Thr Ile Asp Ile Ala Pro Asn
305                 310                 315                 320

Gln Arg Val Gly Thr Lys Arg Tyr Met Ala Pro Glu Val Leu Asp Glu
                325                 330                 335

Thr Ile Asn Met Lys His Phe Ser Phe Lys Cys Ala Asp Ile Tyr
            340                 345                 350
```

```
Ala Leu Gly Leu Val Tyr Trp Glu Ile Ala Arg Arg Cys Asn Ser Gly
        355                 360                 365

Gly Val His Glu Glu Tyr Gln Leu Pro Tyr Tyr Asp Leu Val Pro Ser
    370                 375                 380

Asp Pro Ser Ile Glu Glu Met Arg Lys Val Val Cys Asp Gln Lys Leu
385                 390                 395                 400

Arg Pro Asn Ile Pro Asn Trp Trp Gln Ser Tyr Glu Ala Leu Arg Val
                405                 410                 415

Met Gly Lys Met Met Arg Glu Cys Trp Tyr Ala Asn Gly Ala Ala Arg
            420                 425                 430

Leu Thr Ala Leu Arg Ile Lys Lys Thr Leu Ser Gln Leu Ser Val Gln
        435                 440                 445

Glu Asp Val Lys Ile
    450

<210> SEQ ID NO 27
<211> LENGTH: 4687
<212> TYPE: DNA
<213> ORGANISM: Homo sapiens
<220> FEATURE:
<221> NAME/KEY: CDS
<222> LOCATION: (78)..(1718)

<400> SEQUENCE: 27
ggggaggcgc cggggggcgcg cgcgcgcgcg ctgggcgctg ctgggctgcg gcggcggcgg      60
cggcggcggt ggttact atg gcg gag tcg gcc gga gcc tcc tcc ttc ttc        110
                   Met Ala Glu Ser Ala Gly Ala Ser Ser Phe Phe
                     1               5                   10 ccc ctt gtt gtc ctc ctg ctc gcc ggc agc ggc ggg tcc ggg ccc cgg       158
Pro Leu Val Val Leu Leu Leu Ala Gly Ser Gly Gly Ser Gly Pro Arg
            15                  20                  25 ggg gtc cag gct ctg ctg tgt gcg tgc acc agc tgc ctc cag gcc aac       206
Gly Val Gln Ala Leu Leu Cys Ala Cys Thr Ser Cys Leu Gln Ala Asn
        30                  35                  40 tac acg tgt gag aca gat ggg gcc tgc atg gtt tcc att ttc aat ctg       254
Tyr Thr Cys Glu Thr Asp Gly Ala Cys Met Val Ser Ile Phe Asn Leu
    45                  50                  55 gat ggg atg gag cac cat gtg cgc acc tgc atc ccc aaa gtg gag ctg       302
Asp Gly Met Glu His His Val Arg Thr Cys Ile Pro Lys Val Glu Leu
60                  65                  70                  75 gtc cct gcc ggg aag ccc ttc tac tgc ctg agc tcg gag gac ctg cgc       350
Val Pro Ala Gly Lys Pro Phe Tyr Cys Leu Ser Ser Glu Asp Leu Arg
                80                  85                  90 aac acc cac tgc tgc tac act gac tac tgc aac agg atc gac ttg agg       398
Asn Thr His Cys Cys Tyr Thr Asp Tyr Cys Asn Arg Ile Asp Leu Arg
            95                 100                 105 gtg ccc agt ggt cac ctc aag gag cct gag cac ccg tcc atg tgg ggc       446
Val Pro Ser Gly His Leu Lys Glu Pro Glu His Pro Ser Met Trp Gly
        110                 115                 120 ccg gtg gag ctg gta ggc atc atc gcc ggc ccg gtg ttc ctg ctg ttc       494
Pro Val Glu Leu Val Gly Ile Ile Ala Gly Pro Val Phe Leu Leu Phe
    125                 130                 135 ctc atc atc atc att gtt ttc ctt gtc att aac tat cat cag cgt gtc       542
Leu Ile Ile Ile Ile Val Phe Leu Val Ile Asn Tyr His Gln Arg Val
140                 145                 150                 155 tat cac aac cgc cag aga ctg gac atg gaa gat ccc tca tgt gag atg       590
Tyr His Asn Arg Gln Arg Leu Asp Met Glu Asp Pro Ser Cys Glu Met
                160                 165                 170 tgt ctc tcc aaa gac aag acg ctc cag gat ctt gtc tac gat ctc tcc       638
```

| | | |
|---|---|---|
| Cys Leu Ser Lys Asp Lys Thr Leu Gln Asp Leu Val Tyr Asp Leu Ser<br>             175                       180                  185 | |
| acc tca ggg tct ggc tca ggg tta ccc ctc ttt gtc cag cgc aca gtg<br>Thr Ser Gly Ser Gly Ser Gly Leu Pro Leu Phe Val Gln Arg Thr Val<br>         190                    195                    200 | 686 |
| gcc cga acc atc gtt tta caa gag att att ggc aag ggt cgg ttt ggg<br>Ala Arg Thr Ile Val Leu Gln Glu Ile Ile Gly Lys Gly Arg Phe Gly<br> 205                    210                    215 | 734 |
| gaa gta tgg cgg ggc cgc tgg agg ggt ggt gat gtg gct gtg aaa ata<br>Glu Val Trp Arg Gly Arg Trp Arg Gly Gly Asp Val Ala Val Lys Ile<br>220                  225                    230              235 | 782 |
| ttc tct tct cgt gaa gaa cgg tct tgg ttc agg gaa gca gag ata tac<br>Phe Ser Ser Arg Glu Glu Arg Ser Trp Phe Arg Glu Ala Glu Ile Tyr<br>             240                    245                  250 | 830 |
| cag acg gtc atg ctg cgc cat gaa aac atc ctt gga ttt att gct gct<br>Gln Thr Val Met Leu Arg His Glu Asn Ile Leu Gly Phe Ile Ala Ala<br>                 255                    260                  265 | 878 |
| gac aat aaa gca gac tgc tca ttc ctc aca ttg cca tgg gaa gtt gta<br>Asp Asn Lys Ala Asp Cys Ser Phe Leu Thr Leu Pro Trp Glu Val Val<br>         270                    275                    280 | 926 |
| atg gtc tct gct gcc ccc aag ctg agg agc ctt aga ctc caa tac aag<br>Met Val Ser Ala Ala Pro Lys Leu Arg Ser Leu Arg Leu Gln Tyr Lys<br>285                  290                    295 | 974 |
| gga gga agg gga aga gca aga ttt tta ttc cca ctg aat aat ggc acc<br>Gly Gly Arg Gly Arg Ala Arg Phe Leu Phe Pro Leu Asn Asn Gly Thr<br>300                  305                    310              315 | 1022 |
| tgg aca cag ctg tgg ctt gtt tct gac tat cat gag cac ggg tcc ctg<br>Trp Thr Gln Leu Trp Leu Val Ser Asp Tyr His Glu His Gly Ser Leu<br>             320                    325                  330 | 1070 |
| ttt gat tat ctg aac cgg tac aca gtg aca att gag ggg atg att aag<br>Phe Asp Tyr Leu Asn Arg Tyr Thr Val Thr Ile Glu Gly Met Ile Lys<br>             335                    340                  345 | 1118 |
| ctg gcc ttg tct gct gct agt ggg ctg gca cac ctg cac atg gag atc<br>Leu Ala Leu Ser Ala Ala Ser Gly Leu Ala His Leu His Met Glu Ile<br>                 350                    355                  360 | 1166 |
| gtg ggc acc caa ggg aag cct gga att gct cat cga gac tta aag tca<br>Val Gly Thr Gln Gly Lys Pro Gly Ile Ala His Arg Asp Leu Lys Ser<br>365                  370                    375 | 1214 |
| aag aac att ctg gtg aag aaa aat ggc atg tgt gcc ata gca gac ctg<br>Lys Asn Ile Leu Val Lys Lys Asn Gly Met Cys Ala Ile Ala Asp Leu<br>380                  385                    390              395 | 1262 |
| ggc ctg gct gtc cgt cat gat gca gtc act gac acc att gac att gcc<br>Gly Leu Ala Val Arg His Asp Ala Val Thr Asp Thr Ile Asp Ile Ala<br>             400                    405                  410 | 1310 |
| ccg aat cag agg gtg ggg acc aaa cga tac atg gcc cct gaa gta ctt<br>Pro Asn Gln Arg Val Gly Thr Lys Arg Tyr Met Ala Pro Glu Val Leu<br>             415                    420                  425 | 1358 |
| gat gaa acc att aat atg aaa cac ttt gac tcc ttt aaa tgt gct gat<br>Asp Glu Thr Ile Asn Met Lys His Phe Asp Ser Phe Lys Cys Ala Asp<br>         430                    435                    440 | 1406 |
| att tat gcc ctc ggg ctt gta tat tgg gag att gct cga aga tgc aat<br>Ile Tyr Ala Leu Gly Leu Val Tyr Trp Glu Ile Ala Arg Arg Cys Asn<br>445                  450                    455 | 1454 |
| tct gga gga gtc cat gaa gaa tat cag ctg cca tat tac gac tta gtg<br>Ser Gly Gly Val His Glu Glu Tyr Gln Leu Pro Tyr Tyr Asp Leu Val<br>460                  465                    470              475 | 1502 |
| ccc tct gac cct tcc att gag gaa atg cga aag gtt gta tgt gat cag<br>Pro Ser Asp Pro Ser Ile Glu Glu Met Arg Lys Val Val Cys Asp Gln<br>         480                    485                    490 | 1550 |

```
aag ctg cgt ccc aac atc ccc aac tgg tgg cag agt tat gag gca ctg      1598
Lys Leu Arg Pro Asn Ile Pro Asn Trp Trp Gln Ser Tyr Glu Ala Leu
            495                 500                 505 cgg gtg atg ggg aag atg atg cga gag tgt tgg tat gcc aac ggc gca      1646
Arg Val Met Gly Lys Met Met Arg Glu Cys Trp Tyr Ala Asn Gly Ala
        510                 515                 520 gcc cgc ctg acg gcc ctg cgc atc aag aag acc ctc tcc cag ctc agc      1694
Ala Arg Leu Thr Ala Leu Arg Ile Lys Lys Thr Leu Ser Gln Leu Ser
    525                 530                 535 gtg cag gaa gac gtg aag atc taa ctgctccctc tctccacacg gagctcctgg     1748
Val Gln Glu Asp Val Lys Ile
540             545 cagcgagaac tacgcacagc tgccgcgttg agcgtacgat ggaggcctac ctctcgtttc    1808
tgccagccc tctgtggcca ggagccctgg cccgcaagag ggacagagcc cgggagagac     1868
tcgctcactc ccatgttggg tttgagacag acacctttc tatttacctc ctaatggcat     1928
ggagactctg agagcgaatt gtgtggagaa ctcagtgcca cacctcgaac tggttgtagt    1988
gggaagtccc gcgaaacccg gtgcatctgg cacgtggcca ggagccatga cagggcgct     2048
tgggaggggc cggaggaacc gaggtgttgc cagtgctaag ctgccctgag ggtttccttc    2108
ggggaccagc ccacagcaca ccaaggtggc ccggaagaac cagaagtgca gcccctctca    2168
caggcagctc tgagccgcgc tttcccctcc tccctgggat ggacgctgcc gggagactgc    2228
cagtggagac ggaatctgcc gctttgtctg tccagccgtg tgtgcatgtg ccgaggtgcg    2288
tccccgttg tgcctggttc gtgccatgcc cttacacgtg cgtgtgagtg tgtgtgtgtg     2348
tctgtaggtg cgcacttacc tgcttgagct ttctgtgcat gtgcaggtcg ggggtgtggt    2408
cgtcatgctg tccgtgcttg ctggtgcctc ttttcagtag tgagcagcat ctagtttccc    2468
tggtgccctt ccctggaggt ctctccctcc cccagagccc ctcatgccac agtggtactc    2528
tgtgtctggc aggctactct gcccacccca gcatcagcac agctctcctc ctccatctca    2588
gactgtggaa ccaaagctgg cccagttgtc catgacaaaa gaggcttttg ggccaaaatg    2648
tgagggtggt gggtgggatg ggcagggaag gaatcctggt ggaagtcttg ggtgttagtg    2708
tcagccatgg gaaatgagcc agcccaaggg catcatcctc agcagcatcg aggaagggcc    2768
gaggaatgtg aagccagatc tcgggactca gattggaatg ttacatctgt ctttcatctc    2828
ccagatcctg gaaacagcag tgtatatttt tggtggtggt gggtttgggg tgggaaggg    2888
aagggcgggc aaggagtggg gagggagtct ggggtgggag ggaggcatct gcatgggtct    2948
tcttttactg gactgtctga tcagggtgga gggaaggtga gaggtttgca tccacttcag    3008
gagccctact gaagggaaca gcctgagccg aacatgttat ttaacctgag tatagtattt    3068
aacgaagcct agaagcacgg ctgtgggtgg tgatttggtc agcatatctt aggtatataa    3128
taactttgaa gccataactt ttaactggag tggtttgatt tctttttta attttattgg     3188
gagggtttgg attttaactt ttttaatgt tgttaaatat taagtttttg taaaaggaaa     3248
accatctctg tgattacctc tcaatctatt tgttttttaaa gaaatcccta aaaaaaaaaa   3308
ttatccaatt gaacgcacat agctcaatca cactggaaat gtttgtcctt gcacctgagc    3368
ctgttcccac tcagcagtga gagttcctct ttgccctgag gctcagtctc tctcgtatt    3428
tgtccccacc cccaattcct tgagtggttt ttgctctagg gcccttctt gcactgtcca    3488
gctggttgta ccctctccag gcatttattc aacaaatgtg ggtgaagtgc ctgctgggtg    3548
ccaggtgctg ggaatacatc tgtggacaag acatgcttgg gtcctactcc tggagcactg    3608
taaaagagc tgattcaagt aagtagatgc ctgttttgag accagaaggt ttcataattg     3668
```

```
gttctacgac cctttttgagc ctagaattat tgttcttata taagatcact gaagaaagag   3728 gaaccccccac aaccccctcc acaaagagac caggggcggg tgatgagacc tggggtttag   3788
aaccccaggt gagacctcaa atcactgcat tcattctgag ccccttcct gtccccaggg    3848 gaggtgtatt gtgtatgtag ccttagagca tctctgcctc caacccagca gttctctgcc   3908
aaagcttgtg gaggagggag agccctgtcc ctgccctcag gctccccagt gctcctggcc   3968
cttctattta tttgactgat tattgcttct ttccttgcat taaaggagat cttcccctaa   4028
cctttgggcc aatttactgg ccactaattt cgtttaaata ccattgtgtc attgggggga   4088
ccgtctttac ccctgctgac ctcccaccta tccgccctgc agcagaacct tggcggttta   4148
taggtaatga tggaacttag actcctcttc ccagagtcac aagtagcctc tgggatctgc   4208
caacacacgt ccactcccaa gccactagcc cactccccag ttggcccttc tgcccttacc   4268
ccacacacag tccaactctt ccacctctgg ggaagatgga gcaggtcttt gggaagctcc   4328
cacacccacc tctgccactc ttaacactaa gtgagagttg gggagaaact gaagccgtgt   4388
ttttggcccc ccgaggctaa ccctgatcca tagtgctacc tgcacctctg gattctggat   4448
tcacagacca agtccaagcc cgttcttacg tcgccataaa ggcccccgaa cggcattctc   4508
ggtacttctg tttgttttg tacattttat tagaaaggac tgtaaaatag ccacttagac    4568
actttacctc ttcagtatgc aaatgtaaat aaattgtaat ataggaaatc ttttgtttta   4628
atataagaat gagcctgtcc aatttctgct gtacattatt aaaagttttta ttcacagag   4687
```

<210> SEQ ID NO 28
<211> LENGTH: 546
<212> TYPE: PRT
<213> ORGANISM: Homo sapiens

<400> SEQUENCE: 28

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190
```

```
Ser Gly Leu Pro Leu Phe Val Gln Arg Thr Val Ala Arg Thr Ile Val
            195                 200                 205
Leu Gln Glu Ile Ile Gly Lys Gly Arg Phe Gly Glu Val Trp Arg Gly
        210                 215                 220
Arg Trp Arg Gly Gly Asp Val Ala Val Lys Ile Phe Ser Ser Arg Glu
225                 230                 235                 240
Glu Arg Ser Trp Phe Arg Glu Ala Glu Ile Tyr Gln Thr Val Met Leu
                245                 250                 255
Arg His Glu Asn Ile Leu Gly Phe Ile Ala Ala Asp Asn Lys Ala Asp
            260                 265                 270
Cys Ser Phe Leu Thr Leu Pro Trp Glu Val Val Met Val Ser Ala Ala
        275                 280                 285
Pro Lys Leu Arg Ser Leu Arg Leu Gln Tyr Lys Gly Gly Arg Gly Arg
    290                 295                 300
Ala Arg Phe Leu Phe Pro Leu Asn Asn Gly Thr Trp Thr Gln Leu Trp
305                 310                 315                 320
Leu Val Ser Asp Tyr His Glu His Gly Ser Leu Phe Asp Tyr Leu Asn
                325                 330                 335
Arg Tyr Thr Val Thr Ile Glu Gly Met Ile Lys Leu Ala Leu Ser Ala
            340                 345                 350
Ala Ser Gly Leu Ala His Leu His Met Glu Ile Val Gly Thr Gln Gly
        355                 360                 365
Lys Pro Gly Ile Ala His Arg Asp Leu Lys Ser Lys Asn Ile Leu Val
    370                 375                 380
Lys Lys Asn Gly Met Cys Ala Ile Ala Asp Leu Gly Leu Ala Val Arg
385                 390                 395                 400
His Asp Ala Val Thr Asp Thr Ile Asp Ile Ala Pro Asn Gln Arg Val
                405                 410                 415
Gly Thr Lys Arg Tyr Met Ala Pro Glu Val Leu Asp Glu Thr Ile Asn
            420                 425                 430
Met Lys His Phe Asp Ser Phe Lys Cys Ala Asp Ile Tyr Ala Leu Gly
        435                 440                 445
Leu Val Tyr Trp Glu Ile Ala Arg Arg Cys Asn Ser Gly Gly Val His
    450                 455                 460
Glu Glu Tyr Gln Leu Pro Tyr Tyr Asp Leu Val Pro Ser Asp Pro Ser
465                 470                 475                 480
Ile Glu Glu Met Arg Lys Val Val Cys Asp Gln Lys Leu Arg Pro Asn
                485                 490                 495
Ile Pro Asn Trp Trp Gln Ser Tyr Glu Ala Leu Arg Val Met Gly Lys
            500                 505                 510
Met Met Arg Glu Cys Trp Tyr Ala Asn Gly Ala Ala Arg Leu Thr Ala
        515                 520                 525
Leu Arg Ile Lys Lys Thr Leu Ser Gln Leu Ser Val Gln Glu Asp Val
    530                 535                 540
Lys Ile
545

<210> SEQ ID NO 29
<211> LENGTH: 1834
<212> TYPE: DNA
<213> ORGANISM: Homo sapiens
<220> FEATURE:
<221> NAME/KEY: CDS
<222> LOCATION: (359)..(1393)

<400> SEQUENCE: 29
```

-continued

```
ttgggaaggg tttccagaag gtgggaaatg tcacctgatt cacactgaac ttttgaaagc      60
tccccacccc caaggagccg cgcacaccct cgctcgcggc cgccctccca cagccccaca     120
cactgggaga ccgcccaccg caaaccgcgg agaccccgt ctagatttaa agcgcggctg     180
cgcccggctt ctgacgtcca ttgaatcgcg cgggcggccg gcggcgagcg cggggctgcg     240
ccgggatcgc tgcgccctcc gccgctggcc tctgcgacgc gcgccgctcg cccgagccac     300
ccgccgccgc gccggctccc cgcgccgctg cgctcctcgc cccgcgcctg cccccagg      358
```

| | | | | | | | | | | | | | | | | |
|---|---|---|---|---|---|---|---|---|---|---|---|---|---|---|---|---|
| atg | gtc | cgc | gcg | agg | cac | cag | ccg | ggt | ggg | ctt | tgc | ctc | ctg | ctg | ctg | 406 |
| Met | Val | Arg | Ala | Arg | His | Gln | Pro | Gly | Gly | Leu | Cys | Leu | Leu | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctg | ctc | tgc | cag | ttc | atg | gag | gac | cgc | agt | gcc | cag | gct | ggg | aac | tgc | 454 |
| Leu | Leu | Cys | Gln | Phe | Met | Glu | Asp | Arg | Ser | Ala | Gln | Ala | Gly | Asn | Cys | |
| | | 20 | | | | | 25 | | | | | 30 | | | | |

| | | | | | | | | | | | | | | | | |
|---|---|---|---|---|---|---|---|---|---|---|---|---|---|---|---|---|
| tgg | ctc | cgt | caa | gcg | aag | aac | ggc | cgc | tgc | cag | gtc | ctg | tac | aag | acc | 502 |
| Trp | Leu | Arg | Gln | Ala | Lys | Asn | Gly | Arg | Cys | Gln | Val | Leu | Tyr | Lys | Thr | |
| | | | 35 | | | | | 40 | | | | | 45 | | | |

| | | | | | | | | | | | | | | | | |
|---|---|---|---|---|---|---|---|---|---|---|---|---|---|---|---|---|
| gaa | ctg | agc | aag | gag | gag | tgc | tgc | agc | acc | ggc | cgg | ctg | agc | acc | tcg | 550 |
| Glu | Leu | Ser | Lys | Glu | Glu | Cys | Cys | Ser | Thr | Gly | Arg | Leu | Ser | Thr | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| tgg | acc | gag | gag | gac | gtg | aat | gac | aac | aca | ctc | ttc | aag | tgg | atg | att | 598 |
| Trp | Thr | Glu | Glu | Asp | Val | Asn | Asp | Asn | Thr | Leu | Phe | Lys | Trp | Met | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | aac | ggg | ggc | gcc | ccc | aac | tgc | atc | ccc | tgt | aaa | gaa | acg | tgt | gag | 646 |
| Phe | Asn | Gly | Gly | Ala | Pro | Asn | Cys | Ile | Pro | Cys | Lys | Glu | Thr | Cys | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| aac | gtg | gac | tgt | gga | cct | ggg | aaa | aaa | tgc | cga | atg | aac | aag | aag | aac | 694 |
| Asn | Val | Asp | Cys | Gly | Pro | Gly | Lys | Lys | Cys | Arg | Met | Asn | Lys | Lys | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | ccc | cgc | tgc | gtc | tgc | gcc | ccg | gat | tgt | tcc | aac | atc | acc | tgg | aag | 742 |
| Lys | Pro | Arg | Cys | Val | Cys | Ala | Pro | Asp | Cys | Ser | Asn | Ile | Thr | Trp | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| ggt | cca | gtc | tgc | ggg | ctg | gat | ggg | aaa | acc | tac | cgc | aat | gaa | tgt | gca | 790 |
| Gly | Pro | Val | Cys | Gly | Leu | Asp | Gly | Lys | Thr | Tyr | Arg | Asn | Glu | Cys | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| ctc | cta | aag | gca | aga | tgt | aaa | gag | cag | cca | gaa | ctg | gaa | gtc | cag | tac | 838 |
| Leu | Leu | Lys | Ala | Arg | Cys | Lys | Glu | Gln | Pro | Glu | Leu | Glu | Val | Gln | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| caa | ggc | aga | tgt | aaa | aag | act | tgt | cgg | gat | gtt | ttc | tgt | cca | ggc | agc | 886 |
| Gln | Gly | Arg | Cys | Lys | Lys | Thr | Cys | Arg | Asp | Val | Phe | Cys | Pro | Gly | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| tcc | aca | tgt | gtg | gtg | gac | cag | acc | aat | aat | gcc | tac | tgt | gtg | acc | tgt | 934 |
| Ser | Thr | Cys | Val | Val | Asp | Gln | Thr | Asn | Asn | Ala | Tyr | Cys | Val | Thr | Cys | |
| | | | 180 | | | | | 185 | | | | | 190 | | | |

| | | | | | | | | | | | | | | | | |
|---|---|---|---|---|---|---|---|---|---|---|---|---|---|---|---|---|
| aat | cgg | att | tgc | cca | gag | cct | gct | tcc | tct | gag | caa | tat | ctc | tgt | ggg | 982 |
| Asn | Arg | Ile | Cys | Pro | Glu | Pro | Ala | Ser | Ser | Glu | Gln | Tyr | Leu | Cys | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| aat | gat | gga | gtc | acc | tac | tcc | agt | gcc | tgc | cac | ctg | aga | aag | gct | acc | 1030 |
| Asn | Asp | Gly | Val | Thr | Tyr | Ser | Ser | Ala | Cys | His | Leu | Arg | Lys | Ala | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| tgc | ctg | ctg | ggc | aga | tct | att | gga | tta | gcc | tat | gag | gga | aag | tgt | atc | 1078 |
| Cys | Leu | Leu | Gly | Arg | Ser | Ile | Gly | Leu | Ala | Tyr | Glu | Gly | Lys | Cys | Ile | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aaa | gca | aag | tcc | tgt | gaa | gat | atc | cag | tgc | act | ggt | ggg | aaa | aaa | tgt | 1126 |
| Lys | Ala | Lys | Ser | Cys | Glu | Asp | Ile | Gln | Cys | Thr | Gly | Gly | Lys | Lys | Cys | |
| | | | | 245 | | | | | 250 | | | | | 255 | | |

| | | | | | | | | | | | | | | | | |
|---|---|---|---|---|---|---|---|---|---|---|---|---|---|---|---|---|
| tta | tgg | gat | ttc | aag | gtt | ggg | aga | ggc | cgg | tgt | tcc | ctc | tgt | gat | gag | 1174 |
| Leu | Trp | Asp | Phe | Lys | Val | Gly | Arg | Gly | Arg | Cys | Ser | Leu | Cys | Asp | Glu | |

|  |  |  |  |  |  |  |  |  |  |  |  |  |  |  |  |
|---|---|---|---|---|---|---|---|---|---|---|---|---|---|---|---|
|  |  |  | 260 |  |  |  | 265 |  |  |  | 270 |  |  |  |  |
| ctg<br>Leu | tgc<br>Cys | cct<br>Pro<br>275 | gac<br>Asp | agt<br>Ser | aag<br>Lys | tcg<br>Ser | gat<br>Asp<br>280 | gag<br>Glu | cct<br>Pro | gtc<br>Val | tgt<br>Cys<br>285 | gcc<br>Ala | agt<br>Ser | gac<br>Asp | aat<br>Asn | 1222 |
| gcc<br>Ala | act<br>Thr | tat<br>Tyr<br>290 | gcc<br>Ala | agc<br>Ser | gag<br>Glu | tgt<br>Cys<br>295 | gcc<br>Ala | atg<br>Met | aag<br>Lys | gaa<br>Glu | gct<br>Ala<br>300 | gcc<br>Ala | tgc<br>Cys | tcc<br>Ser | tca<br>Ser | 1270 |
| ggt<br>Gly<br>305 | gtg<br>Val | cta<br>Leu | ctg<br>Leu | gaa<br>Glu<br>310 | gta<br>Val | aag<br>Lys | cac<br>His | tcc<br>Ser | gga<br>Gly<br>315 | tct<br>Ser | tgc<br>Cys | aac<br>Asn | tcc<br>Ser | att<br>Ile<br>320 | tcg<br>Ser | 1318 |
| gaa<br>Glu | gac<br>Asp | acc<br>Thr | gag<br>Glu | gaa<br>Glu<br>325 | gag<br>Glu | gag<br>Glu | gaa<br>Glu | gat<br>Asp | gaa<br>Glu<br>330 | gac<br>Asp | cag<br>Gln | gac<br>Asp | tac<br>Tyr | agc<br>Ser<br>335 | ttt<br>Phe | 1366 |
| cct<br>Pro | ata<br>Ile | tct<br>Ser | tct<br>Ser<br>340 | att<br>Ile | cta<br>Leu | gag<br>Glu | tgg<br>Trp | taa | actctctata |  | agtgttcagt |  |  |  |  | 1413 |
| gttgacatag | ccttt gtgca | aaaaaaaaaa | aaaaaaaaaa | gaaaagaaaa | aaaagaaaaa | 1473 |
| tatattgtcc | atactgtaaa | taagtgtatg | cttatttatt | tgggggaaa | actatacatt | 1533 |
| aaaggacctt | tgtcctaaag | ctctctccca | ggccaccttg | ttactcattg | gacacggaga | 1593 |
| ggcattcatt | gtgaggtcta | ctggatgagg | cccatagttg | agacttgtag | acatttattt | 1653 |
| atactgtgtc | atgttttata | atttatacat | aaaatgtctg | gttgactgta | taccttgttt | 1713 |
| ttgaagaaat | ttattcgtga | aaggaagagc | agttgttatt | tattgtgagg | tctcttgctt | 1773 |
| gtaaagtaaa | agcttttttt | ccttgtaaac | catttaagtc | cattccttac | tattcactca | 1833 |
| c |  |  |  |  |  | 1834 |

<210> SEQ ID NO 30
<211> LENGTH: 344
<212> TYPE: PRT
<213> ORGANISM: Homo sapiens

<400> SEQUENCE: 30

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

```
Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
            340

<210> SEQ ID NO 31
<211> LENGTH: 1436
<212> TYPE: DNA
<213> ORGANISM: Homo sapiens
<220> FEATURE:
<221> NAME/KEY: CDS
<222> LOCATION: (144)..(1244)

<400> SEQUENCE: 31
aaggactggg gaagactgga tgagaagggt agaagagggt gggtgtggga tggggagggg      60
agagtggaaa ggccctgggc agaccctggc agaagggca  cggggcaggg tgtgagttcc    120
ccactagcag ggccaggtga gct atg gtg ctg cac cta ctg ctc ttc ttg ctg    173
                        Met Val Leu His Leu Leu Leu Phe Leu Leu
                         1               5                  10 ctg acc cca cag ggt ggg cac agc tgc cag ggg ctg gag ctg gcc cgg    221
Leu Thr Pro Gln Gly Gly His Ser Cys Gln Gly Leu Glu Leu Ala Arg
             15                  20                  25 gaa ctt gtt ctg gcc aag gtg agg gcc ctg ttc ttg gat gcc ttg ggg    269
Glu Leu Val Leu Ala Lys Val Arg Ala Leu Phe Leu Asp Ala Leu Gly
         30                  35                  40 ccc ccc gcg gtg acc agg gaa ggt ggg gac cct gga gtc agg cgg ctg    317
Pro Pro Ala Val Thr Arg Glu Gly Gly Asp Pro Gly Val Arg Arg Leu
     45                  50                  55 ccc cga aga cat gcc ctg ggg ggc ttc aca cac agg ggc tct gag ccc    365
Pro Arg Arg His Ala Leu Gly Gly Phe Thr His Arg Gly Ser Glu Pro
 60                  65                  70 gag gaa gag gag gat gtc tcc caa gcc atc ctt ttc cca gcc aca gat    413
Glu Glu Glu Glu Asp Val Ser Gln Ala Ile Leu Phe Pro Ala Thr Asp
75                  80                  85                  90 gcc agc tgt gag gac aag tca gct gcc aga ggg ctg gcc cag gag gct    461
Ala Ser Cys Glu Asp Lys Ser Ala Ala Arg Gly Leu Ala Gln Glu Ala
                 95                 100                 105 gag gag ggc ctc ttc aga tac atg ttc cgg cca tcc cag cat aca cgc    509
Glu Glu Gly Leu Phe Arg Tyr Met Phe Arg Pro Ser Gln His Thr Arg
            110                 115                 120
```

```
agc cgc cag gtg act tca gcc cag ctg tgg ttc cac acc ggg ctg gac      557
Ser Arg Gln Val Thr Ser Ala Gln Leu Trp Phe His Thr Gly Leu Asp
        125                 130                 135 agg cag ggc aca gca gcc tcc aat agc tct gag ccc ctg cta ggc ctg      605
Arg Gln Gly Thr Ala Ala Ser Asn Ser Ser Glu Pro Leu Leu Gly Leu
    140                 145                 150 ctg gca ctg tca ccg gga gga ccc gtg gct gtg ccc atg tct ttg ggc      653
Leu Ala Leu Ser Pro Gly Gly Pro Val Ala Val Pro Met Ser Leu Gly
155                 160                 165                 170 cat gct ccc cct cac tgg gcc gtg ctg cac ctg gcc acc tct gct ctc      701
His Ala Pro Pro His Trp Ala Val Leu His Leu Ala Thr Ser Ala Leu
            175                 180                 185 tct ctg ctg acc cac ccc gtc ctg gtg ctg ctg cgc tgt ccc ctc          749
Ser Leu Leu Thr His Pro Val Leu Val Leu Leu Arg Cys Pro Leu
        190                 195                 200 tgt acc tgc tca gcc cgg cct gag gcc acg ccc ttc ctg gtg gcc cac      797
Cys Thr Cys Ser Ala Arg Pro Glu Ala Thr Pro Phe Leu Val Ala His
            205                 210                 215 act cgg acc aga cca ccc agt gga ggg gag aga gcc cga cgc tca act      845
Thr Arg Thr Arg Pro Pro Ser Gly Gly Glu Arg Ala Arg Arg Ser Thr
220                 225                 230 ccc ctg atg tcc tgg cct tgg tct ccc tct gct ctc cgc ctg ctg cag      893
Pro Leu Met Ser Trp Pro Trp Ser Pro Ser Ala Leu Arg Leu Leu Gln
235                 240                 245                 250 agg cct ccg gag gaa ccg gct gcc cat gcc aac tgc cac aga gta gca      941
Arg Pro Pro Glu Glu Pro Ala Ala His Ala Asn Cys His Arg Val Ala
            255                 260                 265 ctg aac atc tcc ttc cag gag ctg ggc tgg gaa cgg tgg atc gtg tac      989
Leu Asn Ile Ser Phe Gln Glu Leu Gly Trp Glu Arg Trp Ile Val Tyr
        270                 275                 280 cct ccc agt ttc atc ttc cac tac tgt cat ggt ggt tgt ggg ctg cac     1037
Pro Pro Ser Phe Ile Phe His Tyr Cys His Gly Gly Cys Gly Leu His
            285                 290                 295 atc cca cca aac ctg tcc ctt cca gtc cct ggg gct ccc cct acc cca     1085
Ile Pro Pro Asn Leu Ser Leu Pro Val Pro Gly Ala Pro Pro Thr Pro
300                 305                 310 gcc cag ccc tac tcc ttg ctg cca ggg gcc cag ccc tgc tgt gct gct     1133
Ala Gln Pro Tyr Ser Leu Leu Pro Gly Ala Gln Pro Cys Cys Ala Ala
315                 320                 325                 330 ctc cca ggg acc atg agg ccc cta cat gtc cgc acc acc tcg gat gga     1181
Leu Pro Gly Thr Met Arg Pro Leu His Val Arg Thr Thr Ser Asp Gly
            335                 340                 345 ggt tac tct ttc aag tat gag aca gtg ccc aac ctt ctc acg cag cac     1229
Gly Tyr Ser Phe Lys Tyr Glu Thr Val Pro Asn Leu Leu Thr Gln His
        350                 355                 360 tgt gct tgt atc taa gggtgggggg tcttccttct taatcccatg gctggtggcc    1284
Cys Ala Cys Ile
        365 acgcccccac catcatcagc tgggaggaaa ggcagagttg ggaaatagat ggctcccact  1344 cctccctcct ttcacttctc tgcctatggg ctaccctccc cacccactt ctatctcaat   1404 aaagaacaca gtgcatatga cttgacaaaa aa                                1436

<210> SEQ ID NO 32
<211> LENGTH: 366
<212> TYPE: PRT
<213> ORGANISM: Homo sapiens

<400> SEQUENCE: 32
```

```
Met Val Leu His Leu Leu Phe Leu Leu Leu Thr Pro Gln Gly Gly
1               5                   10                  15

His Ser Cys Gln Gly Leu Glu Leu Ala Arg Glu Leu Val Leu Ala Lys
            20                  25                  30

Val Arg Ala Leu Phe Leu Asp Ala Leu Gly Pro Pro Ala Val Thr Arg
        35                  40                  45

Glu Gly Gly Asp Pro Gly Val Arg Arg Leu Pro Arg Arg His Ala Leu
    50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Glu Gly Leu Phe Arg
            100                 105                 110

Tyr Met Phe Arg Pro Ser Gln His Thr Arg Ser Arg Gln Val Thr Ser
            115                 120                 125

Ala Gln Leu Trp Phe His Thr Gly Leu Asp Arg Gln Gly Thr Ala Ala
        130                 135                 140

Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
                165                 170                 175

Ala Val Leu His Leu Ala Thr Ser Ala Leu Ser Leu Leu Thr His Pro
            180                 185                 190

Val Leu Val Leu Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
    210                 215                 220

Ser Gly Gly Glu Arg Ala Arg Arg Ser Thr Pro Leu Met Ser Trp Pro
225                 230                 235                 240

Trp Ser Pro Ser Ala Leu Arg Leu Leu Gln Arg Pro Pro Glu Glu Pro
                245                 250                 255

Ala Ala His Ala Asn Cys His Arg Val Ala Leu Asn Ile Ser Phe Gln
            260                 265                 270

Glu Leu Gly Trp Glu Arg Trp Ile Val Tyr Pro Pro Ser Phe Ile Phe
        275                 280                 285

His Tyr Cys His Gly Gly Cys Gly Leu His Ile Pro Pro Asn Leu Ser
    290                 295                 300

Leu Pro Val Pro Gly Ala Pro Pro Thr Pro Ala Gln Pro Tyr Ser Leu
305                 310                 315                 320

Leu Pro Gly Ala Gln Pro Cys Cys Ala Ala Leu Pro Gly Thr Met Arg
                325                 330                 335

Pro Leu His Val Arg Thr Thr Ser Asp Gly Gly Tyr Ser Phe Lys Tyr
            340                 345                 350

Glu Thr Val Pro Asn Leu Leu Thr Gln His Cys Ala Cys Ile
        355                 360                 365

<210> SEQ ID NO 33
<211> LENGTH: 21
<212> TYPE: DNA
<213> ORGANISM: Artificial Sequence
<220> FEATURE:
<223> OTHER INFORMATION: S7434 sense

<400> SEQUENCE: 33
```
caacagucau caaccacuat t                                              21

<210> SEQ ID NO 34
<211> LENGTH: 21
<212> TYPE: DNA
<213> ORGANISM: Artificial Sequence
<220> FEATURE:
<223> OTHER INFORMATION: S7434 antisense

<400> SEQUENCE: 34
uagugguuga ugacuguuga g                                              21

<210> SEQ ID NO 35
<211> LENGTH: 21
<212> TYPE: DNA
<213> ORGANISM: Artificial Sequence
<220> FEATURE:
<223> OTHER INFORMATION: S7435 sense

<400> SEQUENCE: 35 gaacgggu au guggagauat t                                             21

<210> SEQ ID NO 36
<211> LENGTH: 21
<212> TYPE: DNA
<213> ORGANISM: Artificial Sequence
<220> FEATURE:
<223> OTHER INFORMATION: S7435 antisense

<400> SEQUENCE: 36
uaucuccaca uacccguuct c                                              21

<210> SEQ ID NO 37
<211> LENGTH: 21
<212> TYPE: DNA
<213> ORGANISM: Artificial Sequence
<220> FEATURE:
<223> OTHER INFORMATION: S975 sense

<400> SEQUENCE: 37
ggaucauucg uguacaucat t                                              21

<210> SEQ ID NO 38
<211> LENGTH: 21
<212> TYPE: DNA
<213> ORGANISM: Artificial Sequence
<220> FEATURE:
<223> OTHER INFORMATION: S975 antisense

<400> SEQUENCE: 38
ugauguacac gaaugaucca a                                              21

<210> SEQ ID NO 39
<211> LENGTH: 21
<212> TYPE: DNA
<213> ORGANISM: Artificial Sequence
<220> FEATURE:
<223> OTHER INFORMATION: S976 sense

<400> SEQUENCE: 39
guugcucucc gaaaauuuat t                                              21

<210> SEQ ID NO 40
<211> LENGTH: 21
<212> TYPE: DNA
<213> ORGANISM: Artificial Sequence

```
<220> FEATURE:
<223> OTHER INFORMATION: S976 antisense

<400> SEQUENCE: 40
uaaauuuucg gagagcaact c                                              21

<210> SEQ ID NO 41
<211> LENGTH: 21
<212> TYPE: DNA
<213> ORGANISM: Artificial Sequence
<220> FEATURE:
<223> OTHER INFORMATION: S281 sense

<400> SEQUENCE: 41
ggccgauaug gagaaguaut t                                              21

<210> SEQ ID NO 42
<211> LENGTH: 21
<212> TYPE: DNA
<213> ORGANISM: Artificial Sequence
<220> FEATURE:
<223> OTHER INFORMATION: S281 antisense

<400> SEQUENCE: 42
auacuucucc auaucggcct t                                              21

<210> SEQ ID NO 43
<211> LENGTH: 21
<212> TYPE: DNA
<213> ORGANISM: Artificial Sequence
<220> FEATURE:
<223> OTHER INFORMATION: S282 sense

<400> SEQUENCE: 43
gaaucuggau aguaugcuut t                                              21

<210> SEQ ID NO 44
<211> LENGTH: 21
<212> TYPE: DNA
<213> ORGANISM: Artificial Sequence
<220> FEATURE:
<223> OTHER INFORMATION: S282 antisense

<400> SEQUENCE: 44
aagcauacua uccagauuct g                                              21
```